United States Patent
Datta et al.

(10) Patent No.: US 10,845,365 B2
(45) Date of Patent: *Nov. 24, 2020

(54) ELISA DETECTION OF URINE DEK TO PREDICT AND DIAGNOSE BLADDER CANCER IN HUMANS

(71) Applicants: Antara Datta, Piscataway, NJ (US); Jason Trama, Burlington, NJ (US)

(72) Inventors: Antara Datta, Piscataway, NJ (US); Jason Trama, Burlington, NJ (US)

(73) Assignee: Medical Diagnostic Laboratories, LLC, Hamilton, NJ (US)

(*) Notice: Subject to any disclaimer, the term of this patent is extended or adjusted under 35 U.S.C. 154(b) by 17 days.

This patent is subject to a terminal disclaimer.

(21) Appl. No.: 15/656,082

(22) Filed: Jul. 21, 2017

(65) Prior Publication Data

US 2018/0011097 A1   Jan. 11, 2018

Related U.S. Application Data

(63) Continuation of application No. 14/939,031, filed on Nov. 12, 2015, now Pat. No. 9,746,473, which is a continuation of application No. 14/258,122, filed on Apr. 22, 2014, now Pat. No. 9,255,925, which is a continuation-in-part of application No. 13/317,531, filed on Oct. 20, 2011, now Pat. No. 8,741,582.

(60) Provisional application No. 61/455,406, filed on Oct. 20, 2010, provisional application No. 61/455,405, filed on Oct. 20, 2010.

(51) Int. Cl.
*G01N 33/569* (2006.01)
*G01N 33/574* (2006.01)
*C07K 16/18* (2006.01)

(52) U.S. Cl.
CPC ....... *G01N 33/57407* (2013.01); *C07K 16/18* (2013.01); *G01N 33/574* (2013.01); *G01N 2333/82* (2013.01)

(58) Field of Classification Search
None
See application file for complete search history.

*Primary Examiner* — Lei Yao
(74) *Attorney, Agent, or Firm* — Arnold Braun; Terence Bogie

(57) ABSTRACT

The present invention is directed to a method of detecting a DEK protein in a human urine sample using an ELISA assay. Methods and compositions for detection of DEK using mAb 260-6F9F6 (as detection antibody) and mAb 16-2C9C3 (as capture antibody) in human urine are provided herein. Specifically, the ELISA assay utilizes a capture mAb and a detection mAb to yield a high sensitivity of <50 ng/mL. The presence of DEK in urine is useful in predicting or diagnosing the occurrence of bladder cancer in humans.

9 Claims, 39 Drawing Sheets
Specification includes a Sequence Listing.

| DEK Isoforms | aa 49-82 | aa 325-375 | Isoform recognized by Monoclonal Ab | Isoform recognized by Polyclonal Ab |
|---|---|---|---|---|
| DEK isoform1 | √ | √ | √ | √ |
| DEK isoform2 | - | √ | - | √ |

Figures 30A-30B
Figure 30A
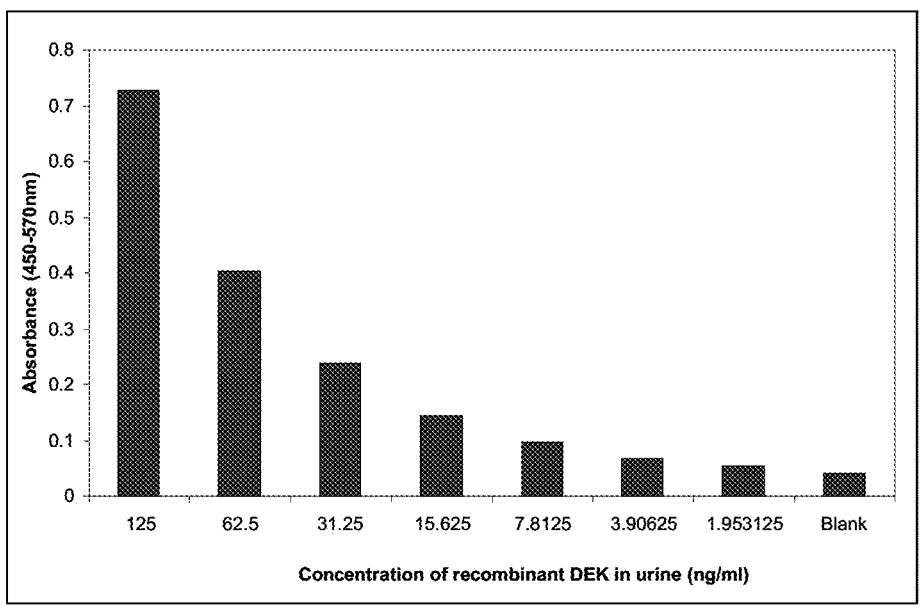
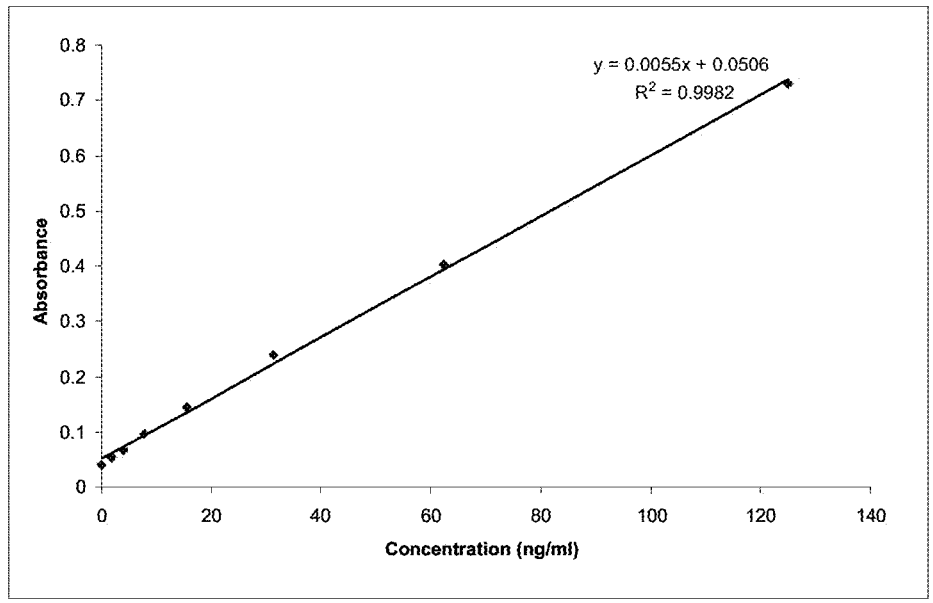

DEK SANDWICH ELISA

Figure 33A
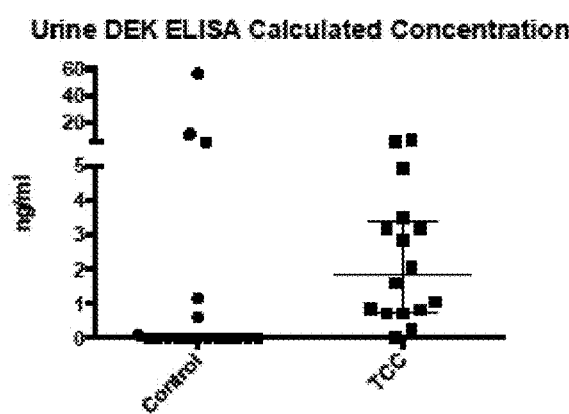
Figure 33B
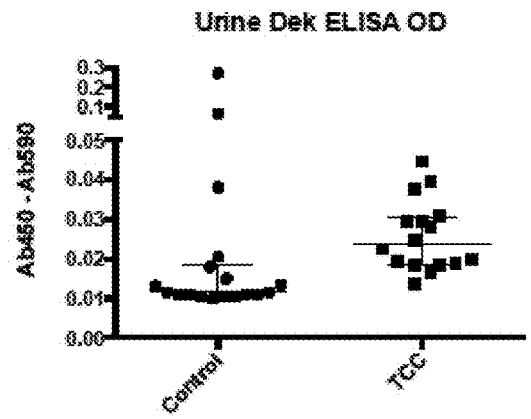
Figure 33C
| | |
|---|---|
| Sensitivity | 82.3% |
| Specificity | 70.58% |
| PPV | 75% |
| NPV | 84.6% |

Figure 35A mAb 16-2C9C3

Heavy Chain

DNA sequence (408 bp): Leader sequence- FR1- CDR1- FR2-CDR2-FR3-CDR3-FR4

ATGATGGTGTTAAGTCTTCTGTTCCTGTTGACAGCCCTTCCGGGTATCCTGTC
AGAGGTGCAGCTTCAGGAGTCAGGACCTAGCCTCGTGAAACCTTCTCAGACT
CTGTCCCTCACCTGTTCTGTCACT<u>GGCGACTCCATCACCAGTGGTTACTGGAA
C</u>TGGATCCGGAAATTCCCAGGGAATAAACTTGAGTACATGGGG<u>TATATAAGT
TACAGTGGTGACACTTACTACAATCCATCTCTCAAAAGT</u>CGATTCTCCATCAC
TCGAGACACATCCAAGAACCAGTTCTACCTGCAATTGAATTCTGTGACTACTG
AGGACACAGCCACATATTACTGTGCAGCC*ATTACTATGGCTACTCTTGCTATGG
ACTA*CTGGGGTCAAGGAACCTCAGTCACCGTCTCCTCA (SEQ ID NO: 10)

CDR1 (SEQ ID NO: 11) is represented by <u>underlined text</u>; CDR2 (SEQ ID NO: 12) is represented by <u>double-underlined text</u>; CDR3 (SEQ ID NO: 13) is represented by *italicized text*

Figure 35B mAb 16-2C9C3

Heavy Chain

Amino Acid sequence (136 AA): Leader sequence-FR1-CDR1-FR2-CDR2-FR3-CDR3-FR4

MMVLSLLFLLTALPGILSEVQLQESGPSLVKPSQTLSLTCSVT<u>GDSITSGYWN</u>WIR
KFPGNKLEYMG<u>YISYSGDTYYNPSLKS</u>RFSITRDTSKNQFYLQLNSVTTEDTATY
YCAA*ITMATLAMDY*WGQGTSVTVSS (SEQ ID NO: 14)

CDR1 (SEQ ID NO: 15) is represented by <u>underlined text</u>; CDR2 (SEQ ID NO: 16) is represented by <u>double-underlined text</u>; CDR3 (SEQ ID NO: 17) is represented by *italicized text*

Figure 36A mAb 16-2C9C3

Light Chain

DNA sequence (393 bp): Leader sequence-FR1-CDR1-FR2-CDR2-FR3-CDR3-FR4

ATGAAGTTGCCTGTTAGGCTGTTGGTGCTGATGTTCTGGATTCCTGCTTCCGG
CAGTGATGTTTTGATGACCCAAACTCCACTCTCCCTGCCTGTCAGTCTTGGAG
AGCAGGCCTCCATCTCTTGT<u>AGATCTAGTCAGAGCATTGAACATCGGAATGG
AAACACCTATTTAGAA</u>TGGTACCTGCAGAAACCAGGCCAGTCTCCAAAACTC
CTGATCTAC<u>AAAGTTTCCAACCGATTCTCT</u>GGGGTCCCAGACAGGTTCAGTGG
CAGTGGATCAGGGACAGATTTCACACTCAAGATCAGCAGAGTGGAGGCTGAG
GATCTGGAGTTTATTACTGC*TTTCAAGGTTCACATGTTCCTGGGACG*TTCGGTG
GAGGCACCAACCTGGAAATCAAA (SEQ ID NO: 18)

CDR1 (SEQ ID NO: 19) is represented by <u>underlined text</u>; CDR2 (SEQ ID NO: 20) is represented by <u>double-underlined text</u>; CDR3 (SEQ ID NO: 21) is represented by *italicized text*

Figure 36B mAb 16-2C9C3

Light Chain

Light chain: Amino Acid sequence (131 AA): Leader sequence-FR1-CDR1-FR2-CDR2-FR3-CDR3-FR4

MKLPVRLLVLMFWIPASGSDVLMTQTPLSLPVSLGEQASISC<u>RSSQSIEHRNGNT
YLE</u>WYLQKPGQSPKLLIY<u>KVSNRFS</u>GVPDRFSGSGSGTDFTLKISRVEAEDLGVY
YC*FQGSHVPGT*FGGGTNLEIK (SEQ ID NO: 22)

CDR1 (SEQ ID NO: 23) is represented by <u>underlined text</u>; CDR2 (SEQ ID NO: 24) is represented by <u>double-underlined text</u>; CDR3 (SEQ ID NO: 25) is represented by *italicized text*

Figure 37A mAb 260- 6F9F6

Heavy Chain

DNA sequence (423 bp): Leader sequence-FR1-CDR1-FR2-CDR2-FR3-CDR3-FR4

ATGAACTTCGGGTTCAGCTTGATTTTCCTTGTCCTTGTTTTAAAAGGTGTCCAG
TGTGAAGTGAAGCTGGTGGAGTCTGGGGGAGGCTTAGTGAAGCCTGGAGGGT
CCCTGAAAGTCTCCTGTGTTGCCTCT<u>GGATTCACTCTCAGTAACTGTGCCATG
TCTT</u>GGGTTCGCCAGACTCCAGAGAAGAGGCTGGAGTGGGTCGCA<u>TCCATTG
GTAATGGTGATAGCACCTACTATCCAGACAGTGTGAAGGGC</u>CGATTCACCAT
ATCCAGAGATAGTGCCAGGAACATGTTGTTCCTGCAAATGAACAGTCTGAGG
TCTGCGGACACGGCCGTGTATTACTGTGCAAGA*GGCGAAGATTACAACGGTAG
TGATGACTGGTACTTCGATGTC*TGGGGCGCAGGGACCACGGTCACCGTCTCCTC
A (SEQ ID NO: 26)

CDR1 (SEQ ID NO: 27) is represented by <u>underlined text</u>; CDR2 (SEQ ID NO: 27) is represented by <u>double-underlined text</u>; CDR3 (SEQ ID NO: 29) is represented by *italicized text*

Figure 37B mAb 260- 6F9F6

Heavy Chain

Amino Acid sequence (141 AA): Leader sequence-FR1-CDR1-FR2-CDR2-FR3-CDR3-FR4

MNFGFSLIFLVLVLKGVQCEVKLVESGGGLVKPGGSLKVSCVAS<u>GFTLSNCAMS</u>
WVRQTPEKRLEWVA<u>SIGNGDSTYYPDSVKG</u>RFTISRDSARNMLFLQMNSLRSAD
TAVYYCAR*GEDYNGSDDWYFDV*WGAGTTVTVSS (SEQ ID NO: 30)

CDR1 (SEQ ID NO: 31) is represented by <u>underlined text</u>; CDR2 (SEQ ID NO: 32) is represented by <u>double-underlined text</u>; CDR3 (SEQ ID NO: 33) is represented by *italicized text*

Figure 38A mAb 260- 6F9F6

Light Chain

DNA sequence (393 bp): Leader sequence-FR1-CDR1-FR2-CDR2-FR3-CDR3-FR4

ATGAAGTTGCCTGTTAGGCTGTTGGTGCTGATGTTCTGGATTCCTGCTTCCAA
CAGTGATGTTTTGATGACCCAAACTCCACTCTCCCTACCTGTCAGTCTTGGGG
ATCAAGCCTCCATCTCTTGC<u>AGATCTAGTCAGAGCATTGTACTTAGTAATGGA
GATACCTATTTAGAA</u>TGGTACCTACAGAAACCAGGCCAGTCTCCAAAGCTCC
TGATCTAC<u>AAAGTTTCCAATCGATTTCT</u>GGGGTCCCAGACAGGTTCAGTGGC
AGTGGATCAGGGACAGATTTCACACTCAAGATCAGCAGAGTGGAGGCTGAG
GATCTGGGAGTTTATTACTGC*TTTCAAGGTTCACATATTCCTCCGACG*TTCGGTG
GAGGCACCAAGCTGGTAATCAAA (SEQ ID NO: 34)

CDR1 (SEQ ID NO: 35) is represented by underlined text; CDR2 (SEQ ID NO: 36) is represented by double-underlined text; CDR3 (SEQ ID NO: 37) is represented by *italicized text*

Figure38B mAb 260- 6F9F6

Light Chain

Amino Acid sequence (131 AA): Leader sequence-FR1-CDR1-FR2-CDR2-FR3-CDR3-FR4

MKLPVRLLVLMFWIPASNSDVLMTQTPLSLPVSLGDQASISC<u>RSSQSIVLSNGDT
YLE</u>WYLQKPGQSPKLLIY<u>KVSNRFS</u>GVPDRFSGSGSGTDFTLKISRVEAEDLGVY
YC*FQGSHIPPT*FGGGTKLVIK (SEQ ID NO: 38)

CDR1 (SEQ ID NO: 39) is represented by underlined text; CDR2 (SEQ ID NO: 40) is represented by double-underlined text; CDR3 (SEQ ID NO: 41) is represented by *italicized text*

SEQUENCE LISTING

<160> NUMBER OF SEQ ID NOS: 41

<210> SEQ ID NO 1
<211> LENGTH: 97
<212> TYPE: DNA
<213> ORGANISM: Homo sapiens

<400> SEQUENCE: 1
tgctgttgac agtgagcgcg cacatttggc ttacagtaaa tagtgaagcc acagatgtat    60
ttactgtaag ccaaatgtgc ttgcctactg cctcgga                             97

<210> SEQ ID NO 2
<211> LENGTH: 341
<212> TYPE: PRT
<213> ORGANISM: Homo sapiens

<400> SEQUENCE: 2

```
Met Ser Ala Ser Ala Pro Ala Ala Glu Gly Glu Gly Thr Pro Thr Gln
1               5                   10                  15

Pro Ala Ser Glu Lys Glu Pro Glu Met Pro Gly Pro Arg Glu Glu Ser
            20                  25                  30

Glu Glu Glu Glu Asp Glu Asp Asp Glu Glu Glu Glu Glu Glu Glu Lys
        35                  40                  45

Gly Lys Gly Gln Lys Leu Cys Glu Ile Glu Arg Ile His Phe Phe Leu
    50                  55                  60

Ser Lys Lys Lys Thr Asp Glu Leu Arg Asn Leu His Lys Leu Leu Tyr
65                  70                  75                  80

Asn Arg Pro Gly Thr Val Ser Ser Leu Lys Lys Asn Val Gly Gln Phe
                85                  90                  95

Ser Gly Phe Pro Phe Glu Lys Gly Ser Val Gln Tyr Lys Lys Lys Glu
            100                 105                 110

Glu Met Leu Lys Lys Phe Arg Asn Ala Met Leu Lys Ser Ile Cys Glu
            115                 120                 125

Val Leu Asp Leu Glu Arg Ser Gly Val Asn Ser Glu Leu Val Lys Arg
        130                 135                 140

Ile Leu Asn Phe Leu Met His Pro Lys Pro Ser Gly Lys Pro Leu Pro
145                 150                 155                 160

Lys Ser Lys Lys Thr Cys Ser Lys Gly Ser Lys Lys Glu Arg Asn Ser
                165                 170                 175

Ser Gly Met Ala Arg Lys Ala Lys Arg Thr Lys Cys Pro Glu Ile Leu
            180                 185                 190

Ser Asp Glu Ser Ser Asp Glu Asp Glu Lys Lys Asn Lys Glu Glu
        195                 200                 205

Ser Ser Asp Asp Glu Asp Lys Glu Ser Glu Glu Pro Pro Lys Lys
        210                 215                 220

Thr Ala Lys Arg Glu Lys Pro Lys Gln Lys Ala Thr Ser Lys Ser Lys
225                 230                 235                 240

Lys Ser Val Lys Ser Ala Asn Val Lys Lys Ala Asp Ser Ser Thr Thr
                245                 250                 255

Lys Lys Asn Gln Asn Ser Ser Lys Glu Ser Glu Ser Glu Asp Ser
        260                 265                 270

Ser Asp Asp Glu Pro Leu Ile Lys Leu Lys Lys Pro Pro Thr Asp
        275                 280                 285

Glu Glu Leu Lys Glu Thr Ile Lys Leu Leu Ala Ser Ala Asn Leu
        290                 295                 300

Glu Glu Val Thr Met Lys Gln Ile Cys Lys Lys Val Tyr Glu Asn Tyr
305                 310                 315                 320

Pro Thr Tyr Asp Leu Thr Glu Arg Lys Asp Phe Ile Lys Thr Thr Val
                325                 330                 335

Lys Glu Leu Ile Ser
            340

<210> SEQ ID NO 3
<211> LENGTH: 375
<212> TYPE: PRT
<213> ORGANISM: Homo sapiens
```

```
<400> SEQUENCE: 3

Met Ser Ala Ser Ala Pro Ala Ala Glu Gly Glu Gly Thr Pro Thr Gln
1               5                   10                  15

Pro Ala Ser Glu Lys Glu Pro Glu Met Pro Gly Pro Arg Glu Glu Ser
            20                  25                  30

Glu Glu Glu Asp Glu Asp Asp Glu Glu Glu Glu Glu Glu Glu Glu Lys
            35                  40                  45

Glu Lys Ser Leu Ile Val Glu Gly Lys Arg Glu Lys Lys Lys Val Glu
50                  55                  60

Arg Leu Thr Met Gln Val Ser Ser Leu Gln Arg Glu Pro Phe Thr Ile
65                  70                  75                  80

Ala Gln Gly Lys Gly Gln Lys Leu Cys Glu Ile Glu Arg Ile His Phe
                85                  90                  95

Phe Leu Ser Lys Lys Lys Thr Asp Glu Leu Arg Asn Leu His Lys Leu
            100                 105                 110

Leu Tyr Asn Arg Pro Gly Thr Val Ser Ser Leu Lys Lys Asn Val Gly
            115                 120                 125

Gln Phe Ser Gly Phe Pro Phe Glu Lys Gly Ser Val Gln Tyr Lys Lys
            130                 135                 140

Lys Glu Glu Met Leu Lys Lys Phe Arg Asn Ala Met Leu Lys Ser Ile
145                 150                 155                 160

Cys Glu Val Leu Asp Leu Glu Arg Ser Gly Val Asn Ser Glu Leu Val
                165                 170                 175

Lys Arg Ile Leu Asn Phe Leu Met His Pro Lys Pro Ser Gly Lys Pro
            180                 185                 190

Leu Pro Lys Ser Lys Lys Thr Cys Ser Lys Gly Ser Lys Lys Glu Arg
            195                 200                 205

Asn Ser Ser Gly Met Ala Arg Lys Ala Lys Arg Thr Lys Cys Pro Glu
210                 215                 220

Ile Leu Ser Asp Glu Ser Ser Asp Glu Asp Glu Lys Lys Asn Lys
225                 230                 235                 240

Glu Glu Ser Ser Asp Asp Glu Asp Lys Glu Ser Glu Glu Glu Pro Pro
            245                 250                 255

Lys Lys Thr Ala Lys Arg Glu Lys Pro Lys Gln Lys Ala Thr Ser Lys
            260                 265                 270

Ser Lys Lys Ser Val Lys Ser Ala Asn Val Lys Lys Ala Asp Ser Ser
            275                 280                 285

Thr Thr Lys Lys Asn Gln Asn Ser Ser Lys Lys Glu Ser Glu Ser Glu
290                 295                 300

Asp Ser Ser Asp Asp Glu Pro Leu Ile Lys Lys Leu Lys Lys Pro Pro
305                 310                 315                 320

Thr Asp Glu Glu Leu Lys Glu Thr Ile Lys Lys Leu Leu Ala Ser Ala
                325                 330                 335

Asn Leu Glu Glu Val Thr Met Lys Gln Ile Cys Lys Lys Val Tyr Glu
            340                 345                 350

Asn Tyr Pro Thr Tyr Asp Leu Thr Glu Arg Lys Asp Phe Ile Lys Thr
            355                 360                 365

Thr Val Lys Glu Leu Ile Ser
            370                 375

<210> SEQ ID NO 4
<211> LENGTH: 36
<212> TYPE: PRT
<213> ORGANISM: Homo sapiens
```

```
<400> SEQUENCE: 4

Cys Gln Pro Ala Ser Glu Lys Glu Pro Glu Met Pro Gly Pro Arg Glu
1               5                   10                  15

Glu Ser Glu Glu Glu Glu Asp Glu Asp Asp Glu Glu Glu Glu Glu Glu
                20                  25                  30

Glu Lys Gly Lys
        35

<210> SEQ ID NO 5
<211> LENGTH: 42
<212> TYPE: PRT
<213> ORGANISM: Homo sapiens

<400> SEQUENCE: 5

Gln Asn Ser Ser Lys Lys Glu Ser Glu Ser Glu Asp Ser Ser Asp Asp
1               5                   10                  15

Glu Pro Leu Ile Lys Lys Leu Lys Lys Pro Pro Thr Asp Glu Glu Leu
                20                  25                  30

Lys Glu Thr Ile Lys Lys Leu Leu Ala Cys
        35                  40

<210> SEQ ID NO 6
<211> LENGTH: 35
<212> TYPE: PRT
<213> ORGANISM: Homo sapiens

<400> SEQUENCE: 6

Glu Glu Ser Ser Asp Asp Glu Asp Lys Glu Ser Glu Glu Glu Pro Pro
1               5                   10                  15

Lys Lys Thr Ala Lys Arg Glu Lys Pro Lys Gln Lys Ala Thr Ser Lys
                20                  25                  30

Ser Lys Cys
        35

<210> SEQ ID NO 7
<211> LENGTH: 42
<212> TYPE: PRT
<213> ORGANISM: Homo sapiens

<400> SEQUENCE: 7

Cys Ser Ala Asn Leu Glu Glu Val Thr Met Lys Gln Ile Cys Lys Lys
1               5                   10                  15

Val Tyr Glu Asn Tyr Pro Thr Tyr Asp Leu Thr Glu Arg Lys Asp Phe
                20                  25                  30

Ile Lys Thr Thr Val Lys Glu Leu Ile Ser
        35                  40

<210> SEQ ID NO 8
<211> LENGTH: 15
<212> TYPE: PRT
<213> ORGANISM: Homo sapiens

<400> SEQUENCE: 8

Cys Leu Pro Lys Ser Lys Lys Thr Cys Ser Lys Gly Ser Lys Lys
1               5                   10                  15

<210> SEQ ID NO 9
<211> LENGTH: 15
<212> TYPE: PRT
<213> ORGANISM: Homo sapiens
```

<400> SEQUENCE: 9

Cys Glu Arg Asn Ser Ser Gly Met Ala Arg Lys Ala Lys Arg Thr
1               5                   10                  15

<210> SEQ ID NO 10
<211> LENGTH: 408
<212> TYPE: DNA
<213> ORGANISM: Homo sapiens

<400> SEQUENCE: 10

```
atgatggtgt taagtcttct gttcctgttg acagcccttc cgggtatcct gtcagaggtg    60
cagcttcagg agtcaggacc tagcctcgtg aaaccttctc agactctgtc cctcacctgt   120
tctgtcactg gcgactccat caccagtggt tactggaact ggatccggaa attcccaggg   180
aataaacttg agtacatggg gtatataagt tacagtggtg acacttacta caatccatct   240
ctcaaaagtc gattctccat cactcgagac acatccaaga accagttcta cctgcaattg   300
aattctgtga ctactgagga cacagccaca tattactgtg cagccattac tatggctact   360
cttgctatgg actactgggg tcaaggaacc tcagtcaccg tctcctca              408
```

<210> SEQ ID NO 11
<211> LENGTH: 30
<212> TYPE: DNA
<213> ORGANISM: Homo sapiens

<400> SEQUENCE: 11

```
ggcgactcca tcaccagtgg ttactggaac                                     30
```

<210> SEQ ID NO 12
<211> LENGTH: 48
<212> TYPE: DNA
<213> ORGANISM: Homo sapiens

<400> SEQUENCE: 12

```
tatataagtt acagtggtga cacttactac aatccatctc tcaaaagt                 48
```

<210> SEQ ID NO 13
<211> LENGTH: 30
<212> TYPE: DNA
<213> ORGANISM: Homo sapiens

<400> SEQUENCE: 13

```
attactatgg ctactcttgc tatggactac                                     30
```

<210> SEQ ID NO 14
<211> LENGTH: 136
<212> TYPE: PRT
<213> ORGANISM: Homo sapiens

<400> SEQUENCE: 14

Met Met Val Leu Ser Leu Leu Phe Leu Leu Thr Ala Leu Pro Gly Ile
1               5                   10                  15

Leu Ser Glu Val Gln Leu Gln Glu Ser Gly Pro Ser Leu Val Lys Pro
                20                  25                  30

Ser Gln Thr Leu Ser Leu Thr Cys Ser Val Thr Gly Asp Ser Ile Thr
            35                  40                  45

Ser Gly Tyr Trp Asn Trp Ile Arg Lys Phe Pro Gly Asn Lys Leu Glu
        50                  55                  60

Tyr Met Gly Tyr Ile Ser Tyr Ser Gly Asp Thr Tyr Tyr Asn Pro Ser
65                  70                  75                  80

```
        Leu Lys Ser Arg Phe Ser Ile Thr Arg Asp Thr Ser Lys Asn Gln Phe
                    85                  90                  95

Tyr Leu Gln Leu Asn Ser Val Thr Thr Glu Asp Thr Ala Thr Tyr Tyr
                100                 105                 110

Cys Ala Ala Ile Thr Met Ala Thr Leu Ala Met Asp Tyr Trp Gly Gln
                    115                 120                 125

Gly Thr Ser Val Thr Val Ser Ser
            130                 135

<210> SEQ ID NO 15
<211> LENGTH: 10
<212> TYPE: PRT
<213> ORGANISM: Homo sapiens

<400> SEQUENCE: 15

Gly Asp Ser Ile Thr Ser Gly Tyr Trp Asn
1               5                   10

<210> SEQ ID NO 16
<211> LENGTH: 16
<212> TYPE: PRT
<213> ORGANISM: Homo sapiens

<400> SEQUENCE: 16

Tyr Ile Ser Tyr Ser Gly Asp Thr Tyr Tyr Asn Pro Ser Leu Lys Ser
1               5                   10                  15

<210> SEQ ID NO 17
<211> LENGTH: 10
<212> TYPE: PRT
<213> ORGANISM: Homo sapiens

<400> SEQUENCE: 17

Ile Thr Met Ala Thr Leu Ala Met Asp Tyr
1               5                   10

<210> SEQ ID NO 18
<211> LENGTH: 393
<212> TYPE: DNA
<213> ORGANISM: Homo sapiens

<400> SEQUENCE: 18
atgaagttgc ctgttaggct gttggtgctg atgttctgga ttcctgcttc cggcagtgat      60
gttttgatga cccaaactcc actctccctg cctgtcagtc ttggagagca ggcctccatc     120
tcttgtagat ctagtcagag cattgaacat cggaatggaa acacctattt agaatggtac     180
ctgcagaaac caggccagtc tccaaaactc ctgatctaca agtttccaa ccgattctct     240 ggggtcccag acaggttcag tggcagtgga tcagggacag atttcacact caagatcagc     300
agagtggagg ctgaggatct gggagtttat tactgctttc aaggttcaca tgttcctggg     360
acgttcggtg gaggcaccaa cctggaaatc aaa                                  393

<210> SEQ ID NO 19
<211> LENGTH: 48
<212> TYPE: DNA
<213> ORGANISM: Homo sapiens

<400> SEQUENCE: 19
agatctagtc agagcattga acatcggaat ggaaacacct atttagaa                   48
```

<210> SEQ ID NO 20
<211> LENGTH: 21
<212> TYPE: DNA
<213> ORGANISM: Homo sapiens

<400> SEQUENCE: 20
aaagtttcca accgattctc t                                              21

<210> SEQ ID NO 21
<211> LENGTH: 27
<212> TYPE: DNA
<213> ORGANISM: Homo sapiens

<400> SEQUENCE: 21
tttcaaggtt cacatgttcc tgggacg                                        27

<210> SEQ ID NO 22
<211> LENGTH: 131
<212> TYPE: PRT
<213> ORGANISM: Homo sapiens

<400> SEQUENCE: 22

Met Lys Leu Pro Val Arg Leu Val Leu Met Phe Trp Ile Pro Ala
1               5                   10                  15

Ser Gly Ser Asp Val Leu Met Thr Gln Thr Pro Leu Ser Leu Pro Val
                20                  25                  30

Ser Leu Gly Glu Gln Ala Ser Ile Ser Cys Arg Ser Ser Gln Ser Ile
            35                  40                  45

Glu His Arg Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Gly Thr Phe Gly Gly Gly Thr Asn Leu
        115                 120                 125

Glu Ile Lys
        130

<210> SEQ ID NO 23
<211> LENGTH: 16
<212> TYPE: PRT
<213> ORGANISM: Homo sapiens

<400> SEQUENCE: 23

Arg Ser Ser Gln Ser Ile Glu His Arg Asn Gly Asn Thr Tyr Leu Glu
1               5                   10                  15

<210> SEQ ID NO 24
<211> LENGTH: 7
<212> TYPE: PRT
<213> ORGANISM: Homo sapiens

<400> SEQUENCE: 24

Lys Val Ser Asn Arg Phe Ser
1               5

<210> SEQ ID NO 25
<211> LENGTH: 9
<212> TYPE: PRT
<213> ORGANISM: Homo sapiens

<400> SEQUENCE: 25

Phe Gln Gly Ser His Val Pro Gly Thr
1               5

<210> SEQ ID NO 26
<211> LENGTH: 423
<212> TYPE: DNA
<213> ORGANISM: Homo sapiens

<400> SEQUENCE: 26

```
atgaacttcg ggttcagctt gattttcctt gtccttgttt taaaaggtgt ccagtgtgaa      60
gtgaagctgg tggagtctgg gggaggctta gtgaagcctg agggtccct gaaagtctcc      120
tgtgttgcct ctggattcac tctcagtaac tgtgccatgt cttgggttcg ccagactcca     180
gagaagaggc tggagtgggt cgcatccatt ggtaatggta tagcaccta ctatccagac     240
agtgtgaagg gccgattcac catatccaga gatagtgcca ggaacatgtt gttcctgcaa     300
atgaacagtc tgaggtctgc ggacacggcc gtgtattact gtgcaagagg cgaagattac    360
aacggtagtg atgactggta cttcgatgtc tggggcgcag ggaccacggt caccgtctcc     420
tca                                                                  423
```

<210> SEQ ID NO 27
<211> LENGTH: 30
<212> TYPE: DNA
<213> ORGANISM: Homo sapiens

<400> SEQUENCE: 27

```
ggattcactc tcagtaactg tgccatgtct                                      30
```

<210> SEQ ID NO 28
<211> LENGTH: 48
<212> TYPE: DNA
<213> ORGANISM: Homo sapiens

<400> SEQUENCE: 28

```
tccattggta atggtgatag cacctactat ccagacagtg tgaagggc                  48
```

<210> SEQ ID NO 29
<211> LENGTH: 42
<212> TYPE: DNA
<213> ORGANISM: Homo sapiens

<400> SEQUENCE: 29

```
ggcgaagatt acaacggtag tgatgactgg tacttcgatg tc                        42
```

<210> SEQ ID NO 30
<211> LENGTH: 141
<212> TYPE: PRT
<213> ORGANISM: Homo sapiens

<400> SEQUENCE: 30

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

```
Pro Gly Gly Ser Leu Lys Val Ser Cys Val Ala Ser Gly Phe Thr Leu
         35                  40                  45

Ser Asn Cys Ala Met Ser Trp Val Arg Gln Thr Pro Glu Lys Arg Leu
 50                  55                  60

Glu Trp Val Ala Ser Ile Gly Asn Gly Asp Ser Thr Tyr Tyr Pro Asp
 65                  70                  75                  80

Ser Val Lys Gly Arg Phe Thr Ile Ser Arg Asp Ser Ala Arg Asn Met
                 85                  90                  95

Leu Phe Leu Gln Met Asn Ser Leu Arg Ser Ala Asp Thr Ala Val Tyr
                100                 105                 110

Tyr Cys Ala Arg Gly Glu Asp Tyr Asn Gly Ser Asp Asp Trp Tyr Phe
                115                 120                 125

Asp Val Trp Gly Ala Gly Thr Thr Val Thr Val Ser Ser
                130                 135                 140

<210> SEQ ID NO 31
<211> LENGTH: 10
<212> TYPE: PRT
<213> ORGANISM: Homo sapiens

<400> SEQUENCE: 31

Gly Phe Thr Leu Ser Asn Cys Ala Met Ser
1               5                   10

<210> SEQ ID NO 32
<211> LENGTH: 16
<212> TYPE: PRT
<213> ORGANISM: Homo sapiens

<400> SEQUENCE: 32

Ser Ile Gly Asn Gly Asp Ser Thr Tyr Tyr Pro Asp Ser Val Lys Gly
1               5                   10                  15

<210> SEQ ID NO 33
<211> LENGTH: 14
<212> TYPE: PRT
<213> ORGANISM: Homo sapiens

<400> SEQUENCE: 33

Gly Glu Asp Tyr Asn Gly Ser Asp Asp Trp Tyr Phe Asp Val
1               5                   10

<210> SEQ ID NO 34
<211> LENGTH: 393
<212> TYPE: DNA
<213> ORGANISM: Homo sapiens

<400> SEQUENCE: 34
atgaagttgc ctgttaggct gttggtgctg atgttctgga ttcctgcttc caacagtgat      60
gttttgatga cccaaactcc actctcccta cctgtcagtc ttggggatca agcctccatc     120
tcttgcagat ctagtcagag cattgtactt agtaatggag atacctattt gaatggtac     180 ctacagaaac caggccagtc tccaaagctc ctgatctaca aagtttccaa tcgattttct     240
ggggtcccag acaggttcag tggcagtgga tcagggacag atttcacact caagatcagc     300
agagtggagg ctgaggatct gggagtttat tactgctttc aaggttcaca tattcctccg     360
acgttcggtg gaggcaccaa gctggtaatc aaa                                   393
```

<210> SEQ ID NO 35
<211> LENGTH: 48
<212> TYPE: DNA
<213> ORGANISM: Homo sapiens

<400> SEQUENCE: 35
agatctagtc agagcattgt acttagtaat ggagatacct atttagaa                48

<210> SEQ ID NO 36
<211> LENGTH: 21
<212> TYPE: DNA
<213> ORGANISM: Homo sapiens

<400> SEQUENCE: 36
aaagtttcca atcgattttc t                                              21

<210> SEQ ID NO 37
<211> LENGTH: 27
<212> TYPE: DNA
<213> ORGANISM: Homo sapiens

<400> SEQUENCE: 37
tttcaaggtt cacatattcc tccgacg                                        27

<210> SEQ ID NO 38
<211> LENGTH: 131
<212> TYPE: PRT
<213> ORGANISM: Homo sapiens

<400> SEQUENCE: 38

Met Lys Leu Pro Val Arg Leu Leu Val Leu Met Phe Trp Ile Pro Ala
1               5                   10                  15

Ser Asn Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val Leu Ser Asn Gly Asp Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Ile Pro Pro Thr Phe Gly Gly Gly Thr Lys Leu
        115                 120                 125

Val Ile Lys
    130

<210> SEQ ID NO 39
<211> LENGTH: 16
<212> TYPE: PRT
<213> ORGANISM: Homo sapiens

<400> SEQUENCE: 39

Arg Ser Ser Gln Ser Ile Val Leu Ser Asn Gly Asp Thr Tyr Leu Glu
1               5                   10                  15

```
<210> SEQ ID NO 40
<211> LENGTH: 7
<212> TYPE: PRT
<213> ORGANISM: Homo sapiens

<400> SEQUENCE: 40

Lys Val Ser Asn Arg Phe Ser
1               5

<210> SEQ ID NO 41
<211> LENGTH: 9
<212> TYPE: PRT
<213> ORGANISM: Homo sapiens

<400> SEQUENCE: 41

Phe Gln Gly Ser His Ile Pro Pro Thr
1               5
```

ELISA DETECTION OF URINE DEK TO PREDICT AND DIAGNOSE BLADDER CANCER IN HUMANS

CROSS-REFERENCE TO RELATED APPLICATIONS

The present application is a continuation of U.S. application Ser. No. 14/939,031, filed on Nov. 12, 2015, which is a continuation of U.S. application Ser. No. 14/258,122, filed on Apr. 22, 2014, which is a Continuation-In-Part (CIP) of U.S. Pat. No. 8,741,582, filed Oct. 20, 2011, which claims the benefit of priority under 35 U.S.C. § 119(e) to U.S. Provisional Application Nos. 61/455,406 filed Oct. 20, 2010 and 61/455,405 filed Oct. 20, 2010, the disclosures of which are hereby incorporated by reference in their entireties.

REFERENCE TO AN ELECTRONIC SEQUENCE LISTING

The contents of the electronic sequence listing named SEQUENCE LISTING (Text Size 20 KB; Date of Creation Oct. 24, 2019) is herein incorporated by reference in its entirety.

FIELD OF INVENTION

The present invention generally relates to a method of detecting a DEK protein in a urine sample. Specifically, the present invention relates to a method of detecting and diagnosing bladder cancer in humans by ELISA to detect DEK in human urine. The ELISA utilizes a first monoclonal antibody to capture DEK and a second monoclonal antibody to detect DEK to provide a high sensitivity assay (i.e., limit of detection <50 ng/mL). The present ELISA method permits a quantitative correlation between the presence of a DEK protein in urine with occurrence of bladder cancer in humans.

BACKGROUND OF THE INVENTION

Bladder cancer is a prevalent malignancy in the United States. In 2010, approximately 70,000 newly diagnosed cases of bladder cancer are expected; of those, more than 14,000 are expected to die. According to the American Cancer Society, the five-year survival rate for patients diagnosed with bladder cancer is 98% at stage 0, 88% at stage I, 63% at stage II, 46% at stage III, and 15% at stage IV. These bleak statistics highlight the fact that early detection of bladder cancer is critical for the intervention of the disease. The estimated overall cost per patient from diagnosis of bladder cancer to death is about US $96,000-$187,000; and the total cost amounts to US $3.7 billion.

Early detection of bladder cancer is essential for removing the tumor with preservation of the bladder, avoiding local complications from the tumor such as bleeding or infections, avoiding metastasis and hence improving prognosis and long-term survival. In bladder cancer, ~90% are transitional cell carcinomas, ~5% are squamous cell carcinomas, and ~2% are adenocarcinomas. Of the transitional cell carcinomas, ~75% present as superficial tumors; of which ~50-70% will recur and ~10-20% will progress to invasive bladder tumors. Patients are therefore kept under surveillance for early detection of recurrences.

The current standard methods to detect bladder cancer include cystoscopy and urine cytology. Cystoscopy involves inserting a thin, lighted scope through the patient's urethra into the bladder. It is invasive, unpleasant, and expensive, which in turn leads to poor patient compliance. In addition, cystoscopy often yields false-positive results. Urine cytology is an alternative procedure that involves checking the number and appearance of cells in a urine sample. It has a low sensitivity for detecting small or low-grade bladder tumors.

Numerous urine-based markers have been tested for bladder cancer detection and surveillance. These markers include complement factor H (BTA-Stat/TRAK), nuclear matrix proteins (NMP22), mucin-like antigens, hyaluronic acid, hyaluronidase, survivin, soluble Fas, telomerase and detection of chromosomal aneuploidy and deletion using fluorescence in situ hybridization (UroVysion®). However, none have acceptable sensitivity and specificity as a routine tool for bladder cancer diagnostics and surveillance.

Accordingly, there remains a continuing need for a urine-based test with adequate sensitivity and specificity in the detection and diagnosis of bladder cancer in humans. It would be advantageous to develop a non-invasive and reliable screening method that encourages initial and follow-up screening. The present invention cures all the prior art deficiencies and provides a novel method of detecting DEK protein in urine. The present method provides a high sensitivity and specificity, and can be used as a diagnostic tool to detect bladder cancer in humans.

SUMMARY OF INVENTION

In one aspect, the present invention provides a method of detecting DEK in a urine sample of a human, comprising the steps of: (a) forming a precipitate from a urine sample with a chemical compound selected from the group consisting of acetone, trichloroacetic acid, ethanol, methanol/chloroform, and ammonium sulfate; (b) re-suspending said precipitate in a polar solvent to form a solution, said solution has a final volume that is 10-50 fold less than that of said urine sample; (c) concentrating said solution 2-10 fold by filtration; and (d) detecting DEK in said concentrated solution using an anti-DEK antibody in a Western blot assay.

Preferably, the chemical compound is acetone, methanol/chloroform, or trichloroacetic acid, or acetone. Preferably, the chemical compound and urine sample has a volume to volume ratio of 10:1. More preferably, the chemical compound and urine sample has a volume to volume ratio of 5:1 or 2:1.

Preferably, the polar solvent is tri-ethanol amine. Preferably, the solution in step (b) has a final volume of 15-40 fold less than that of urine sample. Preferably, the solution in step (b) has a final volume of 20 fold less than that of urine sample. More preferably, the concentrated solution in step (c) has a final volume of 5 fold less than that of re-suspended solution.

Preferably, the filtration is performed using a filter that has 3 kD cutoff. The anti-DEK antibody is a monoclonal antibody or a polyclonal antibody. The anti-DEK protein is labeled with horse radish peroxidase.

In another aspect, the present invention provides a method of detecting bladder cancer in a human, comprising the steps of: (a) obtaining a urine sample from a human; (b) forming a precipitate from said urine sample with a chemical compound selected from the group consisting of acetone, trichloroacetic acid, ethanol and ammonium sulfate; (c) re-suspending said precipitate in a polar solvent to form a solution, said solution has a final volume that is 10-50 fold less than that of urine sample; (d) concentrating said solution 2-10 fold by filtration; and (e) detecting DEK in said concentrated solution using an anti-DEK antibody in a Western blot assay, wherein the presence of DEK protein in said urine sample is an indicative of a bladder cancer in said human.

Preferably, the bladder cancer is a transitional cell carcinoma.

In yet another aspect, the present invention provides a kit for detecting bladder cancer in a human, comprising: (a) a container for a urine sample; (b) a chemical compound, wherein said chemical compound induces the formation of a precipitate from said urine sample; (c) a polar solvent; (d) a filter with a 3 kD cutoff, and (e) an instruction for the use of said chemical and said filter in preparing said urine sample to allow detection of DEK protein by Western blot assay.

In one aspect, the present invention provides a method of detecting DEK isoform 2 protein in a urine sample of a human, comprising the steps of: (a) concentrating a urine sample, said urine sample is suspected of containing DEK isoform 2 protein; (b) immobilizing said concentrated urine sample onto a solid surface; (c) adding an anti-DEK antibody to said immobilized concentrated urine sample so as to allow a complex formation between DEK isoform 2 protein and said anti-DEK antibody, wherein said anti-DEK antibody recognizes DEK isoform 2 protein; and (d) detecting said protein-antibody complex.

Preferably, the concentrating step is performed by filtration-induced concentration of urine. Preferably, the concentrated urine sample is at least 20 fold concentrated as compared to neat urine. More preferably, the concentrated urine sample is at least 30 fold concentrated as compared to neat urine.

Preferably, the anti-DEK antibody is a monoclonal antibody or a polyclonal antibody. Preferably, the anti-DEK protein is labeled with horse-radish peroxidase.

In another aspect, the present invention provides a method of detecting bladder cancer in a human, comprising the steps of: (a) obtaining a urine sample from a human suspected of suffering from bladder cancer; (b) concentrating said urine sample; (c) immobilizing said concentrated urine sample onto a solid surface; (d) adding an anti-DEK antibody to said immobilized concentrated urine sample so as to allow a complex formation between DEK isoform 2 protein and said anti-DEK antibody, wherein said anti-DEK antibody recognizes DEK isoform 2 protein; and (e) detecting said protein-antibody complex, wherein the presence of said protein-antibody complex is indicative of a bladder cancer in said human.

In yet another aspect, the present invention provides a method of detecting DEK isoform 2 protein in a urine sample of a human, comprising the steps of:
(a) concentrating a urine sample, said urine sample is suspected of containing DEK isoform 2 protein; (b) immobilizing a first anti-DEK antibody onto a solid surface;
(c) adding said concentrated urine sample onto said solid surface having said immobilized first anti-DEK antibody and allowing formation of DEK isoform 2 protein and first anti-DEK antibody complex; (d) removing unbound DEK isoform 2 protein;
(e) adding a second anti-DEK antibody so as to allow formation of a complex between said bound DEK isoform 2 protein with said second anti-DEK antibody; and (f) detecting said bound DEK isoform 2 protein with said second anti-DEK antibody complex, wherein said first anti-DEK antibody and said second anti-DEK antibody recognize a different region of DEK isoform 2 protein.

In another aspect, the present invention provides a method of detecting bladder cancer in a human, comprising the steps of: (a) obtaining a urine sample from a human suspected of suffering from bladder cancer; (b) concentrating said urine sample; (c) immobilizing a first anti-DEK antibody onto a solid surface; (d) adding said concentrated urine sample onto said solid surface having said immobilized first anti-DEK antibody and allowing formation of DEK isoform 2 protein and first anti-DEK antibody complex; (e) removing unbound DEK isoform 2 protein; (f) adding a second anti-DEK antibody so as to allow formation of a complex between said bound DEK isoform 2 protein with said second anti-DEK antibody; and (g) detecting said bound DEK isoform 2 protein with said second anti-DEK antibody complex, wherein said first anti-DEK antibody and said second anti-DEK antibody recognize a different region of DEK isoform 2 protein, and wherein the presence of said protein-antibody complex is indicative of a bladder cancer in said human.

In yet another aspect, the present invention provides a kit for detecting bladder cancer in a human, comprising: (a) a container for a urine sample; (b) anti-DEK antibody, the anti-DEK antibody recognizes DEK isoform 2 protein; (c) an instruction for the use of said antibody in detecting DEK isoform 2 protein in an ELISA.

Preferably, the kit further comprises a microtiter plate. Preferably, the kit further comprises a detection reagent. Preferably, the kit further comprises an additional anti-DEK antibody, the additional anti-DEK-antibody also recognizes DEK isoform 2, but with a recognition site differs from that of said anti-DEK antibody.

In yet another aspect, the present invention provides a method of detecting DEK isoform 2 protein in a urine sample of a human, comprising the steps of:
(a) providing a neat urine sample, said urine sample is suspected of containing DEK isoform 2 protein; (b) immobilizing a first anti-DEK monoclonal antibody onto a solid surface; (c) adding said neat urine sample onto said solid surface having said immobilized first anti-DEK monoclonal antibody and allowing formation of DEK isoform 2 protein and first anti-DEK antibody complex; (d) removing unbound DEK isoform 2 protein; (e) adding a second anti-DEK monoclonal antibody so as to allow formation of a complex between said bound DEK isoform 2 protein with said second anti-DEK monoclonal antibody; and (f) detecting said bound DEK isoform 2 protein with said second anti-DEK monoclonal antibody complex, wherein said first anti-DEK monoclonal antibody and said second anti-DEK monoclonal antibody recognize a different region of DEK isoform 2 protein (SEQ ID NO: 2)

In another aspect, the present invention provides a method of detecting bladder cancer in a human, comprising the steps of: (a) obtaining a urine sample from a human suspected of suffering from bladder cancer; (b) immobilizing a first anti-DEK monoclonal antibody onto a solid surface; (d) adding said urine sample onto said solid surface having said immobilized first anti-DEK monoclonal antibody and allowing formation of DEK isoform 2 protein and first anti-DEK monoclonal antibody complex; (e) removing unbound DEK isoform 2 protein; (f) adding a second anti-DEK monoclonal antibody so as to allow formation of a complex between said bound DEK isoform 2 protein with said second anti-DEK monoclonal antibody; and (g) detecting said bound DEK isoform 2 protein with said second anti-DEK antibody complex, wherein said first anti-DEK monoclonal antibody and said second anti-DEK monoclonal antibody recognize a different region of DEK isoform 2 protein, and wherein the presence of said protein-antibody complex is indicative of a bladder cancer in said human.

In one aspect, the present invention provides an isolated monoclonal antibody (mAb 16-2C9C3), said mAb 16-2C9C3 comprises: (i) CDR1 of the heavy chain variable region which has the amino acid sequence of SEQ ID NO:15; (ii) CDR2 of the heavy chain variable region which has the amino acid sequence of SEQ ID NO:16; (iii) CDR3 of the heavy chain variable region which has the amino acid sequence of SEQ ID NO:17; (iv) CDR1 of the light chain variable region which has an amino acid sequence of SEQ ID NO: 23; (v) CDR2 of the light chain variable region which has the amino acid sequence of SEQ ID NO:24; and (vi) CDR3 of the light chain variable region which has the amino acid sequence of SEQ ID NO:25.

In another aspect, the present invention provides an isolated monoclonal antibody (mAb 260-6F9F6), said mAb 260-6F9F6 comprises: (i) CDR1 of the heavy chain variable region which has the amino acid sequence of SEQ ID NO:31; (ii) CDR2 of the heavy chain variable region which has the amino acid sequence of SEQ ID NO:32; (iii) CDR3 of the heavy chain variable region which has the amino acid sequence of SEQ ID NO:33; (iv) CDR1 of the light chain variable region which has an amino acid sequence of SEQ ID NO: 39; (v) CDR2 of the light chain variable region which has the amino acid sequence of SEQ ID NO:40; and (vi) CDR3 of the light chain variable region which has the amino acid sequence of SEQ ID NO:41.

In another aspect, the present invention provides a kit for detecting bladder cancer in a human, comprising: (a) the isolated monoclonal antibody of mAb 16-2C9C3; and (b) an instruction for the use of said monoclonal antibody in detecting DEK protein present in urine in an ELISA. Preferably, the kit further comprises the isolated monoclonal antibody of mAb 260-6F9F6. The kit may further comprises a microtiter plate, or a detection reagent. Preferably, the kit contains mAb 16-2C9C3 and mAb 260-6F9F6. The instruction provides guidance for using (i) mAb 16-2C9C3 as a capture antibody, and (ii) mAb 260-6F9F6 as a detection antibody, for the purpose of binding DEK protein present in a urine sample to said capture antibody to form an immunological complex and (iii) detecting the formation of said immunological complex, such that the presence or absence of the immunological complex is indicative of the presence or absence of bladder cancer in a human.

In yet another aspect, the present invention provides a method of detecting bladder cancer in a human, comprising the steps of: (a) providing a urine sample (neat urine) from a human suspected of suffering from bladder cancer; (b) immobilizing the antibody mAb 16-2C9C3 onto a solid surface; (c) adding said urine sample onto said solid surface to allow DEK protein present in said urine to be captured onto said solid surface; (d) washing the solid surface to remove unbound DEK protein; (e) adding the antibody mAb 260-6F9F6 so as to allow formation of a complex between said captured DEK protein with said antibody mAb 260-6F9F6; and (f) detecting said complex, wherein the presence of said complex is indicative of the presence of DEK in said urine and whereby detect the occurrence of bladder cancer in said human.

BRIEF DESCRIPTION OF THE DRAWINGS

FIGS. 30A-30B depict the detection of DEK in DEK spiked urine and DEK spiked PBS using a DEK sandwich ELISA.

FIG. 30A specifically depicts graphical representations of the results of 300 µl of various DEK concentrations were spiked into urine and were analyzed by DEK sandwich ELISA. rDEK was detected in spiked DEK neat urine with a sensitivity of ~4 ng/ml.

FIG. 30B specifically depicts graphical representations of the results of 300 µl of various DEK concentrations were spiked into PBS were analyzed by DEK sandwich ELISA. rDEK was detected in spiked DEK PBS with a sensitivity of ~2 ng/ml.

2C9C3, is immobilized on an ELISA plate followed by the addition of urine containing the DEK protein. The captured DEK antigen is detected by the detection antibody, mAb260-6F9F6, using an HRP linked strepavidin antibody (SA antibody) and TMB as the substrate, the complex is detected by reading absorbance at 450 nm.

Figure 32:
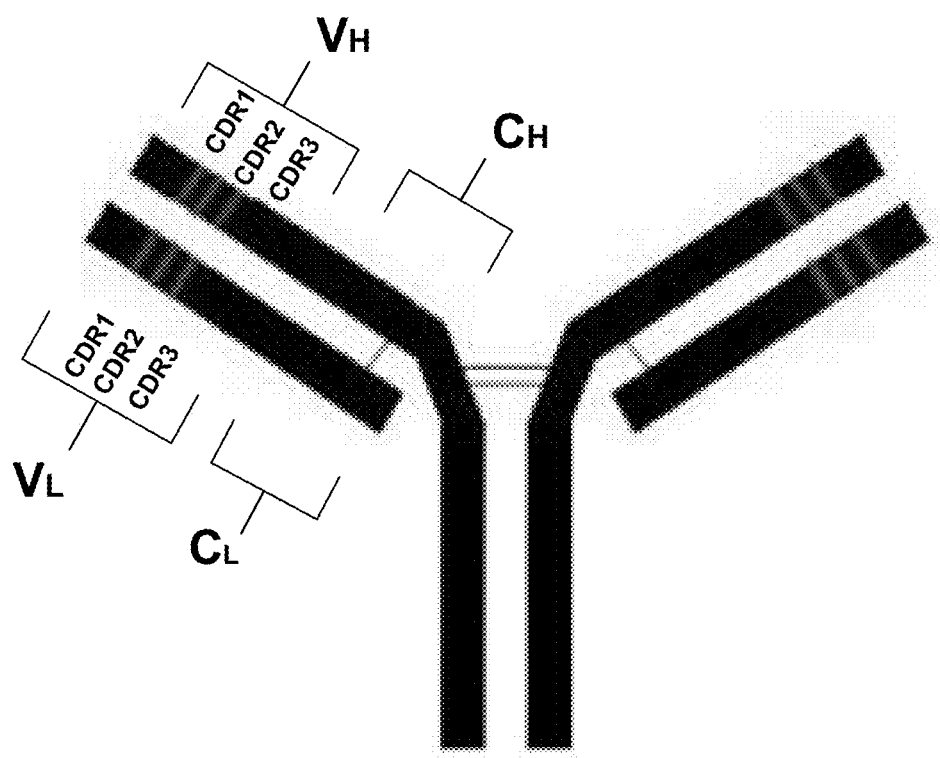

FIG. 32 depicts the diagrammatical representation of the location of CDR's (Complementarity Determining Regions) within the variable and constant regions. The light chain of variable and constant regions is designated as $V_L$ and $C_L$, respectively, and the heavy chain of variable and constant regions is designated as $V_H$ and $C_H$, respectively. In total, there are 6 different CDR sequences present in an antibody.

FIG. 33A depicts the graphical representations of the distribution concentration of DEK protein in ng/mL in the urine of bladder cancer patients and control group. 300 µl of neat urine from patients with bladder cancer and control group (healthy individuals and patients with other non-bladder cancer diseases) was analyzed by DEK sandwich ELISA. The absorbance reading was plotted on a standard curve to determine the concentration of DEK in the urine of tested samples in the two groups (TCC and Control).

FIG. 33B depicts the graphical representations of the distribution of absorbance readings of the urine samples in the two groups (TCC and Control) tested by the developed DEK Sandwich ELISA. 300 µl of neat urine from patients with bladder cancer and control group (healthy individuals and patients with other non bladder cancer diseases) was analyzed by DEK sandwich ELISA.

FIG. 33C depicts the receiver operating characteristic (ROC) analysis of clinical samples comprising of TCC and control group. The ELISA assay detects the DEK protein in bladder cancer patients with a sensitivity of 82.3% and specificity of 70.58%. The assay has a positive predictive rate (PPV) of 75% and a negative predictive value of 84.6%

Figure 34:
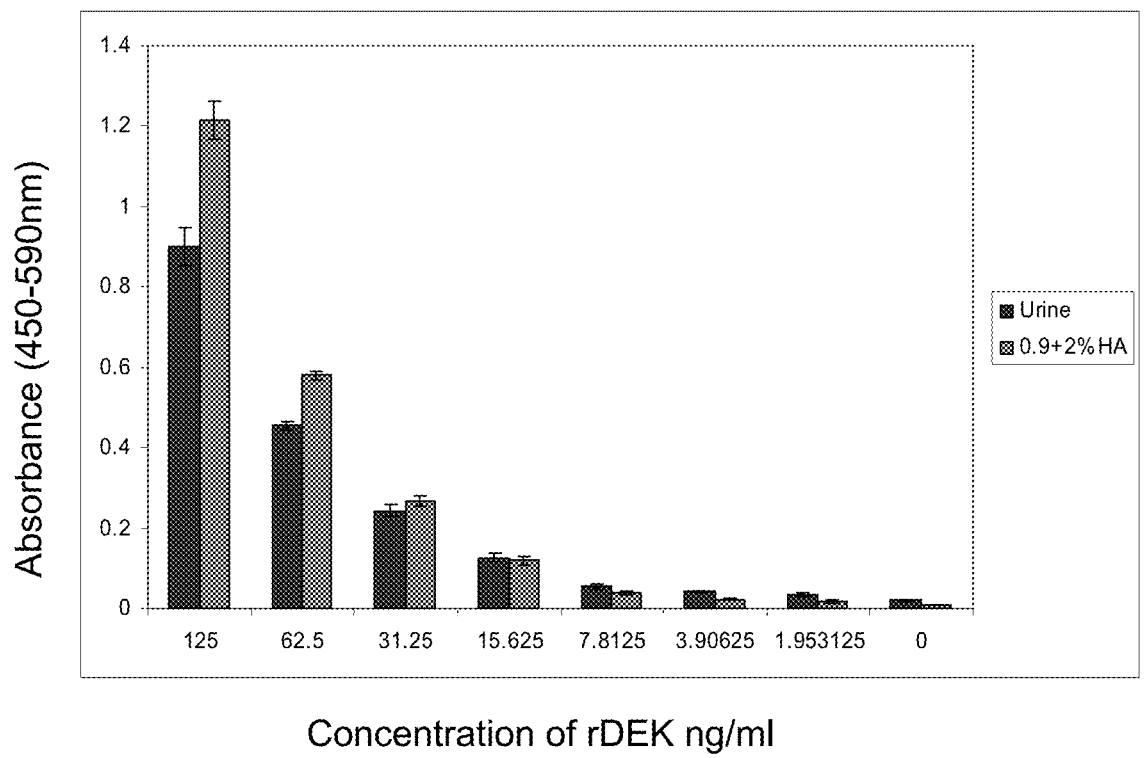

FIG. 34 depicts a graphical representation of the similarity of synthetic urine and healthy urine by using the DEK sandwich ELISA. Recombinant DEK (rDEK) was spiked into synthetic urine and into healthy urine samples and was then analyzed using the DEK sandwich ELISA. rDEK spiked synthetic urine and healthy urine samples had similar assay sensitivity.

FIG. 35A depicts the nucleotide sequence for the heavy chain of mAb 16-2C9C3, including CDRs 1-3.

FIG. 35B depicts the amino acid sequence for the heavy chain of mAb 16-2C9C3, including CDRs 1-3.

FIG. 36A depicts the nucleotide sequence of the light chain of mAb 16-2C9C3, including CDRs 1-3.

FIG. 36B depicts the amino acid sequence for the light chain of mAb 16-2C9C3, including CDRs 1-3.

FIG. 37A depicts the nucleotide sequence for the heavy chain of mAb 260-6F9F6, including CDRs 1-3.

FIG. 37B depicts the amino acid sequence for the heavy chain of mAb 260-6F9F6, including CDRs 1-3.

FIG. 38A depicts the nucleotide sequence of the light chain of mAb 260-6F9F6, including CDRs 1-3.

FIG. 38B depicts the amino acid sequence for the light chain of mAb 260-6F9F6, including CDRs 1-3.

DETAILED DESCRIPTION OF THE INVENTION

The present invention can be better understood from the following description of preferred embodiments, taken in conjunction with the accompanying drawings. It should be apparent to those skilled in the art that the described embodiments of the present invention provided herein are merely exemplary and illustrative and not limiting.

Definitions

Figure 4:
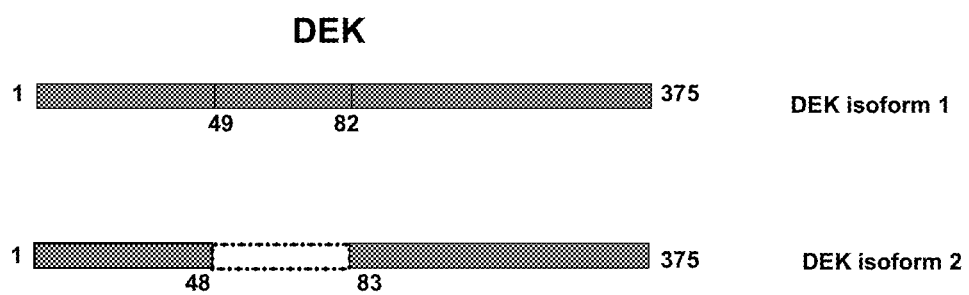
FIG. 4 depicts a graphic representation indicating the two (2) DEK isoforms. Note that while DEK isoform 1 is composed of 375 amino acid residues, DEK isoform 2 lacks the amino acid residues 49-82. The monoclonal antibody (cat no. 610948) used in this study recognizes only DEK isoform 1, whilst the polyclonal antibody (cat no. A301-335A) can recognize both DEK isoform 1 and DEK isoform 2.

The following terms shall have the meanings as defined hereunder:

As used herein, the term "DEK" refers to a protein with one SAP domain. DEK protein binds to cruciform and superhelical DNA and induces positive supercoils into closed circular DNA and involves in splice site selection during mRNA processing. DEK protein encompasses two isoforms (i.e., DEK isoform 1 and DEK isoform 2) (See, FIG. 4). In humans, isoforms 1 and 2 represent splice variants of DEK that are encoded by a DEK gene (NCBI Accession No. NW_001838973.1) (i.e., the DEK gene is located on chromosome 6p22). NCBI Accession No. for DEK protein isoform 1 is NP_003463.1 (SEQ ID NO: 3). NCBI Accession No. for DEK protein isoform 2 is NP_001128181.1 (SEQ ID NO: 2). The nucleotide sequence, as well as the protein sequences, are incorporated by reference herein.

As used herein, the term "precipitation" refers to the condensation of a solid in a solution. Such solid is commonly refers to as "precipitate."

As used herein, the term "chemical-induced precipitation" refers to using a chemical compound (e.g., acetone) that causes protein to precipitate from a solution. The precipitated protein is then collected by centrifugation (i.e., pellet). The protein pellet may be re-dissolved in a buffer (i.e., to re-fold protein) to form a solution compatible with downstream protein analysis such as Western blot analysis.

As used herein, the term "acetone" refers to the organic compound with the formula $(CH_3)_2CO$. Acetone is commonly used in inducing precipitation (i.e., causing protein to precipitate from a solution).

As used herein the term "TCA" refers to trichloroacetic acid that is commonly used to precipitate proteins in serum.

As used herein, the term "triethanolamine" refers to an organic chemical compound which contains a tertiary amine and a triol. A triol is a molecule with three alcohol groups. Like other amines, triethanolamine is a strong base due to the lone pair of electrons on the nitrogen atom.

As used herein, the term "filtration" refers to a mechanical or physical operation used for separating solids from fluids by interposing a medium (e.g., filter membrane) through which only the fluid can pass. Oversize solids in the fluid are retained. Filter membrane may have different cut-off pore size, for example, 30 kD or 3 kD cut-off.

As used herein, the term "Western blot assay" refers to an analytical technique used to detect specific proteins in a given sample of tissue homogenate or extract. It utilizes gel electrophoresis to separate either native proteins or denatured proteins by their lengths or 3-D structures. The separated proteins are transferred to a membrane (typically nitrocellulose or PVDF), and are detected using antibodies specific against a target protein.

As used herein, the term "antibody" refers to an immunoglobulin produced by B cells and has structural units of two large heavy chains and two small light chains. There are two general classes of antibody; namely, monoclonal antibody and polyclonal antibody. Monoclonal antibodies (mAb) refer to monospecific antibodies that are the same because they are made by identical immune cells that are all clones of a unique parent cell. Monoclonal antibodies are typically made by fusing myeloma cells with the spleen cells from a mouse that has been immunized with the desired antigen. Polyclonal antibodies are antibodies obtained from different B cells. They are a combination of immunoglobulins secreted against a specific antigen, each identifying a different epitope. Animals frequently used for polyclonal antibody production include goats, guinea pigs, rabbits, horses, sheep and the like. Rabbit is the most commonly used laboratory animal for this purpose.

As used herein, the term "protein" refers to a chain of at least two amino acids. The terms "polypeptide," "peptide," or "protein" are used interchangeably.

As used herein, the term "bladder cancer" refers to a cancerous tumor in the bladder. For purposes of this application, bladder cancer is not intended to be limited to cancer of any specific types (i.e., include many types of cancer in the bladder such as transitional cell carcinoma (TCC), squamous cell carcinoma, adenocarcinoma and combinations thereof).

As used herein, the term "TCC" refers to transitional cell carcinoma (also known as urothelial cell carcinoma or UCC). It is a type of cancer that typically occurs in the urinary system: the kidney, urinary bladder, and accessory organs. It is the most common type of bladder cancer and cancer of the ureter, urethra, and urachus. TCC often arises from the transitional epithelium, a tissue lining the inner surface of these hollow organs.

As used herein, the term "HxTCC" refers to patients that have a previously history of TCC.

As used herein, the term "UroTSA" refers to a cell line isolated from a primary culture of normal human urothelium through immortalization with a construct containing the SV40 large T antigen. It proliferates in serum-containing growth medium as a cell monolayer with little evidence of uroepithelial differentiation.

As used herein, the term "UroTSA DEK-V5" refers to over-expression of DEK in UroTSA cells.

As used herein, the term "UroTSA DEKsh" refers to UroTSA cells that have been transfected with silencing RNA against native DEK mRNA.

As used herein, the term "CAP" refers to human prostate cancer. The term "HxCAP" refers to patients who had previous history of suffering prostate cancer.

As used herein, the term "RCC" refers to renal cell carcinoma (also known as hypernephroma). It is a kidney cancer that originates in the lining of the proximal convoluted tubule. RCC is the most common type of kidney cancer in adults, responsible for approximately 80% of cases. The term "HxRCC" refers to patients who had previous history of suffering renal cell carcinoma.

As used herein, the term "BPH" refers to benign prostatic hyperplasia and is synonymous with "benign enlargement of the prostate" (BEP), and "adenofibromyomatous hyperplasia." All of these diseases are manifested by an increase in size of the prostate, often in middle-aged and elderly men.

As used herein, the term "ELISA" (also known as Enzyme-linked immunosorbent assay) refers to a biochemical technique used mainly to detect the presence of an antibody or an antigen in a biological sample. For purposes of this application, the ELISA technique is used for the detection of DEK protein (which is an antigen).

As used herein, the term "indirect ELISA" (also known as Antigen Down method) refers to a situation where an unknown amount of antigen is affixed (i.e., immobilized) to a solid surface, and then a specific antibody (that recognizes the antigen) is added onto the surface so as to allow the forming an antigen-antibody complex. The antigen-antibody complex is detected by a secondary antibody. Detection may be achieved by direct linking an enzyme to the secondary antibody or indirect via another antibody with an enzyme. The enzyme often converts to some detectable signal, most commonly a color change in a chemical substrate.

As used herein, the term "sandwich ELISA" (also known as Capture ELISA) refers to immobilizing a capture antibody (specific for the antigen) onto a solid support followed by addition of an amount of antigen. The bound antigen is then detected by a second antibody (i.e., detection antibody) which recognizes a region on the antigen that is different from that of the capture antibody. The captured antigen is detected by the detection antibody which can be covalently linked to an enzyme, or can itself be detected by addition of a secondary antibody which is linked to an enzyme.

As used herein, the term "anti-DEK antibody" refers to an antibody that recognizes DEK protein. There are two DEK isoforms (i.e., DEK isoform 1 which contains amino acids 1-375 and DEK isoform 2 which lacks amino acids 49-82 of the DEK isoform 1). The anti-DEK isoform 1 antibody is raised against a peptide corresponding to the amino acids of DEK isoform 1 protein. The anti-DEK isoform 2 antibody is raised against a peptide corresponding to amino acids of the DEK isoform 1 protein, with the exception of the amino acids 49-82.

As used herein, the term "neat urine" refers to urine sample collected from healthy individuals without any dilution or further concentration of the obtained sample. The developed sandwich ELISA with specific monoclonal antibodies provides a high sensitivity of <50 ng/mL and permits the use of neat urine in the ELISA.

As used herein, the term "synthetic urine" refers to a prepared solution that mimics human urine. The synthetic urine contains salt (0.9% NaCl) and human albumin (2%) in water, which represent the main constituents of human urine.

As used herein, the term "clone" refers to a single hybrid cell formed by the fusion of an antibody producing B cells with a myeloma cell and is capable of proliferating indefinitely to produce unlimited quantities of identical antibodies.

The present invention is directed to a novel and non-obvious method to detect DEK protein in a urine sample in humans. The present method comprises the steps of: (a) forming a precipitate from a urine sample with a chemical compound selected from the group consisting of acetone, trichloroacetic acid, ethanol, methanol/chloroform and ammonium sulfate; (b) re-suspending said precipitate in a polar solvent to form a solution, said solution has a final volume that is 10-50 fold less than that of said urine sample; (c) concentrating said solution 2-10 fold by filtration; and (d) detecting DEK in said concentrated solution using an anti-DEK antibody in a Western blot assay.

To the best of the present inventors' knowledge, this represents the first report for detection of DEK in a human urine sample. Using a cDNA microarray system, Sanchez-Carbayo et al. in 2003 reported that DEK gene (among many other genes) is increased in superficial tumors during progression of bladder cancer. Although it is logical to deduce that DEK protein may be presented in urine, no one has successfully documented such a finding and reported the presence of DEK protein in urine. Because DEK is an intracellular protein (i.e., not secreted or released), a mere increase in DEK mRNA in bladder cancer may not correspondingly produce DEK protein in urine. It is also plausible that the dilution of DEK protein in urine exists far below the detection limits of any assay. To date, there is no published literature describing DEK protein expression in multiple low and high grade bladder tumors and in the urine of bladder cancer patients. There are no reports of DEK protein being detected in urine by Western blot assay, or diagnosing/detecting bladder cancer by detecting DEK protein in urine samples. The present method therefore has made a significant improvement over the prior art and clearly documented the presence of DEK in urine (which has not previously known to exist).

Our present finding is surprising because the inventors of this application discovered that the sequential order of concentrating a urine sample is critical for the DEK detection. Specifically, no DEK protein is detectable in urine when a urine sample is concentrated by either chemical-induced precipitation or filtration-induced precipitation alone. DEK protein is also not detectable when a urine sample is first concentrated by filtration followed by a chemically-induced precipitation step. The present inventors discovered that a urine sample must be concentrated first by (i) chemical-induced precipitation, followed by (ii) filtration-induced concentration. The underlying mechanism for this observation is unclear.

Using a Western blot assay, the present inventors could not detect DEK protein in either urine pellets or urine supernatants. DEK protein was not detectable even when urines were concentrated by a chemical-induced precipitation method. Consecutive precipitations made no difference. These observations suggest that a mere multi-fold concentration of urine does not lead to a successful detection of DEK. Similarly, when urines were concentrated either by single filtration or consecutive filtration, also failed in DEK detection in urine.

Combination of concentrating first by filtration and then by chemical-induced precipitation was found to be ineffective in detecting DEK protein. Only when the urine sample was first concentrated by chemical-induced precipitation followed by filtration-induced concentration allows DEK protein detectable by Western blot assay.

The present invention provides a unique sequence of concentrating steps that are vital in DEK detection in urine. Without wishing to be bound to a theory, it is believed that a multitude of factors may play a role. These factors include (i) fold concentrations of urine, (ii) DEK protein conformation (i.e., tertiary protein structure of DEK) and (iii) salt concentrations. To be detectable, DEK protein may need a sufficient fold concentration of a urine sample. In chemical-induced precipitation, large amounts of chemical (e.g., acetone) are often needed to achieve the necessary fold concentration. Given this constraint, a single chemical-induced precipitation may not reach the necessary fold concentration. Filtration-induced concentration may cure this deficiency. In the process of chemical-induced precipitation, there may be a slight distort in tertiary protein structure and thus affect Western blot analysis. Filtration-induced concentration, although maintain the optimal protein tertiary structure, suffers from contamination with high salts. Our data with conductivity supports this contention. High salt concentration may affect Western blot assay in DEK detection.

The present inventors also surprisingly discovered a correlation between the presence of DEK protein in urine and detection/diagnosis of bladder cancer in humans. Specifically, the present invention provides a method of detecting bladder cancer in a human, comprising the steps of: (a) obtaining a urine sample from a human; (b) forming a precipitate from said urine sample with a chemical compound selected from the group consisting of acetone, trichloroacetic acid, ethanol, methanol/chloroform and ammonium sulfate; (c) re-suspending said precipitate in a polar solvent to form a solution, said solution has a final volume that is 10-50 fold less than that of urine sample; (d) concentrating said solution 2-10 fold by filtration; and (e) detecting DEK in said concentrated solution using an anti-DEK antibody in a Western blot assay, wherein the presence of DEK protein in said urine sample is an indicative of a bladder cancer in said human.

The present non-invasive method for detecting DEK in urine has an exceedingly high sensitivity (i.e., 79%) and specificity (i.e., 83%) as compared to other urine-based assays. Currently, there are five (5) commercial tests that detect biomarkers of bladder cancer in urine. These include: (i) NMP22 ELISA (detects nuclear mitotic apparatus protein) has 47-100% sensitivity and 60-80% specificity; (ii) BladderChek® dipstick test (detects nuclear mitotic apparatus protein) has 49.5% sensitivity and 87.3% specificity; (iii) BTA-Stat® test (detects complement factor H-related protein) has 50-70% specificity; (iv) urinary bladder cancer test (detects cytokine 8 and cytokine 18 by ELISA) has 56% sensitivity and 97% specificity; and (v) UroVysion® (a fluorescence in situ hybridization (FISH) based assay that detects amplification of chromosomes 3, 7 and 17 and loss of chromosome region 9p21) has 68-81% sensitivity and 79-96% specificity.

Our ELISA study reveals clearly that DEK isoform 2 protein is present in urine of humans who suffers from bladder cancer disorder. The finding is surprising and unexpected because while both isoform 1 and isoform 2 are present in tumor tissues, only isoform 2 is present in urine. The underlying mechanistic basis for our finding is unclear. It is unlikely that only the DEK isoform 2 is secreted or released during the pathogenesis of bladder cancer. Nevertheless, this constitutes the first report that DEK isoform 2 in urine bears a high correlation with human bladder cancer disorders.

Our ELISA is sensitive to detect DEK isoform 2 protein when the protein is in its proper tertiary conformation state. While ELISA is capable of detecting recombinant DEK protein spiked into a human urine, any acetone-treatment (i.e., during the concentrating step) would abolish the ability of ELISA in detecting DEK protein. This suggests that while our Western blot assay may tolerate some degree of tertiary protein conformation alternation (e.g., under denaturing conditions and acetone-treatment), ELISA assay can only detect DEK protein with filtration-induced concentration.

Urine may be conveniently collected from a human subject using a suitable container with a sufficient volume capacity for DEK protein assay. Commercially available urine containers may be used. In one embodiment, a urine container may contain a cap to prevent spilling and a means to allow the collected urine sample to be transported. Urine may be stored under appropriate conditions. In one embodiment, the container may be capable of withstanding freezing conditions (e.g., −80° C.). For purposes of the present assay, a sufficient urine volume may range from 15 ml to 75 mL. In one preferred embodiment, urine volume of between 20 mL to 40 mL is adequate.

Time of urine collection is not critical. In one embodiment, urine is collected as first void urine (i.e., in the morning). First void urine is believed to contain a greater amount of proteins, and may therefore increase the ability of detection for urine-based biomarkers. In another embodiment, urine may be collected during daytime or before bedtime.

Freshly collected urine (i.e., urine samples immediately after collection) may be used. Alternatively, frozen urine may be used (i.e., after thawing of frozen urine samples). For purposes of this application, we detect no difference between freshly collected urine and thawed urine. For convenient purposes, collected urine is stored between −20° C. and −80° C. Urine may be conveniently stored for at least 6-month duration.

In one embodiment, a protease inhibitor may be added to a urine sample and in an amount sufficient to prevent potential protein degradation of urine proteins. Suitable protease inhibitor includes, but not limited to, aprotinin, pepstatin, phenylmethanesulfonyl fluoride, chymostatin, and the like. In an alternative embodiment, a cocktail of suitable protease inhibitors may be used. For example, commercially available protease inhibitor cocktail ("Complete Protease Inhibitor Cocktail Tablets") (Roche; cat. no. 11836153001) may be used. In one embodiment, protease inhibitors may be added immediately after urine is collected. In yet an embodiment, protease inhibitors may be added after urine is thawed.

One skilled in the art would know how to optimize the suitable amount of protease inhibitors needed to prevent potential protein degradation in urine. In one embodiment, protease inhibitors are added to achieve a final concentration of 10 μg/ml to 5 mg/ml. In a preferred embodiment, protease inhibitors may be added to achieve a final concentration of 250 μg/ml to 750 μg/ml. In another preferred embodiment, protease inhibitor may be added to achieve a final concentration of 1 mg/ml.

Urine may be turbid which may be a symptom of a bacterial infection. A turbid urine may be caused by crystallization of salts such as calcium phosphate. In one embodiment, potential crude debris present in a turbid urine sample may be cleared prior to the concentrating steps. In one embodiment, collected urine samples may simply be passed through a cloth, paper, tissue and the like. For example, urine may be cleared by passing through a Kimwipe® (Kimberly-Clarke, Dallas, Tex.) prior to the urine concentrating steps.

One aspect of the present invention provides a step of concentrating urine using a chemical compound. Urine may be concentrated by a chemical-induced precipitation. Chemical-induced precipitation generally involves adding a chemical compound to a urine sample to cause urine proteins to form a precipitate. Urine precipitates are visible with a naked eye. Suitable chemical compounds include, without limitation, acetone, trichloroacetic acid, ethanol, methanol chloroform, ammonium sulfate and the like. In a preferred embodiment, the chemical compound is acetone or trichloroacetic acid. Methanol/chloroform is a solvent mixture, preferably comprising methanol and chloroform in a volume-to-volume ratio of 2:3. Other optimal volume-to-volume ratio of methanol and chloroform may be determined by one of ordinary skill in the art in so far as they function to induce urine protein to precipitate, To aid in urine concentration, chemical compound is used at an amount sufficient to induce the formation of a precipitate. In one embodiment, chemical compound is added to a urine sample to achieve a ratio of chemical compound volume to urine sample volume (vol/vol ratio) of between 10:1 to 2:1. In another embodiment, chemical compound is used at a vol/vol ratio of between 5:1 to 2:1. In a preferred embodiment, the vol/vol ratio is 2:1 (e.g., 50 ml acetone is added to 25 ml urine).

To enhance precipitation formation, it is found that adding ice-cold chemical compound is preferred. In one preferred embodiment, ice-cold acetone is used as the precipitating chemical. In another embodiment, ice-cold acetone is added to the urine sample and the resulting solution continued to be chilled at between −20° C. and −80° C. In yet another embodiment, ice-cold acetone is added to the urine sample and the solution chilled at −40° C.

In one embodiment, the resulting chemical-urine solution (e.g., acetone-urine) is chilled for an additional of 0.5-4 hours to cause the precipitates to be formed. In a preferred embodiment, the solution is chilled for 1-3 hours. In another preferred embodiment, the solution is chilled for 1.5-2 hours.

Methods are known in the art to collect precipitates as pellets after the step of chemical-induced precipitation. For example, a brief centrifugation (e.g., 12,000 rpm, 15 minutes) may be used to collect the precipitated proteins.

Another aspect of the present invention provides a step of further concentrating urine using a filtration method. Prior to the filtration-induced concentration, the pelleted proteins may conveniently be re-suspended in a suitable re-suspension buffer. Without wishing to be bound by a theory, the re-suspension buffer is believed to enhance refolding of the precipitated proteins. Re-suspension may help to restore and reform the precipitated proteins into a proper tertiary protein structure.

Ideally, the re-suspension buffer may match the pH of urine. The pH of urine is close to neutral (pH 7) but can normally vary between 4.4 and 8. A diet high in citrus, vegetables, or dairy can increase urine pH. Some drugs can increase urine pH, including acetazolamide, potassium citrate, and sodium bicarbonate. On the other hand, a diet high in meat or cranberries can decrease urine pH. Drugs that can decrease urine pH include ammonium chloride, chlorothiazide diuretics, and methenamine mandelate. In one embodiment, the re-suspension buffer has a pH of between 5-9. More preferably, the re-suspension buffer has a pH of between 6-8. More preferably, the re-suspension buffer has a pH of 7.5.

One skilled in the art would recognize the use of common buffers to maintain pH of the re-suspension buffer. A buffer solution is an aqueous solution consisting of a mixture of a weak acid and its conjugate base or a weak base and its conjugate acid. Buffer solutions are used as a means of keeping pH at a nearly constant value in a wide variety of chemical applications. Exemplary common buffer includes triethanolamine, TRIS, HEPES, MOPS, and the like. Preferably, the re-suspension buffer is isotonic.

In one embodiment, the re-suspension buffer is an organic chemical compound which is both a tertiary amine and a triol such as triethanolamine. Preferably, the re-suspension buffer contains 10 mM triethanolamine. In another embodiment, the re-suspension buffer may include a sugar to enhance tonicity. Exemplary sugar includes, but not limited to, sucrose. Preferably, the re-suspension buffer contains 250 mM sucrose. An exemplary re-suspension buffer is a solution of 10 mM tri-ethanolamine and 250 mM sucrose.

The pelleted proteins are re-suspended at a minimal volume that is much less than the original urine sample volume. One skilled in the art would recognize a minimum optimal volume in re-suspending the pellet proteins. In one embodiment, the pelleted protein is re-suspended in a volume of re-suspension buffer of 500 μl. The volume of the re-suspension buffer may range from 5-50 fold less than that of the original urine sample. Preferably, the volume of the re-suspension buffer ranges from 20-40 fold less than the original urine sample volume. More preferably, the volume of the re-suspended is 30 fold less than the original urine sample volume (e.g., pelleted proteins from 60 mL urine is re-suspended in 500 μl re-suspension buffer).

Re-suspended concentrated urine is further concentrated. In one aspect, the present invention provides a step of concentrating urine by filtration. Filtration-induced concentration may be accomplished through the use of spin filter concentration units. Examples of commercially available spin-filter concentration units include units sold under the tradenames Microcon®, Centricon® and Centriprep®.

In one embodiment, the spin filter has a molecular weight cut-off of between 1 kD and 40 kD. In another embodiment, the spin filter has a molecular weight cut-off of 3 kD. In another embodiment, the spin filter has a molecular weight cut-off of 30 kD.

Ideally, filtration-induced concentration is used to achieve an increase of concentration between 2-fold to 10-fold. In one embodiment, concentration is increased between 4-fold to 8-fold. In a preferred embodiment, concentration is increased 5-fold.

Protein concentrations of urine samples may be conveniently quantified by methods that are known to the art including assays that are commercially available. For example, one commercially available kit is the BCA assay kit (Pierce, Thermo Fisher Scientific, Rockford, Ill.).

In one aspect, the present invention provides an assay to detect DEK protein present in the concentrated urine samples. In one embodiment, protein present in the filtration-concentrated sample is adjusted to a level of 10-1,000 µg/ml. Preferably, the protein concentration in the filtration-concentrated sample is 100 µg/ml.

DEK protein may be detected using standard protein detection assays that are known in the art. These assays include, but not limited to, Western blot analysis, ELISA, radioimmunoassay, dot-blot assay, and the like. Preferably, DEK protein is detected by Western blot analysis.

After urine samples are treated (i.e., subject to chemical-induced precipitation and filtration-induced concentration), the proteins are separated using SDS-PAGE gel electrophoresis. The technology of SDS-PAGE gel electrophoresis is well known in the art. Approximately 5 µg to 100 µg of total protein is run on a SDS-PAGE gel. Preferably, 10 µg to 75 µg of total protein is used. More preferably, 25 µg of total protein is used. The conditions for SDS-PAGE gel electrophoresis can be conveniently optimized by one skilled in the art. In one embodiment, SDS-PAGE gel is run at 100 V for 90 min of 400 mA for 90 minutes. Optimally, gel electrophoresis may be performed under denaturing conditions. SDS-PAGE gel electrophoresis conditions are well known by those skilled in the art and can be conveniently optimized.

Following gel electrophoresis, the proteins present in the gels may be transferred onto a suitable solid surface such as nitrocellulose paper, nylon membrane, PVDF membrane and the like. Preferably, PVDF membrane is used. The conditions for protein transfer after SDS-PAGE gel electrophoresis may be optimized by one skilled in the art.

Western blot may be used to detect DEK protein in the concentrated urine (after SDS-PAGE). A first antibody specific for the protein of interest (e.g., DEK) is employed. The first antibody may be either a monoclonal antibody or polyclonal antibody. Antibodies against the protein biomarker can be prepared using standard protocols or obtained from commercial sources. Techniques for preparing mouse monoclonal antibodies or goat or rabbit polyclonal antibodies (or fragments thereof) are well known in the art.

Membrane may be incubated with a blocking solution before the incubation with the first antibody. Blocking solution may include agents that reduce non-specific binding of antibody. For example, blocking solution may include 5% skim milk in PBST (0.1% Tween-20).

Bound proteins (e.g., 10-100 µg) on the membrane are incubated with a first antibody in a solution. In one embodiment, the first antibody is used at a concentration of 0.2-2 µg/mL. Preferably, the first antibody is used at a concentration of 1 µg/mL.

Incubation conditions may be optimized to maximize the binding of the first antibody with the bound biomarker proteins. In one embodiment, the incubation time is 1-6 hours. In a preferred embodiment, the incubation time is 2 hours.

After incubation with the first antibody, unbound antibody may be conveniently removed by washing. In one embodiment, the washing solution may include PBST.

Protein biomarker-first antibody complex (e.g., DEK-anti-DEK antibody) may be detected by incubation with a second antibody that is specific for the first antibody. The second antibody may be a monoclonal antibody or a polyclonal antibody (e.g., mouse, rabbit, or goat). In one embodiment, the second antibody may carry a label which may be a directly detectable label or may be a component of a signal-generating system. In another embodiment, the second antibody is a goat anti-rabbit antibody or goat anti-mouse antibody that is labeled with a peroxidase. Such labeled antibodies and systems are well known in the art.

Direct detectable label or signal-generating systems are well known in the field of immunoassay. Labeling of a second antibody with a detectable label or a component of a signal-generating system may be carried out by techniques well known in the art. Examples of direct labels include radioactive labels, enzymes, fluorescent and chemiluminescent substances. Radioactive labels include $^{124}I$, $^{125}I$, $^{128}I$, $^{131}I$, and the like. A fluorescent label includes fluorescein, rhodamine, rhodamine derivatives, and the like. Chemiluminescent substances include ECL chemiluminescent.

In another aspect, the present invention provides a method of detecting and diagnosing bladder cancer. This is accomplished by obtaining and testing a urine sample and detecting the presence of DEK protein in the urine sample by the detection method provided herein. The presence of DEK protein in the urine sample indicates that the patient tested is suffering from bladder cancer. Thus, the present invention provides an efficient, non-invasive method for the detection and diagnosis of bladder cancer by detecting DEK protein in a urine sample.

Our Western blot assay results suggest that urine contains only DEK isoform 2 in individuals suffering from bladder cancer. In our assay, we used a monoclonal anti-DEK antibody that specifically recognize DEK isoform 1 (but not DEK isoform 2) (i.e., the antibody was raised specifically to a region that is present only in DEK isoform 1 but not DEK isoform 2). The polyclonal anti-DEK antibody that was used recognizes both DEK isoforms. Because both monoclonal and polyclonal anti-DEK antibodies recognized DEK proteins in both bladder cancer cell culture and bladder cancer tissue samples, this implies that DEK isoform 1 and DEK isoform 2 are present in these cells and tissues.

However, only the polyclonal anti-DEK antibody (but not the monoclonal anti-DEK antibody) recognized DEK protein in urine samples from patients suffering bladder cancer, this suggests urine contains DEK isoform 2, but not DEK isoform 1.

ELISA Assay

Detection of DEK protein in urine may be accomplished by techniques known in the art, e.g., ELISA (enzyme-linked immunosorbent assay), Western blots, and the like.

As appreciated by one skilled in the art, an enzyme-linked immunosorbent assay (ELISA) may be employed to detect proteins in urine, specifically DEK protein in urine. In one aspect, the present invention provides an ELISA in detecting DEK protein (i.e., DEK isoform 2 protein) in human urine. The presence of DEK isoform 2 protein is an indication of bladder cancer.

In one embodiment, the present invention provides an initial step of an ELISA in which an anti-DEK antibody is immobilized onto a surface (for example by passive adsorption known as coating). For purposes of this application, exemplary DEK is isoform 2 and the fragment thereof. Anti-DEK antibody may recognize recombinant full-length DEK protein as well as fragments thereof via its recognition of specific epitopes. Immobilization of anti-DEK antibody may be performed on any inert support (or solid support) that is useful in immunological assays. Examples of commonly used inert supports include small sheets, Sephadex and assay plates manufactured from polyethylene, polypropylene or polystyrene. In a preferred embodiment the immobilized anti-DEK antibody is coated on a microtiter plate that allows analysis of several samples at one time. More preferably, the microtiter plate is a microtest 96-well ELISA plate, such as those sold under the name Nunc Maxisorb or Immulon.

Antibody immobilization is often conducted in the presence of a buffer at an optimum time and temperature optimized by one skilled in the art. Suitable buffers should enhance immobilization without affecting the antigen binding properties. Sodium carbonate buffer (e.g., 50 mM, pH 9.6) is a representative suitable buffer, but others such as Tris-HCl buffer (20 mM, pH 8.5), phosphate-buffered saline (PBS) (10 mM, pH 7.2-7.4) are also used. Optimal coating buffer pH will be dependent on the antigen(s) being immobilized. Optimal results may be obtained when a buffer with pH value 1-2 units higher than the isoelectric point (pI) value of the protein is used. Incubation time ranges from 2-8 hours to overnight. Incubation may be performed at temperatures ranging from 4-37° C. Preferably, immobilization takes place overnight at 4° C. The plates may be stacked and coated long in advance of the assay itself, and then the assay can be carried out simultaneously on several samples in a manual, semi-automatic, or automatic fashion, such as by using robotics.

Blocking agents are used to eliminate non-specific binding sites in order to prevent unwanted non-specific antibody binding to the plate. Examples of appropriate blocking agents include detergents (for example, Tween-20, Tween-80, Triton-X 100, sodium dodecyl sulfate), gelatin, bovine serum albumin (BSA), egg albumin, casein, non-fat dried milk and the like. Preferably, the blocking agent is BSA. Concentrations of blocking agent may easily be optimized (e.g. BSA at 1-5%). The blocking treatment typically takes place under conditions of ambient temperatures for about 1-4 hours, preferably 1.5 to 3 hours.

After coating and blocking, urine from control subjects or patients suspected of bladder cancer are added to the immobilized antigens in the plate. Concentrated urine suspended in Phosphate Buffered Saline (PBS) containing 0.5% BSA, 0.05% TWEEN 20® detergent may be used. TWEEN 20® acts as a detergent to reduce non-specific binding.

The conditions for incubation of the biological sample and immobilized antigen are selected to maximize sensitivity of the assay and to minimize dissociation. Preferably, the incubation is accomplished at a constant temperature, ranging from about 0° C. to about 40° C., preferably from about 22 to 25° C. to obtain a less variable, lower coefficient of variant (CV) than at, for example, room temperature. The time for incubation depends primarily on the temperature, being generally no greater than about 10 hours to avoid an insensitive assay. Preferably, the incubation time is from about 0.5 to 3 hours, and more preferably 1.5-3 hours at room temperature to maximize binding to immobilized capture antigen.

Following incubation of the biological sample (urine) and immobilized anti-DEK antibody, unbound biological sample is separated from the immobilized antibody by washing. The solution used for washing is generally a buffer ("washing buffer") with a pH determined using the considerations and buffers described above for the incubation step, with a preferable pH range of about 6-9. Preferably, pH is 7. The washing may be done three or more times. The temperature of washing is generally from refrigerator to moderate temperatures, with a constant temperature maintained during the assay period, typically from about 0-40° C., more preferably about 4-30° C. For example, the wash buffer can be placed in ice at 4° C. in a reservoir before the washing, and a plate washer can be utilized for this step.

Next, the immobilized capture anti-DEK antibody and biological sample (i.e., urine) are contacted with a detectable antibody at a time and temperature optimized by one skilled in the art. Detectable antibody may include a monoclonal antibody or a polyclonal antibody. These antibodies may be directly or indirectly conjugated to a label. Suitable labels include moieties that may be detected directly, such as fluorochrome, radioactive labels, and enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, horseradish peroxidase (HRP), alkaline phosphatase, and the like. Preferably, the detection antibody is a goat anti-human IgG polyclonal antibody that binds to human IgG and is directly conjugated to HRP. Incubation time ranges from 30 minutes to overnight, preferably about 60 minutes. Incubation temperature ranges from about 20-40° C., preferably about 22-25° C., with the temperature and time for contacting the two being dependent on the detection means employed.

The conjugation of such labels to the antibody, including the enzymes, is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166.

In one embodiment, after the complex formation between DEK protein and anti-DEK antibody, the antibody binding to antigen (i.e., DEK protein) is assessed by detecting a label on the primary antibody. In another embodiment, the primary antibody is assessed by detecting binding of a secondary antibody or reagent to the primary antibody. In a further embodiment, the secondary antibody is labeled. Many means are known in the art for detecting binding in an immunoassay and are within the scope of the present invention. For example, to select specific epitopes of recombinant or synthetic polypeptide, one may assay antibody binding in an ELISA assay wherein the polypeptides or its fragments containing such epitope.

In another aspect, the present invention provides direct immobilizing urine samples (containing DEK protein) onto a solid support (e.g., microtiter plates). This is also known as antigen-down ELISA (i.e., indirect ELISA). In such an assay, a microtiter plate is coated with a sample containing a certain antigen (e.g., DEK protein). After allowing for adsorption of the antigen onto the plate, and washing off all non-bound materials, an antibody is added to the plate and the excess washed off. Prior to addition of the antibody, one skilled in the art would appreciate blocking non-specific bindings with appropriate blocking agents (e.g., Tween-20, Tween-80, Triton-X 100, sodium dodecyl sulfate), gelatin, bovine serum albumin (BSA), egg albumin, casein, non-fat dried milk and the like). The added antibody may have already been labeled with a reporter molecule to permit the generation of a signal to be read by known techniques (e.g., microtiter plate reader).

An anti-DEK protein is directly added to allow the formation of DEK and anti-DEK antibody complex. Optimal conditions for antigen-antibody complex formation may be conveniently adjusted by one of ordinary skilled in the art. Unbound antibody is removed by washing; generally by a buffer. Detectable antibody may include a monoclonal antibody or a polyclonal antibody. These antibodies may be directly or indirectly conjugated to a label (as described above).

Alternatively an enzyme conjugated secondary antibody can be used for detection of antigen-antibody complex. Upon addition of a suitable chromogen substrate, a color develops which is used as an indicator of the amount of antigen present.

mAb 260-6F9F6 and mAb 16-2C9C3

In one embodiment, the present invention provides a total of eight (8) anti-DEK monoclonal antibodies, which antibodies recognize and bind to DEK protein. They include mAb 16-1D4F8, mAb 16-1D4F10, mAb 16-DC9C3, mAb 260-6C5G8, mAb 260-6D11F2, mAb 260-6F9F6, mAb 320-2B9A8, and mAb 320-3E9E11. Using these mAbs in different permutations (either as a capture antibody or detection), we discovered that two (2) of these mAbs are useful in establishing a highly sensitive ELISA (<50 ng/mL). In a preferred embodiment, the present invention provides an ELISA employing mAb 16-2C9C3 as the capture antibody and mAb 260-F9F6 as the detection antibody.

A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-D space to form the actual antibody binding site which locks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework, which forms the environment for the CDRs.

The mAb 16-2C9C3 was further characterized by sequencing its nucleotides and amino acids. In one embodiment, the present invention provides an isolated anti-DEK antibody (mAb 16-2C9C3) comprising: (i) CDR1 of the heavy chain variable region which has the amino acid sequence of SEQ ID NO:15; (ii) CDR2 of the heavy chain variable region which has the amino acid sequence of SEQ ID NO:16; (iii) CDR3 of the heavy chain variable region which has the amino acid sequence of SEQ ID NO:17. In another embodiment, the present invention provides an isolated anti-DEK antibody (mAb 16-2C9C3) comprising: (i) CDR1 of the light chain variable region which has an amino acid sequence of SEQ ID NO: 23; (ii) CDR2 of the light chain variable region which has the amino acid sequence of SEQ ID NO:24; and (iii) CDR3 of the light chain variable region which has the amino acid sequence of SEQ ID NO:25.

In yet another embodiment, the present invention provides an isolated monoclonal antibody (mAb 16-2C9C3), comprising: (i) CDR1 of the heavy chain variable region which has the amino acid sequence of SEQ ID NO:15; (ii) CDR2 of the heavy chain variable region which has the amino acid sequence of SEQ ID NO:16; (iii) CDR3 of the heavy chain variable region which has the amino acid sequence of SEQ ID NO:17, (iv) CDR1 of the light chain variable region which has an amino acid sequence of SEQ ID NO: 23; (v) CDR2 of the light chain variable region which has the amino acid sequence of SEQ ID NO:24; and (vi) CDR3 of the light chain variable region which has the amino acid sequence of SEQ ID NO:25.

The mAb 260-F9F6 was also further characterized by sequencing its nucleotides and amino acids. In one embodiment, the present invention provides an isolated anti-DEK antibody (mAb 260-F9F6) comprising: (i) CDR1 of the heavy chain variable region which has the amino acid sequence of SEQ ID NO:31; (ii) CDR2 of the heavy chain variable region which has the amino acid sequence of SEQ ID NO:32; (iii) CDR3 of the heavy chain variable region which has the amino acid sequence of SEQ ID NO:33. In another embodiment, the present invention provides an isolated anti-DEK antibody (mAb 260-F9F6) comprising: (i) CDR1 of the light chain variable region which has an amino acid sequence of SEQ ID NO: 39; (ii) CDR2 of the light chain variable region which has the amino acid sequence of SEQ ID NO:40; and (iii) CDR3 of the light chain variable region which has the amino acid sequence of SEQ ID NO:41.

In yet another embodiment, the present invention provides an isolated monoclonal antibody (mAb 260-F9F6), comprising: (i) CDR1 of the heavy chain variable region which has the amino acid sequence of SEQ ID NO:31; (ii) CDR2 of the heavy chain variable region which has the amino acid sequence of SEQ ID NO:32; (iii) CDR3 of the heavy chain variable region which has the amino acid sequence of SEQ ID NO:33, (iv) CDR1 of the light chain variable region which has an amino acid sequence of SEQ ID NO: 39; (v) CDR2 of the light chain variable region which has the amino acid sequence of SEQ ID NO:40; and (vi) CDR3 of the light chain variable region which has the amino acid sequence of SEQ ID NO:41.

The use of mAb 16-2C9C3 (as a capture antibody) and mAb 260-F9F6 (as a detection antibody) surprisingly yields high sensitivity in DEK detection. The ELISA affords at least <50 ng/mL limit of detection. Preferably, the ELISA offers 3.9 ng/mL limit of detection. To our surprise and for reasons unknown, the use of mAb 16-2C9C3 (capture antibody) and mAb 260-F9F6 (detection antibody) does not require a concentration step of urine. There is no need to concentrate urine (either by filtration or chemical-induced method as described above) prior to the ELISA detection. Neat urine can be used in the ELISA to detect DEK.

Kits

Another aspect of the invention is to provide a kit that may be used to detect DEK protein in urine. The kit according to the present invention includes a set of antibodies (i.e., a first antibody and a second antibody) that are specific for DEK protein. In one embodiment, the kit contains reagents (e.g., precipitating chemicals such as acetone or TCA) for treating the urine sample so as to enable DEK protein to be detected from the sample. In another embodiment, the kit contains ELISA plates necessary to perform direct or indirect ELISA to detect DEK protein.

Kits provided herein include instructions, such as a package insert having instructions thereon, for using the reagents to prepare and steps in concentrating a urine sample. Such instructions may be for using the reagents to prepare the urine sample to specifically allow detection of DEK protein from the urine. In another embodiment, the instructions are directed to the use of antibodies (either monoclonal or polyclonal) that recognize and bind to DEK protein in Western blot analysis or ELISA.

In one embodiment, the present invention provides a kit for detecting bladder cancer in a human, employing mAb 16-2C9C3 as a capture antibody and/or mAb 260-6F9F6 as a detection antibody for DEK. The provided instruction guides one skilled artisan to use the mAb 16-2C9C3 and mAb 260-6F9F6.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1 Western Blot Detection of DEK Protein in Bladder Cell Lines

In this series of studies, we optimized the detection of DEK protein in a biological sample (e.g., urine) using Western blot assay. We tested cell lysate extracts obtained from four (4) bladder cancer cell lines (i.e., RT-4, 5637, T-24 and TCCSUP) and examined their DEK protein expression. These cells were chosen to represent different stages of bladder cancer. In addition, we tested cell extracts from bladder epithelial cells transformed with SV-40 T-antigen (i.e., UroTSA), progenitor human epithelial cells (i.e., HBEP cells), and differentiated HBEP cells for their DEK protein expression. Note that HBEP cells were treated with 1 mM calcium chloride to prevent cycling in growth media.

Cell extracts from $1\times10^7$ cells were obtained using RIPA buffer (i.e., 25 mM Tris-HCl (pH 7.6), 150 mM NaCl, 1% NP-40, 1% sodium deoxycholate, and 0.1% SDS). Protein was quantified using a BCA assay kit (Pierce, Thermo Fisher Scientific, Rockford, Ill.). Cell lysates extracts were further concentrated to a concentration of between 4 and 8 µg/µl. 30 µg of the cell extracts were used in the Western blot analysis using an anti-DEK antibody (e.g., an anti-DEK monoclonal antibody; cat #610948) (BD Bioscience, San Jose, Calif.).

Figure 1:
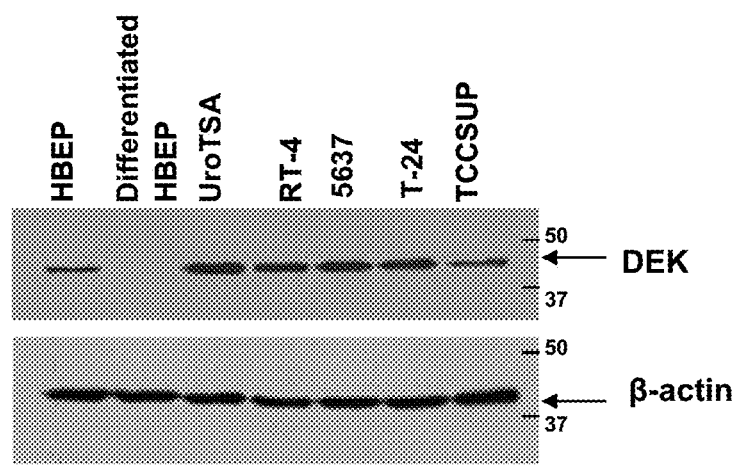
FIG. 1 depicts the expression of DEK protein in undifferentiated bladder epithelial cell line (i.e., HBEP), differentiated HBEP, a transformed epithelial cell line (i.e., UroTSA), and four (4) bladder cancer cell lines (i.e., RT-4, 5637, T-24 and TCCSUP) in a Western blot assay. β-actin serves as a positive control protein.

FIG. 1 shows a Western blot demonstrating the presence of DEK protein expressed in four (4) bladder cancer cell lines (i.e., RT-4, 5637, T-24 and TCCSUP) as well as the UroTSA and undifferentiated HBEP cells. In this Western blot analysis, we used a monoclonal anti-DEK antibody (cat. no. 610948) (BD Bioscience, San Jose, Calif.). Note that DEK protein has a molecular size of ~43 kD. DEK protein was not detectable in differentiated (i.e., non-cancer) HBEP cells. f-actin served as a loading control. In another Western blot analysis, we used a polyclonal anti-DEK antibody (cat. no. A-301-335A) (Bethyl Labs, Montgomery, Tex.). Similar to that in monoclonal antibody study, we observed a similar profile in DEK protein expression in these cells (data not shown).

Thus, we have developed a Western blot assay that is sensitive and specific in detecting DEK protein expression using cell lysates extracts obtained from bladder cancer cell lines, using either a monoclonal anti-DEK antibody or a polyclonal anti-DEK antibody.

Example 2 Western Blot Fails to Detect DEK Protein in Cultured Media

In this study, we examined if DEK protein can be released from bladder cancer cells (i.e., secreted from cells). To do so, we first collected cultured media from two (2) bladder cancer cell lines (i.e., T-24 and 5637) and then examined DEK protein expression in these cultured media. One (1) ml of cultured media was collected and briefly centrifuged (3,000 rpm, 5 min) to remove any cellular debris. The cultured media was subsequently concentrated to 50-fold (i.e., from 500 µl to 10 µl) using a Microcon® 3K filter (Millipore, Billerica, Mass.). The entire 10 µl of the concentrated cultured media sample was loaded in a Western blot assay. DEK protein was examined using a polyclonal anti-DEK antibody (cat. no. A-301-335A) (Bethyl Labs., Montgomery, Tex.). UroTSA (10 µg) whole cell lysate was used as a control.

Figure 2:
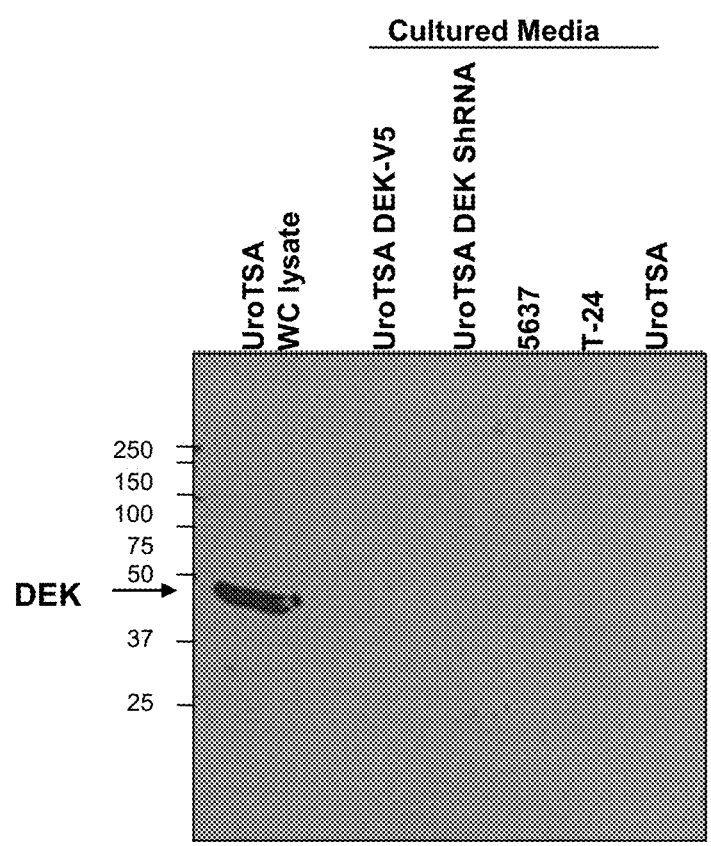
FIG. 2 depicts the expression of DEK protein in the cultured media from five (5) different cultured cell lines in a Western blot assay. These include: (i) a transformed epithelial cell line (i.e., UroTSA) transfected with DEK-V5; (ii) UroTSA hosting shRNA against DEK (i.e., DEK knockdown); (iii) bladder cancer cell line 5637; (iv) bladder cancer cell line T-24; and (v) UroTSA. Whole cell lysates from UroTSA (i.e., WC lysates of UroTSA) serves as a positive control.

FIG. 2 shows that DEK protein was not detectable in the cultured media of the two (2) bladder cancer cell lines (i.e., T-24 and 5637). DEK protein was not detectable in the cultured media from the transformed bladder epithelial cells (i.e., UroTSA) and from bladder epithelial cells that were over-expressing DEK protein (UroTSA DEK-V5). This data suggest that DEK protein is neither secreted nor released from bladder cancer cells. As a negative control, we transfected DEK shRNA (i.e., small hairpin RNA against DEK) in UroTSA cells in order to shut down DEK protein expression. No detectable DEK protein was found in the cultured media from UroTSA DEK shRNA, confirming that DEK protein may not be released from bladder cancer cells.

Example 3 Western Blot Detection of DEK Protein in Bladder Tissues

In this study, we examined if our Western blot assay (see Example 1) could detect DEK protein in bladder tissues obtained from human subjects (e.g., bladder cancer patients or healthy individuals).

Twenty-seven (27) bladder tumor tissue samples were obtained from patients who suffered from low and high grade transitional cell carcinoma (TCC). For comparison, twenty-seven (27) normal bladder tissue samples were obtained from the adjacent sites of the same individuals. Tissue lysate extracts were prepared using RIPA buffer (as described above) and the tissue extracts were prepared to a protein concentration of 2-10 µg/µL. Protein concentration of the tissue lysates extracts was determined using a BCA assay kit (Pierce, Thermo Fisher Scientific, Rockford, L). ~50 g of the tissue lysates extracts from each sample was analyzed for their DEK protein expression in our Western blot assay, using a monoclonal anti-DEK antibody (i.e., cat. no. 610948). In some Western blot analysis, we used a polyclonal anti-DEK antibody (cat. no. A-301-335A) (Bethyl Labs, Montgomery, Tex.) and observed the same DEK protein expression. 10 µg of the UroTSA cell lysates was used as a control.

Figure 3:
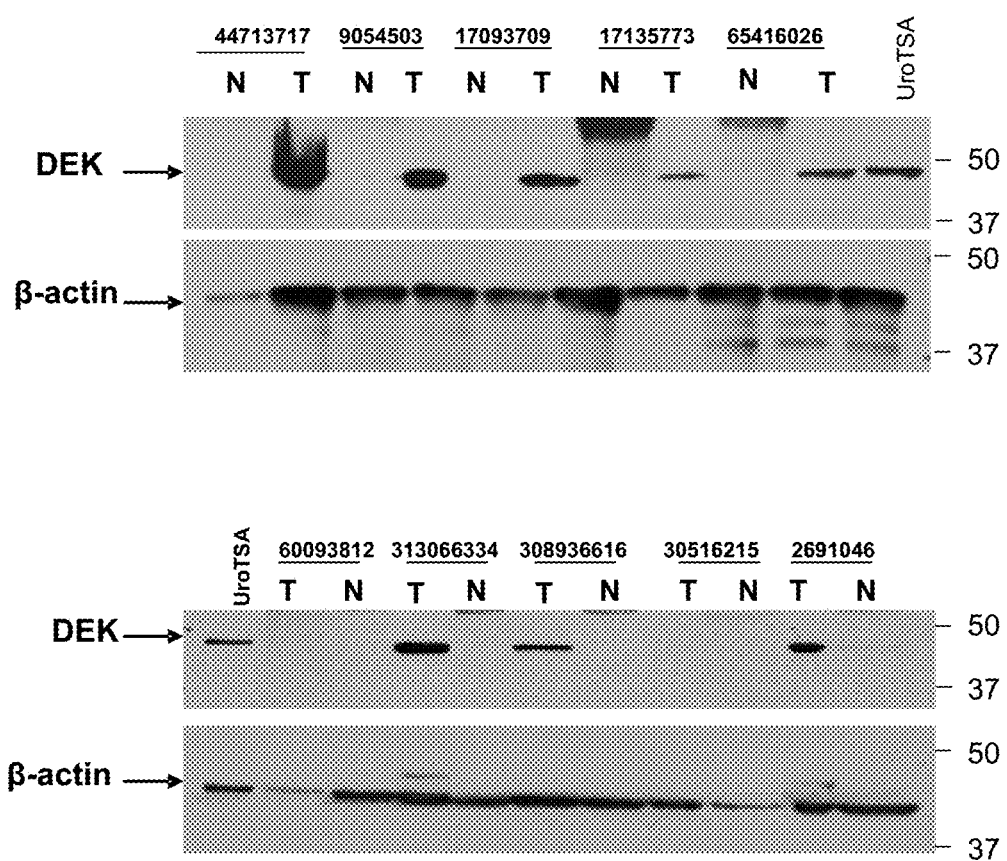
FIG. 3 depicts the expression of DEK protein of bladder tumor tissues (i.e., T) from ten (10) bladder cancer patients in a Western blot assay. Adjacent tissues (i.e., N) from the same patients were used as a comparison. UroTSA serves as a control cell line. β-actin serves as a positive control protein.

FIG. 3 shows the Western blot of the DEK protein in ten (10) representative bladder tumor tissues using the monoclonal anti-DEK antibody. In total, we have examined twenty-seven (27) bladder tissue samples. Out of these bladder tissue samples, DEK protein expression was detected in twenty-two (22) bladder tumor tissues. The bladder tumor was clinically diagnosed as transitional cell carcinoma (TCC). A summary of the DEK protein expression in all these bladder tissues are provided in Table 1. Note that DEK protein expression was detected in both low-grade TCC and high-grade TCC. DEK protein was not detectable in the adjacent normal bladder tissues, indicating high specificity. Our polyclonal ant-DEK antibody was employed in some Western blot analysis and we have confirmed a similar DEK protein expression in these bladder tumor tissues.

TABLE 1

DEK Protein Expression in Bladder Tumor Tissues

| Tissue Samples | Cancer Staging | Grade | TCC Tissues | Normal Adjacent Tissues |
|---|---|---|---|---|
| 17135773 | High | T2 | + | – |
| 2691046 | High | T2 | ++++++ | – |
| 30516215 | High | T2 Squamous Differentiation | – | – |
| 44713717 | High | T2 | ++++ | – |
| 52203387 | High | T1 | ++++++ | – |
| 65416026 | High | T1 | ++ | – |
| A00309103 | High | T3a | +++ | – |
| B0087901 | High | TX | ++++ | – |
| B01712101 | High | Tx | – | – |
| E00061103 | High | T1 | – | – |
| E00397102 | High | | ++ | – |
| E00749102 | High | T3 | ++ | – |
| 17093709 | Low | TA | +++ | – |
| 308936616 | Low | TA | ++++ | – |
| 313066334 | Low | T1 | ++++++ | – |
| 314593377 | Low | TA | ++++ | – |
| 42070185 | Low | TA | ++++++ | – |
| 53976239 | Low | T1 | ++++++ | – |
| 60093812 | Low | T1 Squamous Differentiation | – | – |
| 8875254 | Low | TA | + | – |
| 9054503 | Low | TA | +++ | – |
| A00050109 | X | T1 | ++++ | – |
| A00491105 | X | T2b | – | – |
| A00903104 | X | T2a | ++++ | – |
| E00019101 | X | TX | + | – |
| E0028719 | X | T4 | ++ | – |
| E00300105 | X | T1 | ++++ | – |
| 42012815 | X | Inflammation | – | – |

In sum, we have developed a Western blot assay for detecting DEK protein expression. Using this assay, we have found DEK protein expression in bladder tissues from individuals suffering from low-grade and high-grade bladder cancer. The data further show that DEK protein can be found to present in bladder tissues as early as stage 0a (i.e., Ta) in bladder cancer. Note that DEK protein is not expressed in normal healthy tissues, indicating high specificity.

DEK Isoforms and Antibody Recognition—

So far, we have used two (2) anti-DEK antibodies in the Western blot analysis for bladder cancer cell extracts and tissue extracts. The first antibody was a monoclonal anti-DEK antibody (cat. no. 610948) obtained from BD Bioscience (San Jose, Calif.). This monoclonal antibody was raised using synthetic peptides corresponding to the amino acid residues 19-169 of the DEK isoform 1 (See, FIG. 4). The second antibody was a polyclonal anti-DEK antibody (cat. no. A-301-335A) available from Bethyl Labs (Montgomery, Tex.). This polyclonal antibody was raised using synthetic peptides corresponding to amino acid residues 325-375 of the DEK isoform 1 (See, FIG. 4). DEK protein is known to encompass two (2) isoforms (namely; DEK isoform 1 and DEK isoform 2). DEK isoform 2 differs from DEK isoform 1 by missing the amino acid residues 49-82. It is noted that our monoclonal antibody can recognize DEK isoform 1 (but not DEK isoform 2), while our polyclonal antibody can recognize both DEK isoforms. (See, FIG. 4).

We observed DEK protein expression in both bladder cancer cell line extracts and bladder tumor tissue extracts. Because our monoclonal anti-DEK antibody can only recognize DEK isoform 1 but not isoform 2 and our polyclonal anti-DEK antibody recognizes both isoforms, we concluded that bladder cancer cell lines and bladder tumor tissues express both DEK isoform 1 and DEK isoform 2.

Example 4 Western Blot Detection of DEK Protein in Urine

Urine samples (in aliquots of 25 ml) were collected in the presence of various protease inhibitors (e.g., aprotinin, pepstatin, phenylmethanesulfonyl fluoride, chymostatin, etc) at a concentration sufficient to inhibit protease activity (e.g., 1 mg/ml) to avoid potential DEK protein degradation. In this particular study, we used a protease inhibitor cocktail (Roche, Indianapolis, Ind.). Urine samples could be used immediately after collection or may be stored at –80° C. For the sake of convenience, most of our studies employed frozen urine samples. Prior to Western blot analysis, frozen urine samples were thawed by leaving the samples at room temperature for 1-2 hours.

We examined if our Western blot assay could detect DEK protein in human urine. We obtained urine samples from four (4) patients suffering from bladder cancer and one (1) healthy patient.

a) Urine Pellet

It is possible that bladder cancer cells slough off from the bladder lining into urine. To determine this possibility, we obtained urine pellet (containing potential bladder cancer cells). To do so, we centrifuged the thawed urine (i.e., 5,000 rpm for 5 min.) to obtain the urine pellets. The urine pellets were re-suspended in 1 ml of ice cold PBS. Urine pellets were solubilized by lysing the pellets in 40 of Lysis Buffer B (i.e., 50 mM Tris (pH 7.4), 250 mM NaCl, 0.5% NP-40, 1% Triton X-100). Urine pellet lysates were further incubated on ice for an additional 10 minutes. The lysates samples were centrifuged at 12,000 rpm for 10 minutes. Total protein in the urine lysates was quantified using a BCA assay kit (Pierce, Thermo Fisher Scientific, Rockford, Ill.) and protein concentration for each sample was adjusted to a range of 0.5-1.5 µg/µl. 30 µl of urine pellet lysate was analyzed for DEK protein expression in solubilized urine pellets using our Western blot assay with the polyclonal anti-DEK antibody (cat. no. A-301-335A) (detailed in Example 1). 10 µg of UroTSA cell lysate served as a control. 5 µl of the urine pellet lysate corresponding to 5 µg protein was resolved on 10% SDS-PAGE gel and stained with Coomassie blue.

Figure 5:
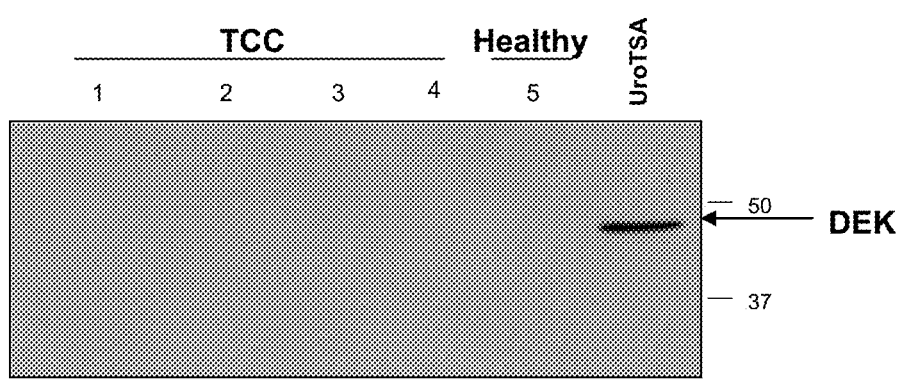
FIG. 5 depicts the expression of DEK protein in urine pellets obtained from four (4) bladder cancer patients (i.e., TCC) and a healthy individual in a Western blot assay. UroTSA serves as a control.
Figure 6:
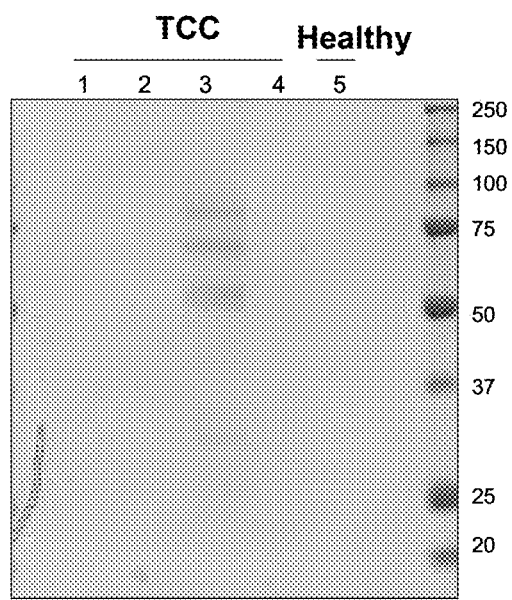
FIG. 6 depicts a Coomassie-blue stained 10% SDS-PAGE gel of proteins resolved from urine pellet lysates from four (4) bladder cancer patients (i.e., TCC) as well as a healthy individual.

FIG. 5 shows that DEK protein was not detected in the urine pellets of the patients suffering from bladder cancer or in the urine pellets of healthy patients using our Western blot assay. No protein was detected in the urine pellets of four (4) of the five (5) samples. (See, FIG. 6). This data suggests that DEK protein cannot be detected from the urine pellets by our Western blot assay.

b) Urine Supernatant

To determine if DEK protein may be secreted or released into urine, we tested neat urine supernatant for DEK protein expression using our Western blot assay. In this study, urine was obtained from two (2) patients suffering from transitional cell carcinoma (TCC) and from two (2) healthy subjects.

50 µl of neat urine supernatant from each of the two (2) patients suffering from TCC and the two (2) healthy patients was run in a Western blot assay using our polyclonal anti-DEK antibodies (cat. no. A-301-335A). 10 µg of cell lysate from T-24 bladder cancer cells served as a control.

Figure 7:
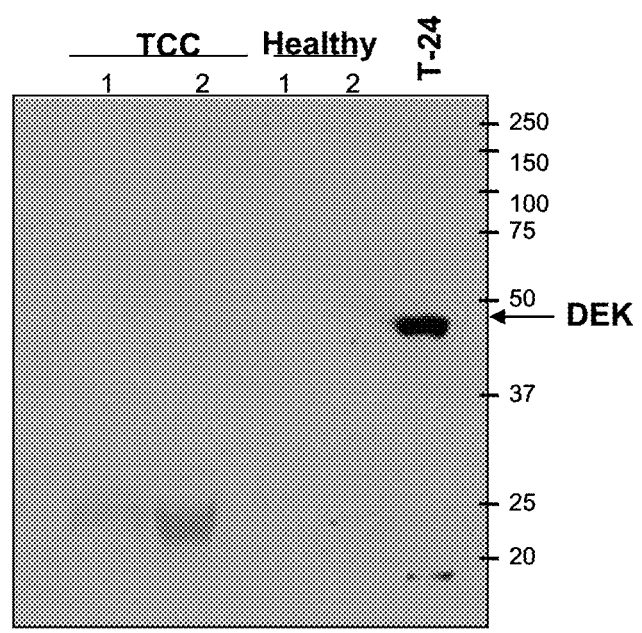
FIG. 7 depicts the expression of DEK protein in urine supernatant (neat) in a Western blot assay obtained from two (2) bladder cancer patients (i.e., TCC) and two (2) healthy individuals. Bladder cancer cell line T-24 serves as a control.

FIG. 7 shows that DEK protein was not detected in the neat urine supernatant of the two (2) patients suffering from TCC as well as from the two (2) healthy individuals.

To verify if there were indeed proteins present in the urine supernatants, we resolve total proteins on a 10% SDS-PAGE gel followed by staining with Coomassie blue.

Figure 8:
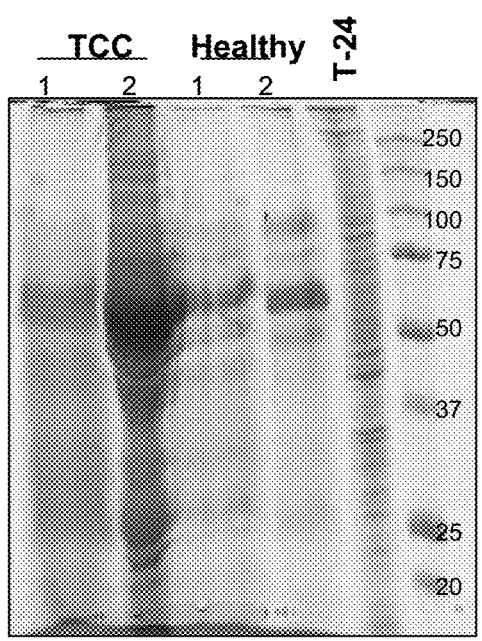
FIG. 8 depicts Coomassie-blue stained 10% SDS-PAGE gel of proteins resolved from the urine supernatant (neat) from two (2) bladder cancer patients (i.e., TCC), two (2) healthy individuals and bladder cancer cell T-24.

FIG. 8 clearly shows that there were abundant proteins present in each of the neat urine supernatants tested. Thus, we concluded that DEK protein could not be detected in neat urine supernatants from bladder cancer patients using Western blot assay.

Example 5 Western Blot Detection of DEK Protein in Concentrated Urine (by Filtration Method)

It is plausible that the neat urine may contain DEK protein that is in small amounts beyond the sensitivity of detection by our Western blot assay. To enhance DEK protein concentration in urine samples, we concentrated urine samples 10-fold using filtration method.

Urine samples from three (3) patients were used in this concentration study: (i) a patient suffering with bladder cancer (i.e., TCC), (ii) a patient with a history of prostate cancer (i.e., HxCAP), and (iii) a patient with a history of renal cell carcinoma (i.e., HxRCC).

500 µl of the thawed urine sample was concentrated 10-fold (i.e., to a final volume of 50 µl) using a Microcon® 3K filter (Millipore, Billerica, Mass.) (10,000 rpm, 10 min. at room temp.). All of the 50 µl of the 10-fold concentrated urine sample was analyzed for DEK protein expression on a Western blot assay, using the polyclonal anti-DEK antibody (cat. no. A-301-335A). UroTSA whole cell lysate (10 µg) served as a control.

Figure 9:
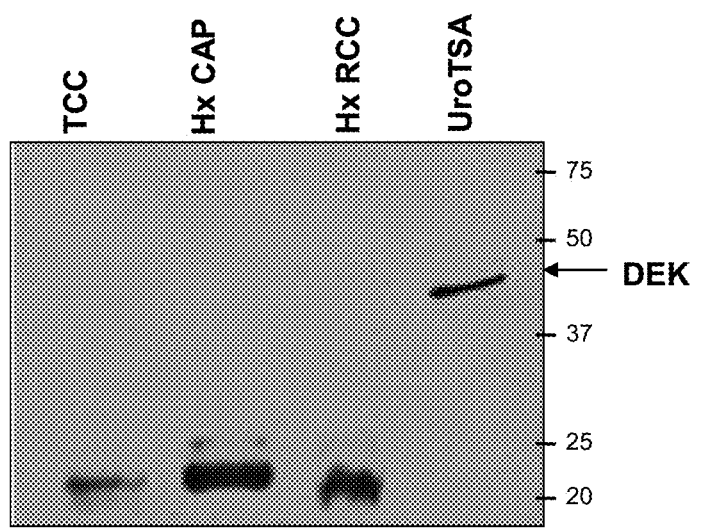
FIG. 9 depicts the expression of DEK protein in urine samples that were concentrated using a 3 kD filter as detected in a Western blot assay. Urine samples were obtained from one (1) patient with bladder cancer (i.e., TCC), one (1) patient with a history of prostate cancer (i.e., HxCAP), and one (1) patient with a history of renal cell carcinoma (i.e., HxRCC). UroTSA cell lysate was used as a control.

FIG. 9 shows that DEK protein was not detectable by Western blot assay even following 10-fold concentration of the urine samples by filtration method. This suggests that concentrating urine (e.g., by 10-fold) using filtration does not permit detecting DEK protein expression by our Western blot assay.

Example 6 Western Blot Detection of DEK Protein in Concentrated Urine (Chemical-Induced Precipitation)

We employed a different method to concentrate urine samples. In this study, we performed a chemical-induced precipitation method. Acetone was used as a chemical compound to cause protein precipitation in urine. Single acetone precipitation on urine samples was performed.

Potential coarse debris present in the thawed urine (25 ml) was removed by passing the thawed urine through a Kim-wipe® (Kimberly-Clarke Corp., Irving, Tex.). To induce precipitation, ice-cold acetone (volume to volume ratio of acetone to urine was 2.5:1) was added to the urine sample. Chemical-induced precipitation was permitted to occur by incubating the acetone-treated urine at −20° C. for 1 hour.

Acetone-induced precipitates were obtained by a brief centrifugation of the acetone-treated urine (12,000 rpm, 10 min). The precipitates were re-suspended in a buffer containing sucrose (sucrose buffer) (i.e., 10 mM triethanol amine containing 250 mM sucrose) in 500 µL volume. This volume of sucrose buffer was found to be effective in re-suspending the precipitates to solution (i.e., completely dissolve the residues). Therefore, the acetone-induced precipitation caused the urine proteins to increase to a 50-fold concentration.

We obtained urine samples from four (4) different patient groups: (i) a patient with renal cell carcinoma (i.e., RCC); (ii) a patient with prostate cancer (i.e., CAP), (iii) a patient with benign enlarged prostate (i.e., BPH); and, (iv) a patient with transitional cell carcinoma (i.e., TCC).

The total proteins in the sucrose-buffer re-suspended urine precipitates were quantified using a BCA assay kit (Pierce, Thermo Fisher Scientific, Rockford, Ill.). 50 µg of protein (i.e., 50-80 µl) was used to run on a Western blot assay using our polyclonal anti-DEK antibody (cat. no. A-301-335A). UroTSA whole cell lysate (10 µg) served as a control.

Figure 10:
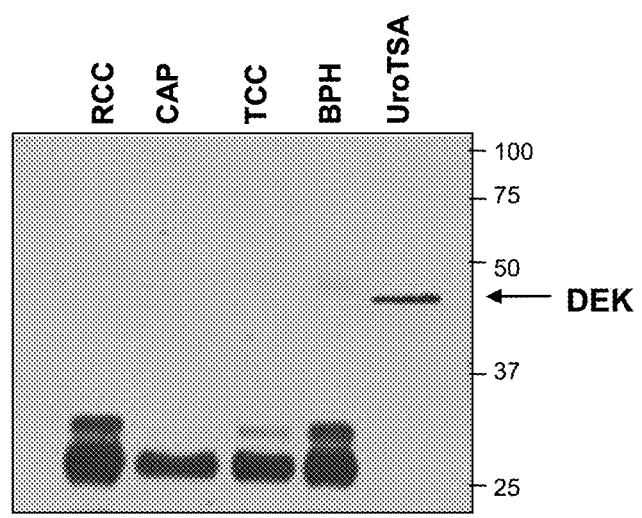
FIG. 10 depicts the expression of DEK protein in urine samples that were treated with acetone to obtain precipitates. The re-suspended precipitates were subjected to a Western blot assay to detect DEK protein. Urine samples were obtained from one (1) patient with renal cell carcinoma (i.e., RCC), one (1) patient with prostate cancer (i.e., CAP), one (1) patient with bladder cancer (i.e., TCC), and one (1) patient with a benign enlarged prostate (i.e., BPH). UroTSA cell lysate was used as a control.

FIG. 10 shows that DEK protein was not detected by our Western blot assay in the concentrated urine samples (e.g., 50-fold concentrated urine by acetone precipitation).

In parallel, 20 µg of acetone-precipitated urine proteins were resolved on a 10% SDS-PAGE gel and stained with Coomassie stain to test for the presence of protein in the samples.

Figure 11:
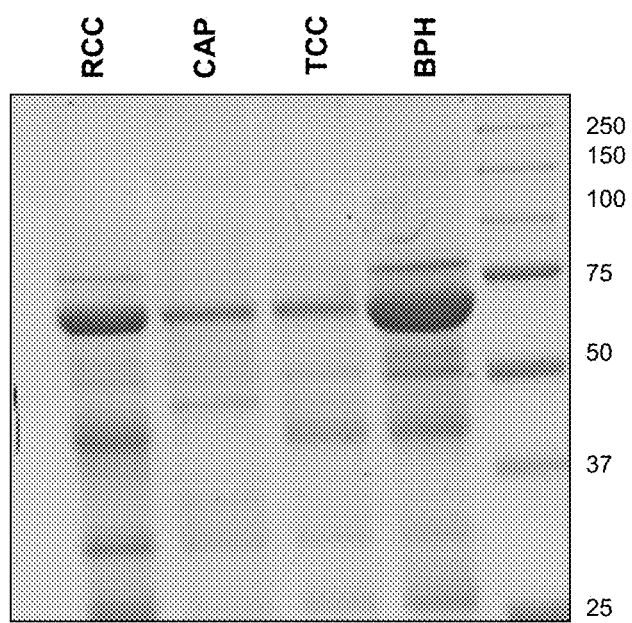
FIG. 11 depicts Coomassie-blue stained 10% SDS-PAGE gel of the proteins resolved from acetone precipitated urines from one (1) patient with renal cell carcinoma (i.e., RCC), one (1) patient with prostate cancer (i.e., CAP), one (1) patient with bladder cancer (i.e., TCC), one (1) patient with benign enlarged prostate (i.e., BPH) and UroTSA cell lysates.

FIG. 11 clearly shows that proteins were present in each of the tested concentrated urine samples. This result indicates that acetone-induced concentration of urine proteins (i.e., by 50-fold) is not sufficient to permit detection of DEK protein expression by our Western blot assay.

Example 7 Western Blot Detection of DEK Protein in Consecutively Chemical-Induced Precipitation of Urine We further assessed if multiple chemical-induced precipitations (e.g., acetone) would permit detection of DEK protein expression by our Western blot assay. We repeated the same experiment as detailed above in Example 6. After the single acetone precipitation, and re-suspension of the precipitates in 500 µL of sucrose buffer.

10 ml PBS was added to the re-suspended precipitates to form PBS solution prior to performing a second acetone precipitation. To the 10 ml PBS solution we added a 2.5× volume of acetone (i.e., 25 ml ice-cold acetone) (vol/vol of acetone to PBS solution was 2.5:1).

The final pellet was re-suspended in 600 µl of sucrose buffer (10 mM Tri-ethanolamine and 250 mM Sucrose). The amount of protein in each sample was quantified using a BCA assay kit (Pierce, Thermo Fisher Scientific, Rockford, L). 50 µg of protein (50-80 µl) was run on a Western blot assay.

We tested ~100 µg total protein of the single acetone precipitated samples and 100 µg total proteins from the double acetone precipitated samples by Western blot analysis using polyclonal anti-DEK antibody. UroTSA cell lysate (10 µg) served as a control.

Figure 12:
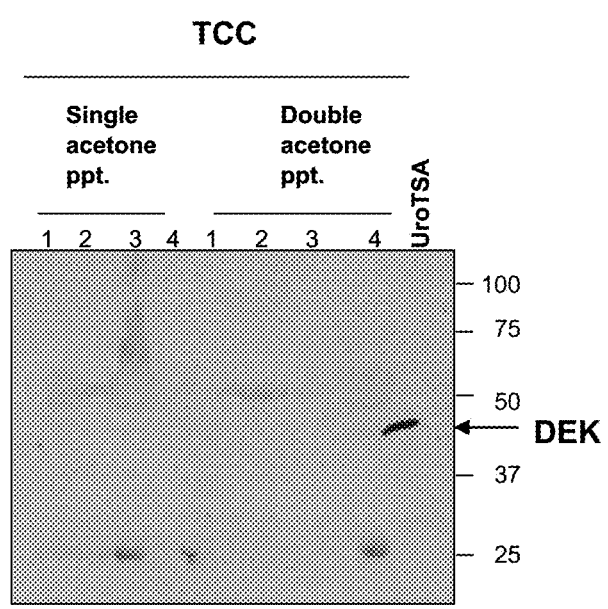
FIG. 12 depicts the expression of DEK protein as detected by Western blot assay in urine samples that were treated with acetone to obtain precipitates. Urine samples were obtained from four (4) bladder cancer patients (i.e., TCC). Samples were tested after a single protein precipitation with acetone (i.e., single acetone ppt.) and after a second protein precipitation with acetone (i.e., double acetone ppt.).
Figure 13:
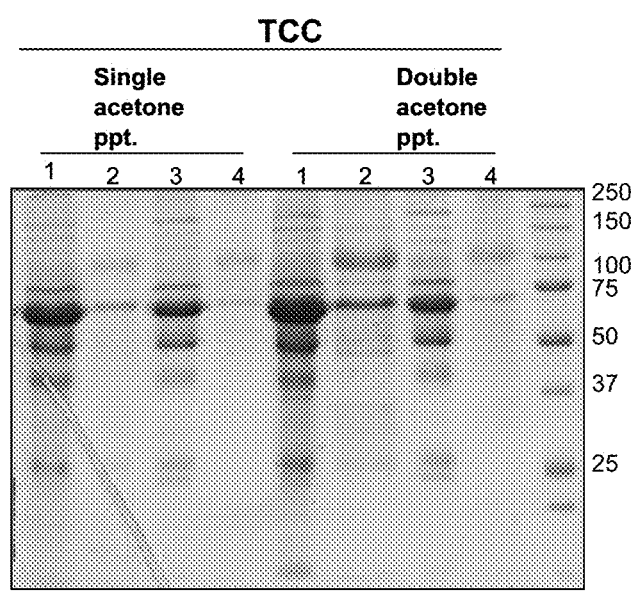
FIG. 13 depicts Coomassie-blue stained 10% SDS-PAGE gel of the proteins resolved from urine samples subjected to single (i.e., Single acetone ppt.) and double acetone precipitation (i.e., Double acetone ppt.). Urine samples were obtained from four (4) bladder cancer patients (i.e., TCC).

FIG. 12 demonstrates that DEK protein was not detected in any of the tested samples, whether single or double acetone precipitated. Proteins were, however, detected in all samples run on a 10% SDS-PAGE gel and stained with Coomassie blue (See, FIG. 13). This suggests that multiple chemical-induced precipitations of urine samples do not permit detection of DEK protein by Western blot assay.

Example 8 Western Blot Detection of DEK Protein in Concentrated Urine after Filtration-Induced Concentration Followed by Chemical-Induced Precipitation In this example, we examined if a combination of filtration-induced concentration method and chemical-induced precipitation method would further lead to concentration of urine samples and thus would permit DEK protein detection by our Western blot assay.

In this series of study, we concentrated urine samples by: (i) first subjecting the urine samples to filtration-induced concentration protocol (i.e., concentrating urine samples with a 30K Amicon® column), and (ii) then subjecting the filter-concentrated urine samples to a chemical-induced precipitation (i.e., a single acetone precipitation).

Urine samples from two (2) transitional cell carcinoma (i.e., TCC) patients were used in this study. 15 ml urine was filtered with a 30K Amicon® column by spinning the column at 6,000 rpm for 30 min. This filtration-induced concentration method caused the urine sample to undergo a 30-fold increase in concentration (i.e., from 15 ml to 500 µl). The 500 µl samples were re-suspended in 10 ml phosphate buffer saline (PBS).

The 10 ml re-suspended solution was then treated with ice-cold acetone (i.e., 2.5 volume of acetone was added to the solution to cause precipitation) (See, acetone-induced precipitation protocols as detailed in Example 6). The chemical-induced precipitation further resulted in an additional 20-fold increase in concentration. Protein was quantified using BCA assay.

Figure 14:
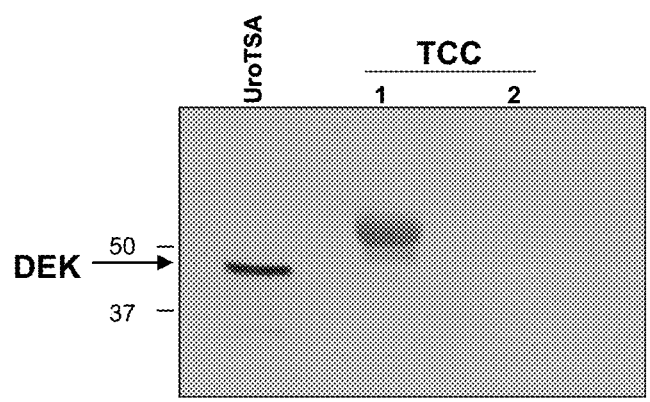
FIG. 14 depicts the expression of DEK protein in urine treated first by filtration with a 30 kD cut-off membrane filter followed by acetone precipitation as detected by Western blot assay. Urine was obtained from two (2) patients suffering from bladder cancer (i.e., TCC). UroTSA cell lysate was used as a control.

50 µg (~90 µL) was analyzed for the presence of DEK protein in our Western blot assay using the polyclonal anti-DEK antibody (cat. no. A-301-335A). UroTSA cell lysate (10 µg) was used as a control. FIG. 14 shows that DEK protein was not detected by our Western blot assay in either of the two TCC samples.

Figure 15:
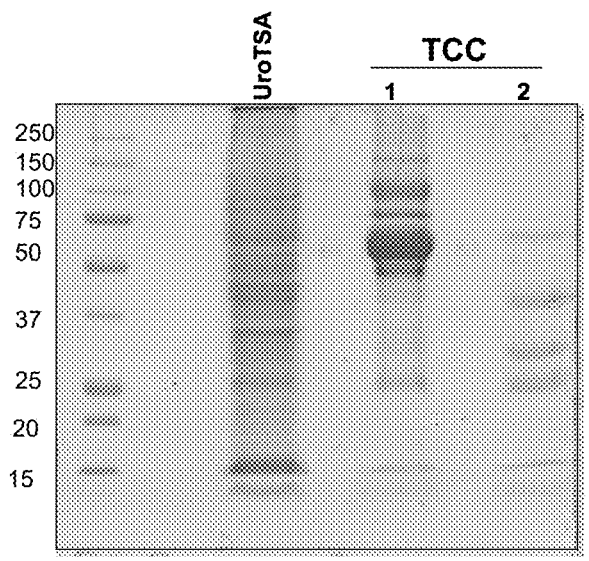
FIG. 15 depicts Coomassie-blue stained 10% SDS-PAGE gel of the proteins resolved from urine treated by filtration with a 30 kD cut-off membrane filter followed by acetone precipitation. Samples from two (2) patients suffering from bladder cancer (i.e., TCC) and UroTSA cell lysate were tested.

20 µg of each sample was run on a 10% SDS-PAGE gel to test for the presence of protein in the samples. Proteins were detected in the samples as shown by the Coomassie blue stained 10% SDS-PAGE gel. (See, FIG. 15). This data indicates that concentrating urine by first filtration-induced method followed by chemical-induced method (i.e., acetone precipitation) still does not permit DEK protein detection by Western blot assay (despite a 600-fold increase in protein concentration of urine).

Example 9 Western Blot Detection of DEK Protein in Concentrated Urine after Filtration-Induced Concentration Followed by Three Consecutive Chemical-Induced Precipitations In this example, we examined if a combination of filtration-induced concentration method and consecutive chemical-induced precipitations may further concentrate urine samples and thus permit detection of DEK protein expression in our Western blot assay.

In this experiment, urine samples were: (i) first concentrated by filtration protocol (i.e., concentrating urine samples with a 30K Amicon® column), and (ii) then concentrated by a consecutive (3×) chemical-induced precipitations (i.e., acetone precipitation). Specifically, urine sample (15 ml) from one (1) patient with bladder cancer (i.e., TCC) was concentrated with a 30K Amicon® column (spinning at 6,000 rpm for 30 min.). This filtration-induced concentration method caused the urine sample to undergo a 100-fold increase in concentration (i.e., from 15 ml to 150 µl). The 100-fold concentrated urine sample was diluted with 10 ml PBS to form a solution (PBS solution).

Then, the PBS solution (containing the concentrated urine sample after the filtration step) was then subjected to three (3) consecutive chemical-induced precipitations (i.e., acetone precipitation). Specifically, ice-cold acetone (volume to volume of acetone to concentrated urine sample was 4:1) was added to the samples to cause precipitation (i.e., adding 40 ml acetone to the 10 ml PBS solution). The mixture was chilled for an additional one (1) hour at −20° C. The mixture was centrifuged (12,000 rpm for 5 min.) to collect the precipitates. The resulting precipitates were re-suspended in 500 µl of buffer A (50 mM Tris (pH 7.4), 0.5% NP-40, 1% Triton X-100). Note that buffer A contains a low salt content (preferably <100 mM NaCl) because a high salt concentration (e.g., >250 mM NaCl) is shown to adversely affect protein migration in a Western blot gel.

The acetone precipitation was repeated (i.e., a total of three times). Each time, the precipitates were re-suspended in 10 mL PBS prior to acetone addition. The final acetone precipitates were re-suspended in 50 µL of buffer A. The present combination of filtration-induced concentration method and consecutive 3× chemical-induced precipitations resulted in an increase of concentration of a total of 300-fold.

Figure 16:
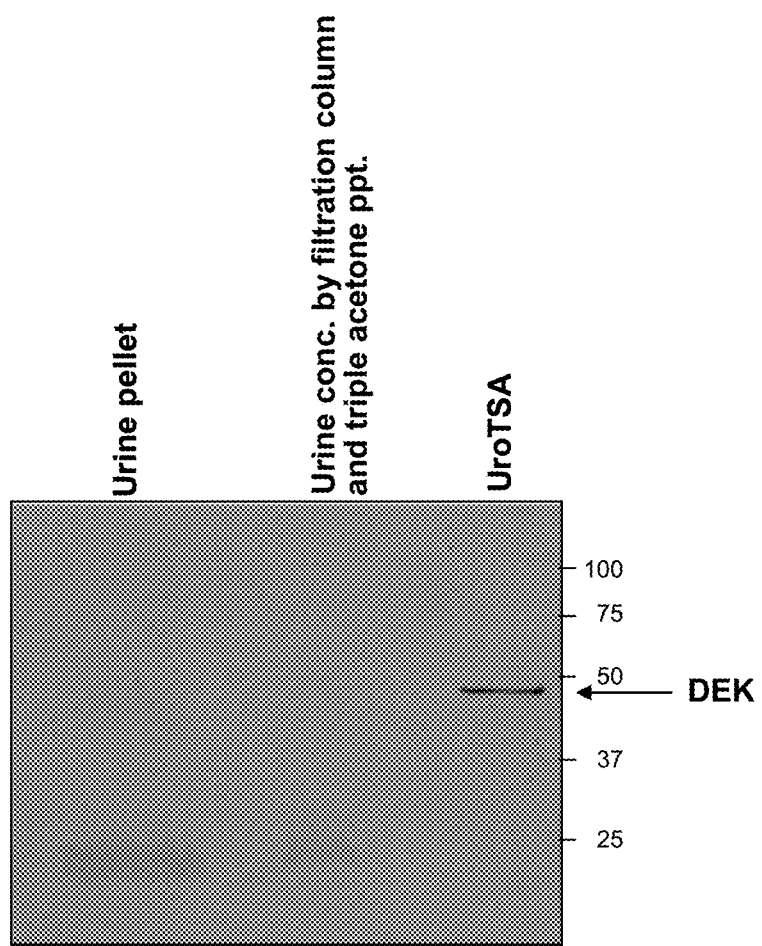
FIG. 16 depicts the expression of DEK protein in urine treated first by filtration with a 30 kD cut-off membrane filter followed by consecutive triple (3×) acetone precipitations. Urine was obtained from one (1) patient suffering from bladder cancer (i.e., TCC). Expression of DEK protein in these urines was tested by Western blot assay. UroTSA cell lysate was used as a control.

50 µL of the sample was analyzed in our Western blot assay using the polyclonal anti-DEK antibody. FIG. 16 shows that DEK protein was still not detected by our Western blot assay, despite a 300-fold increase in concentration. Similarly, no DEK protein was detected in the urine pellet (FIG. 16).

Example 10 Western Blot Detection of DEK Protein in Concentrated Urine after Chemical-Induced Precipitation Followed by Filtration-Induced Concentration In this example, we examined if the sequence of the concentration protocols may permit the detection of DEK protein expression in our Western blot assay.

To test this theory, we employed urine samples from seven (7) patients suffering from transitional cell carcinoma (i.e., TCC), six (6) patients suffering from prostate cancer (i.e., CAP), five (5) patients suffering from renal cell carcinoma (i.e., RCC) and one (1) patient with a history of transitional cell carcinoma (i.e., HxTCC).

Contrary to the sequence order of the concentration protocols detailed in Example 9, the urine samples were: (i) first concentrated by a chemical-induced precipitation method (i.e., a single acetone precipitation), and (ii) then concentrated the urine samples by a filtration method (i.e., concentrating urine samples with a 3K Microcon® filter.

Specifically, 20 ml of urine was treated with two (2) volumes (i.e., 40 mL) of ice-cold acetone. Samples were chilled for an additional one (1) hour at −20° C. and centrifuged briefly (12,000 rpm for 10 min.) to collect the precipitates (i.e., to obtain a pellet). The pellet was re-suspended in 2 mL of sucrose buffer (i.e., 10 mM Tri ethanol amine and 250 mM sucrose). This acetone-induced precipitation caused an increase in concentration of urine proteins of 10-fold (i.e., from 20 mL to 2 mL).

400 µL of the re-suspended urine sample was further concentrated using a 3K Microcon® filter. Samples were spun at 10,000 rpm for 10 minutes to obtain a final volume of ~100 µL (i.e., an additional 4-fold increase in concentration). Therefore, the combination of acetone-induced precipitation followed by filtration caused a total of 40-fold increase in concentration of urine. 30 µL of concentrated urine sample was analyzed by our Western blot assay using polyclonal anti-DEK antibody.

Figure 17:
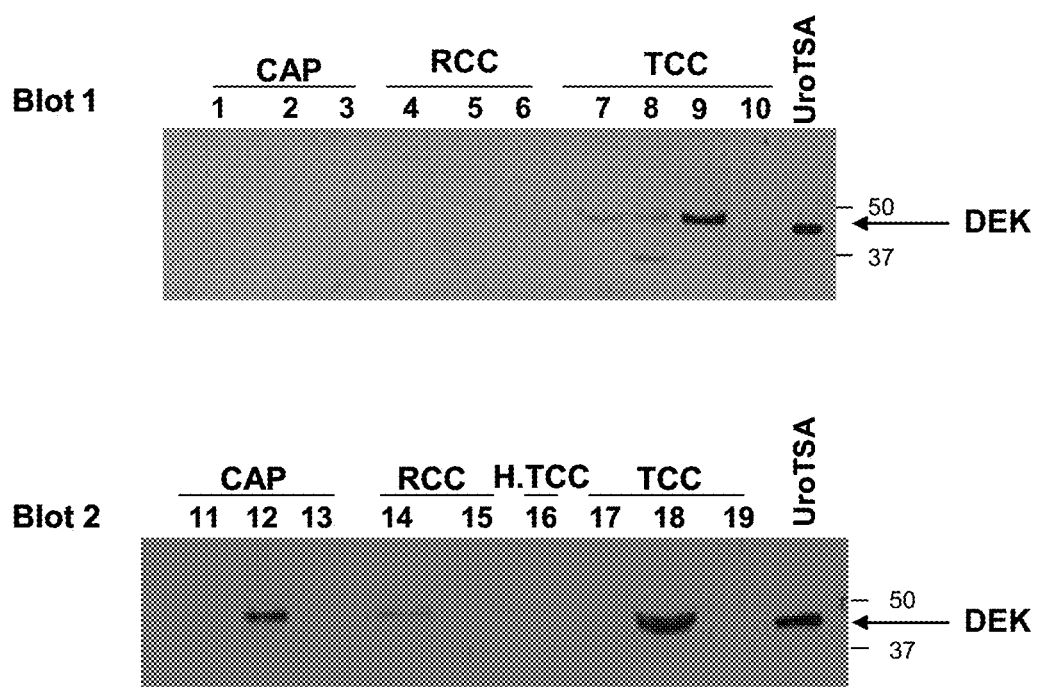
FIG. 17 depicts the expression of DEK protein in urine concentrated first by acetone precipitation and then filtered with a 3 kD cut-off membrane filter as detected in a Western blot assay. Urine was obtained from six (6) patients suffering from prostate cancer (i.e., CAP), five (5) patients suffering from renal cell carcinoma (i.e., RCC), seven (7) patients suffering from transitional cell carcinoma (i.e., TCC) and one (1) patient with a history of transitional cell carcinoma (H.TCC). UroTSA cell lysate was used as a control.

FIG. 17 shows DEK protein expression in the concentrated urine samples. DEK protein expression was clearly detected in four (4) of the seven (7) TCC patient samples (i.e., lanes 7, 8, 9, 18), in one (1) of the five (5) RCC patient samples (i.e., lane 14), and in one (1) of the six (6) CAP patient samples (i.e., lane 12). DEK protein was not detected in the patient with a history of TCC (i.e., lane 16).

These results were unexpected and surprising. And they represent the first report that DEK protein could be detected in urine samples of bladder cancer patients using a Western blot assay. The success of DEK protein detection resides on the unique sequence of urine concentrations (i.e., first by a chemical-induced precipitation method followed by a filtration method).

Example 11 Patient Study—Western Blot Detection of DEK Protein Expression in Urine from Bladder Cancer Patients Using the sequential concentration protocols detailed in Example 10, we next analyzed DEK protein expression in bladder cancer patient urine samples. This study is aimed to provide a correlation between urine DEK protein expression and the development of bladder cancer in humans.

Urine was collected from eight (8) patient groups: (i) fourteen (14) patients with varying grades of transitional cell carcinoma (i.e., TCC), (ii) eight (8) patients with prostate cancer (i.e., CAP), (iii) four (4) patients with renal cancer (i.e., RCC), (iv) three (3) nonmalignant urologenital disease (including one (1) patient suffering from cystitis and (2) suffering from chronic inflammation), (v) one (1) patient suffering from renal oncocytoma, (vi) one (1) patient suffering from renal cystic nephroma, (vii) one (1) patient that had undergone radical cystemectomy (no tumor found), and (viii) five (5) healthy individuals.

A total of thirty-six (36) urine samples (20 ml each) from the eight (8) patient groups were evaluated. Urine was sequentially concentrated using the acetone-precipitation method followed by the filtration method as described in Example 10 (above). The concentrated urine was then analyzed using our Western blot assay with the polyclonal anti-DEK antibody.

Table 2 summarizes the DEK protein expression in our Western blot assay. In brief, we detected DEK protein expression in the urine of fifteen (15) of the nineteen (19) bladder cancer patients (i.e., TCC). DEK protein expression was not detected in the urine of healthy individuals. In addition, DEK protein expression was not detected in the urine of twelve (12) of the sixteen (16) individuals that were suffering from non-bladder cancer ailment (e.g., CAP, RCC, chronic inflammation, cystitis).

TABLE 2

DEK Protein in Urine Samples from Bladder Cancer Patients

| Urine Sample Source | DEK Western Blot |
|---|---|
| TCC Ta low grade (I) | positive |
| TCC Ta low grade (I-II) | positive |
| TCC Ta low grade (I) with squamous differentiation | positive |
| TCC Ta low grade (II) | negative |
| TCC Ta low grade (I) | positive |
| TCC Ta low grade (I) | positive |
| TCC Ta low grade (I-II) | positive |
| TCC Ta low grade (I) with squamous differentiation | positive |
| TCC Ta low grade (I) | positive |
| TCC Ta low grade (I) | negative |
| TCC T1 low grade | negative |
| TCC T1 high grade with papillary + solid pattern | positive |
| TCC T1 high grade(III) + CIS with solid pattern | positive |
| TCC T1 high grade | positive |
| TCC T2 high grade + CIS | positive |
| TCC T2 high grade | positive |
| TCC T2 high grade (III) | positive |
| TCC T2 high grade (III) & papillary RCC type1 | negative |
| TCC T2 high grade (III) | positive |
| TCC inconclusive pathology | negative |
| Chronic inflammation (history of TCC) | positive |
| No tumor on radical cystectomy (history of TCC) | negative |
| CAP | negative |
| CAP | positive |
| CAP | negative |
| CAP | negative |
| CAP | negative |
| CAP | negative |
| CAP | negative |
| RCC | negative |
| RCC | negative |
| RCC | positive |
| RCC | positive |
| Renal oncocytoma | negative |
| Renal cystic nephroma | negative |
| Cystitis | negative |
| Chronic inflammation | negative |
| Healthy | negative |
| Healthy | negative |
| Healthy | negative |
| Healthy | negative |
| Healthy | negative |
| Healthy | negative |

Figure 18:
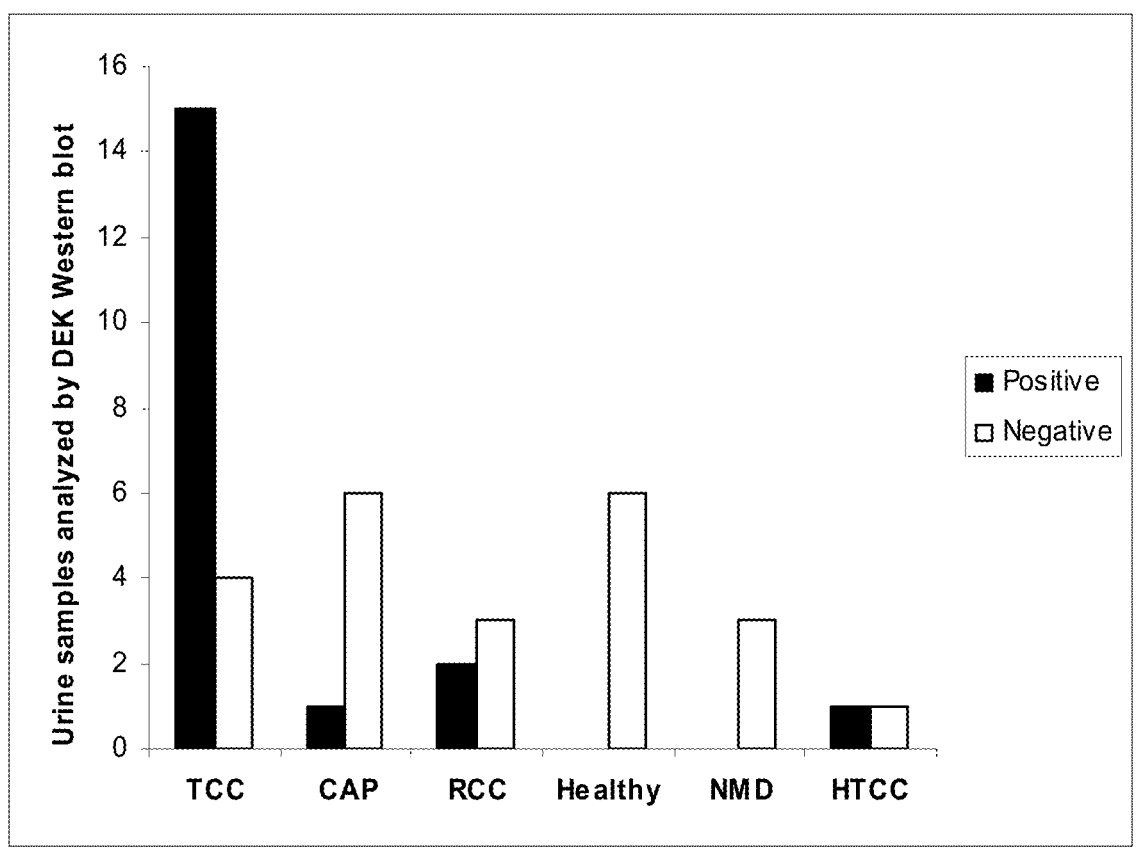
FIG. 18 depicts the number of urine samples per patient groups (i.e., TCC, CAP, RCC, NMD, and HTCC) that tested positive for DEK in urine samples by a Western blot assay.

FIG. 18 shows the graphical representation of DEK Western blot results presented in Table 2.

Altogether, this data demonstrates that DEK protein is present in the urine of bladder cancer patients. It is detected in both low grade and high grade bladder cancer patients. DEK protein is not found either in the urine of healthy individuals or in the urine of non-bladder cancer patients, indicating specificity of DEK protein as a biomarker for bladder cancer.

Overall, the present method of detecting DEK protein in urine has a high sensitivity (79%) and specificity (83%). The presence of DEK protein in urine is a viable method for detecting and diagnosing bladder cancer in humans.

Example 12 Conductivity of Urine Samples

In this series of studies, we examined the potential mechanistic basis for whether filtration or acetone-induced precipitation of urine may change the salt concentrations in the urine. It is our contention that an alteration of salt concentrations in urine may affect the outcome of DEK protein detection in our Western blot analysis (e.g., imparting a conformational change in DEK protein).

To do so, we measured the conductivity of the urine before and after the filtration and acetone-induced precipitation. It has been established that conductivity of urine is an indication of salt concentrations (e.g., high conductivity means a high salt concentration and low conductivity means a low salt concentration).

We processed urine samples as described in Examples 4b, 5, 6, 7, 8, 9, 10 and 11. 50 µL of each sample was added to 5 mL of de-ionized water. Conductivity was determined using a conductivity meter (Traceable Expanded-Range Conductivity Meter, VWR, model no. 89094-958). Conductivity results are summarized in Table 3.

TABLE 3

Conductivity Values for Urine Samples

| Processing Methods | Conductivity (µS/cm) |
| --- | --- |
| None (Example 4b: Neat Urine) | 132 |
| Microcon ® 3K Filtration (Example 5) | 146 |
| Single Acetone Precipitation (Example 6) | 110 |
| Consecutive Acetone Precipitations (Example 7) | 185 |
| 30K Amicon ® Filtration followed by a Single Acetone Precipitation (Example 8) | 114.9 |
| 30K Amicon ® Filtration followed by Three Consecutive Acetone Precipitations (Example 9) | 27.6 |
| Acetone Precipitation followed by Microcon ® 3K Filtration (Example 10) | 170.6 |

Conductivity in urine samples was decreased after acetone precipitation (1×) (i.e., Example 6), after filtration with a 30K Amicon® column followed by a single acetone precipitation (i.e., Example 8), and after filtration followed by a consecutive (3×) acetone precipitations (i.e., Example 9).

Conductivity in urine samples was increased after filtration with a Microcon® 3K column (i.e., Example 5), after consecutive (3×) acetone precipitation (i.e., Example 7), and after acetone precipitation followed by filtration (i.e., Example 10).

Because DEK protein is only found to be present in the urine after acetone-induced precipitation followed by filtration, the conductivity data (in Table 3) does not provide a mechanistic basis for our finding. There is no clear pattern or trend of urine conductivity between filtration and acetone-induced precipitation.

Example 13 Expression and Purification of Recombinant DEK Protein in the Bacterial BL-21 Cells In this series of study, we sought to recombinantly express the DEK isoform 1 and develop a capture ELISA for specific detection of DEK isoform 2.

a) cDNA and Construction of Expression Plasmid

Figure 19:
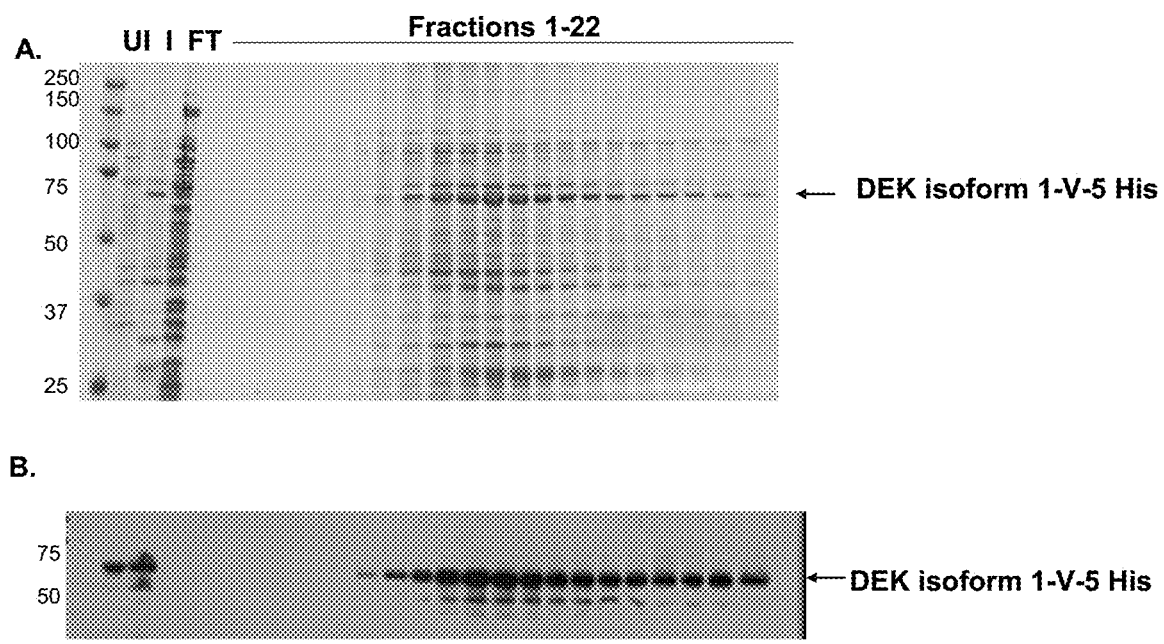
FIG. 19 depicts the recombinant expression of DEK isoform 1 protein as V-5 tagged protein. Total proteins were stained by Coomassie blue and DEK isoform 1 detection was performed by Western Blot using an V-5 antibody

DEK cDNA was cloned and expressed using the Gateway® system (Invitrogen). Briefly, the cDNA of the wild-type DEK isoform 1 was obtained by the PCR amplification and cloned into pENTR™5' TOPO® vector (Invitrogen; Carlsbad Calif.) (See Experimental Methods & Protocols). The nucleotide sequence for DEK isoform 1 cDNA was verified by DNA sequencing.

pENTR-DEK was recombined with DEST® vector (pBAD-DEST®) by LR recombinase to obtain a DEK as a V-5 tagged protein upon expression. The nucleotide sequence for DEK was again verified by sequencing.

b) Bacterial Expression of Recombinant DEK Isoform 1 Protein pBAD-DEST®-DEK was transformed into BL-21 bacterial cells. DEK isoform 1 protein was expressed upon induction of transformed BL-21 cells with 0.2% L-arabinose at stationary phase. Protein expression was confirmed by Western blot analysis of induced cells using a V-5 antibody and DEK monoclonal antibody.

c) Purification of Recombinant DEK-V5 Protein from the Bacterial Cells 500 mL culture of BL-21 cells transformed with pBAD-DEST®-DEK was induced with 0.2% L-arabinose at stationary phase of bacterial growth for 2 hours at 30° C. Cells were pelleted and re-suspended in BugBuster™ Protein Extraction Reagent (Novagen) and sonicated. Bacterial cell extract was loaded on a Nickel-Column and DEK-V5-his was eluted using 250 mM imidazole. Fractions were loaded on 10% SDS-PAGE gel and stained with Coomassie-blue (See, FIG. 19A) and subjected to Western blot analysis using a V-5 monoclonal antibody (Invitrogen) (See, FIG. 19B).

Example 14 ELISA Assay to Detect DEK

To determine whether the DEK protein is present in urine of patients suffering from bladder cancer, we developed an ELISA assay to detect DEK. In the following series of studies, we examined if DEK protein could be detected in the urine of patients with transitional cell carcinoma of the bladder. In order to do so, we first developed a capture and indirect ELISA using healthy urine samples that were spiked with various concentration of recombinant DEK isoform 1 protein.

a) ELISA Development

Using the recombinant DEK isoform 1 proteins prepared (detailed above), we proceeded to develop an ELISA sandwich system. The ELISA system allows detection of the DEK protein. In this ELISA system, two anti-DEK antibodies are used, each antibody recognizing different epitopes on DEK protein.

b) Capture Antibody and Detection Antibody

In one of our ELISA assay, a rabbit anti-human DEK polyclonal antibody (16448-1-AP, ProteinTech Group, Chicago, Ill.) was used as a capture antibody (the polyclonal antibody was raised against full-length DEK). And, a mouse anti-human DEK monoclonal antibody (the monoclonal antibody was raised against the amino acids 19-169 of the DEK protein) was used as a detection antibody.

c) ELISA Sandwich

Figure 20:
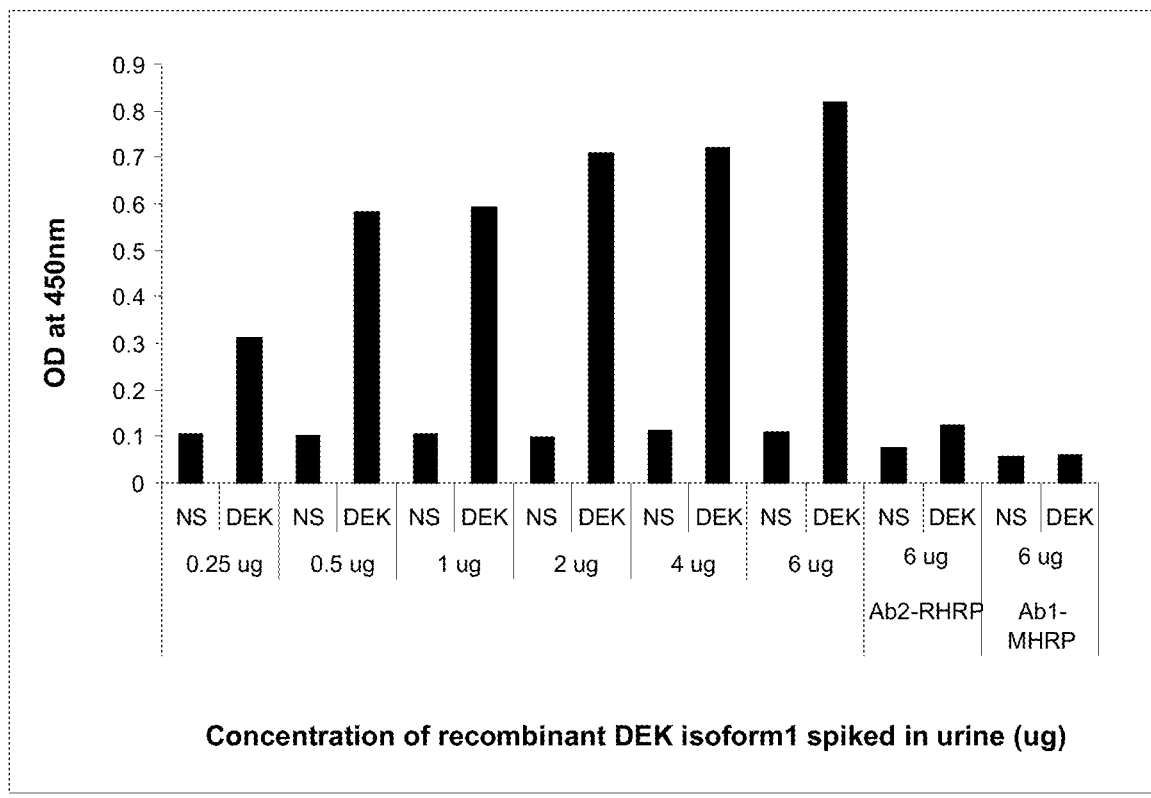
FIG. 20 depicts the ELISA sandwich using two (2) different anti-human DEK antibodies. A rabbit polyclonal anti-human DEK antibody (used as capture antibody) was coated on the solid support (e.g., microtiter plate) to capture DEK protein. The capture antibody specifically captured the DEK protein in spiked urine sample (i.e., recombinant DEK isoform 1 protein added to control urine sample) on the ELISA plate. The captured DEK protein was then detected by a mouse monoclonal anti-DEK antibody. The antibody-antigen sandwich was detected by anti-mouse IgG conjugated with horseradish peroxidase (HRP). The horseradish peroxidase activity (representing the level of DEK) was measured by addition of tetramethylbenzidine (TMB) substrate. The color intensity was in direct proportion to the amount of the DEK protein. Color development was stopped and the intensity of the color was measured at optical density (OD) 450 nm on a microtiter plate reader.

FIG. 20 depicts an ELISA sandwich using two (2) different anti-human DEK antibodies. In this series of study, the rabbit anti-human DEK polyclonal antibody (16448-1-AP) was used as capture antibody and was coated on the solid support (e.g., microtiter plates) in order to capture DEK protein in spiked urine samples (i.e., control urine samples that were spiked with various concentrations of recombinant DEK isoform 1 protein. The captured DEK was then detected by a mouse anti-human DEK monoclonal antibody (BD Biosciences).

d) Detection System

The antibody-antigen sandwich was detected by an anti-mouse IgG conjugated with horseradish peroxidase (HRP), which specifically recognize mouse IgG. The peroxidase activity (representing the level of DEK captured onto plates) was measured by addition of a tetramethylbenzidine (TMB) substrate. The color intensity was directly proportion to the amount of the bound DEK protein. Color development was stopped by adding 1 M $H_2SO_4$ and the intensity of the color was measured at optical density (OD) 450 nm using a microtiter plate reader.

e) Validation of Capture ELISA Using Recombinant DEK Isoform 1 Protein

FIG. 20 depicts the ELISA that was developed. Recombinant DEK isoform 1 protein was spiked in healthy urine sample. The developed ELISA detects the DEK protein in the spiked urine sample.

f) Validation of Capture ELISA Using Cell Lysates from Bladder Tumor Tissue

Figure 21:
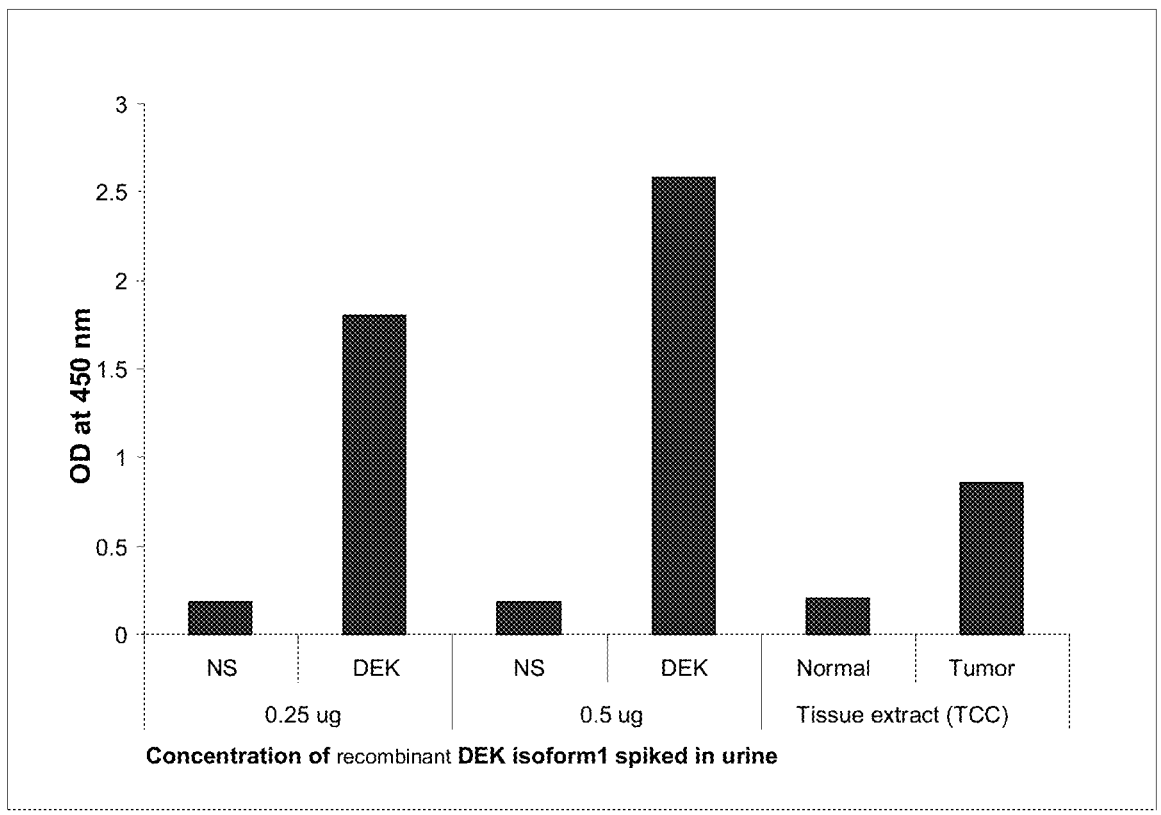
FIG. 21 depicts the validation of a developed ELISA using 50 µg of tissue lysates prepared from bladder tumor tissue and adjacent normal tissue.

FIG. 21 depicts detection of DEK protein in 50 µg of cell lysates that were prepared from bladder tumor tissues. In contrast, DEK protein was not detected in cell lysates obtained from adjacent normal bladder tissues from a TCC patient, indicating that the developed ELISA can specifically detects DEK in human bladder tumor tissues.

Example 15 ELISA Fails to Detect DEK in Urine Samples after Acetone Precipitation So far, we have successfully detected DEK proteins in urines spiked with recombinant EK isoform 1 protein and in cell lysates obtained from human bladder tumor tissues using the developed capture ELISA. As clearly shown in Examples 10 and 11, our Western blot assay detected DEK protein in urines obtained from patients suffering from bladder cancer. In these studies detailed in Examples 10 and 11, urine samples were subjected to acetone precipitation followed by filtration-induced concentration.

Figure 22:
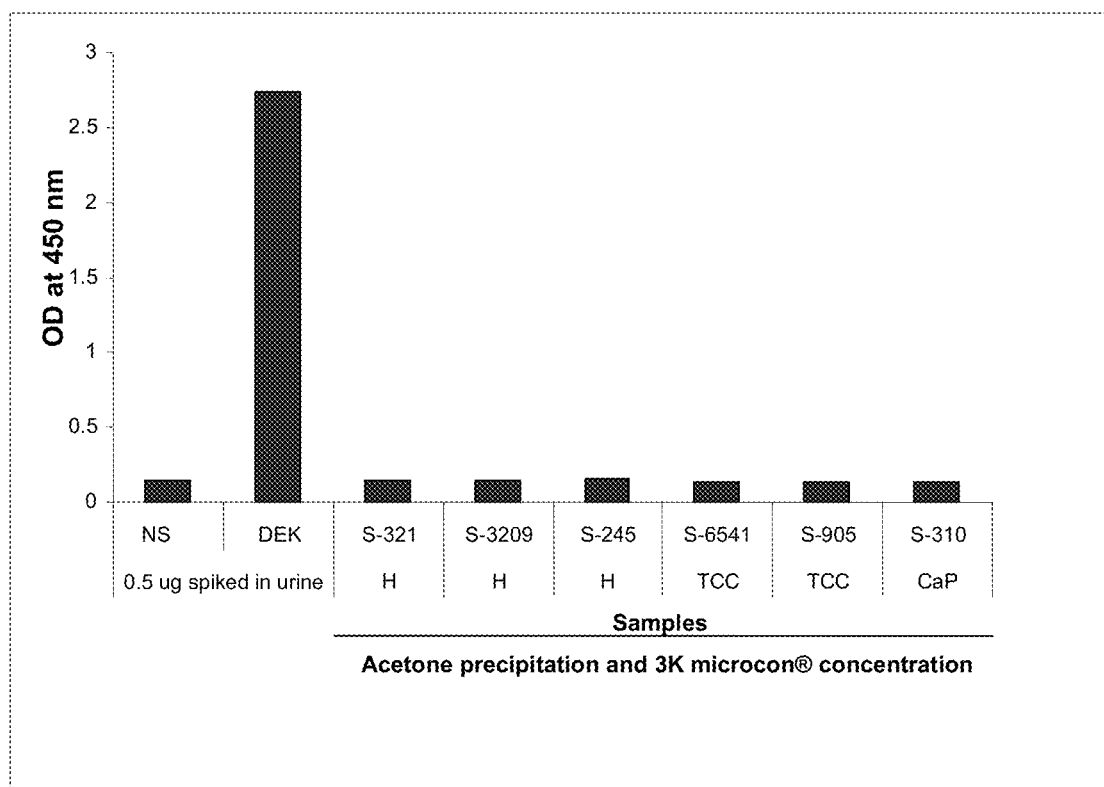
FIG. 22 depicts a failed experiment in detection of urine DEK from TCC patients by capture ELISA. Urine samples were subjected to acetone precipitation followed by Microcon® concentration from TCC patients. The urine samples from these TCC patients have been tested positive for DEK expression by Western blot. Noted that the same urine samples, when evaluated for DEK presence using capture ELISA, failed to show any DEK protein.

To our surprise, when employed the developed capture DEK ELISA, we could not detect DEK protein in the urine samples obtained from the same TCC patients. (See, FIG. 22). In contrast to the ELISA, DEK is detectable using our Western blot assay. We reasoned that the discrepancy may relate to the hypothesis that ELISA is sensitive to protein that undergoes denaturation. It is believed that DEK may undergo denaturation after acetone precipitation.

Example 16 Acetone Precipitation is Inhibitory for Capture ELISA

Figure 23:
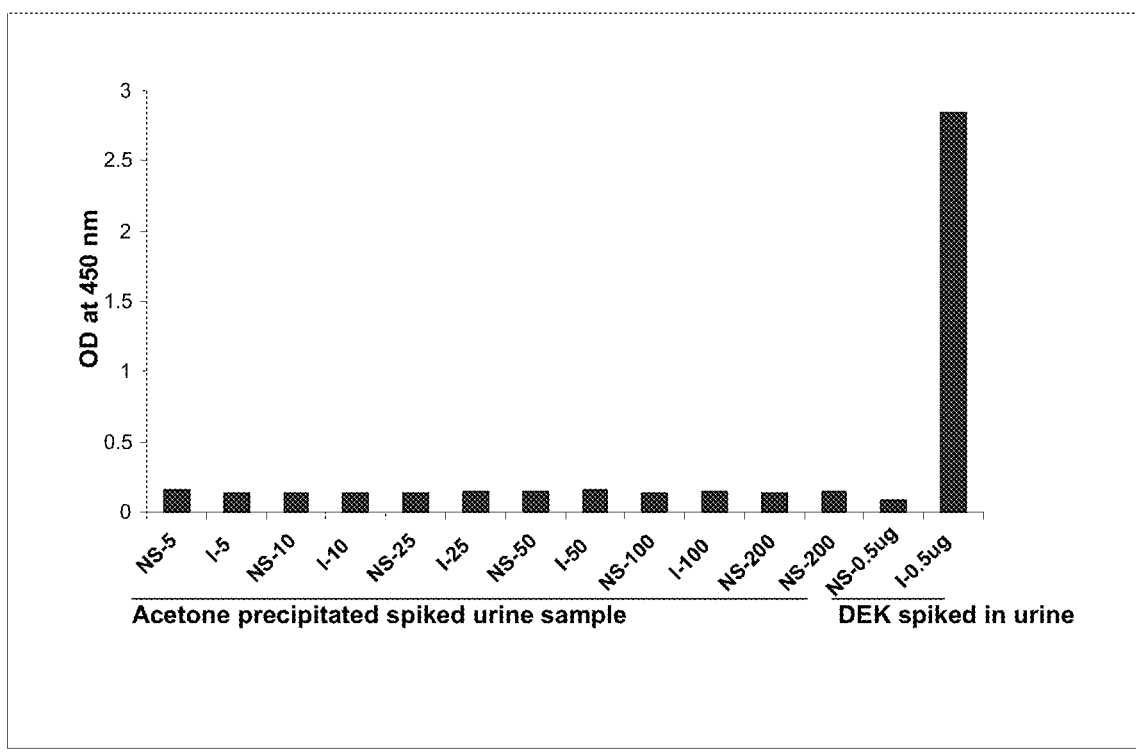
FIG. 23 depicts urine that subject to acetone precipitation fails to be detected for DEK by capture ELISA. In this study, recombinant DEK isoform 1 protein was spiked in control urine samples followed by acetone precipitation and re-suspension of precipitates in sucrose buffer. The re-suspended solution was analyzed by capture DEK ELISA. Noted that recombinant DEK was not detected in the spiked urine samples. In contrast, DEK spiked in control urine (without subject to acetone precipitation) could be readily detected by capture ELISA.

We spiked urine samples with different concentrations of recombinant DEK isoform 1 protein and proceeded to concentrate the spiked urine samples with our established concentration steps (See, Examples 10 and 11). In brief, spiked urine samples were subjected to acetone precipitation followed by Microcon concentration as described above. The concentrated urine samples were tested by capture DEK ELISA. In this study, we failed to detect DEK protein in acetone processed urine samples, even at concentration of 200 µg of spiked DEK protein. Noted that the developed ELISA is able to detect 0.5 µg of recombinant DEK protein when spiked into urine (i.e., without acetone treatment) (See, FIG. 23). Thus, these data indicate that the acetone precipitation step affects the ability of ELISA assay to detect DEK protein.

Figure 24:
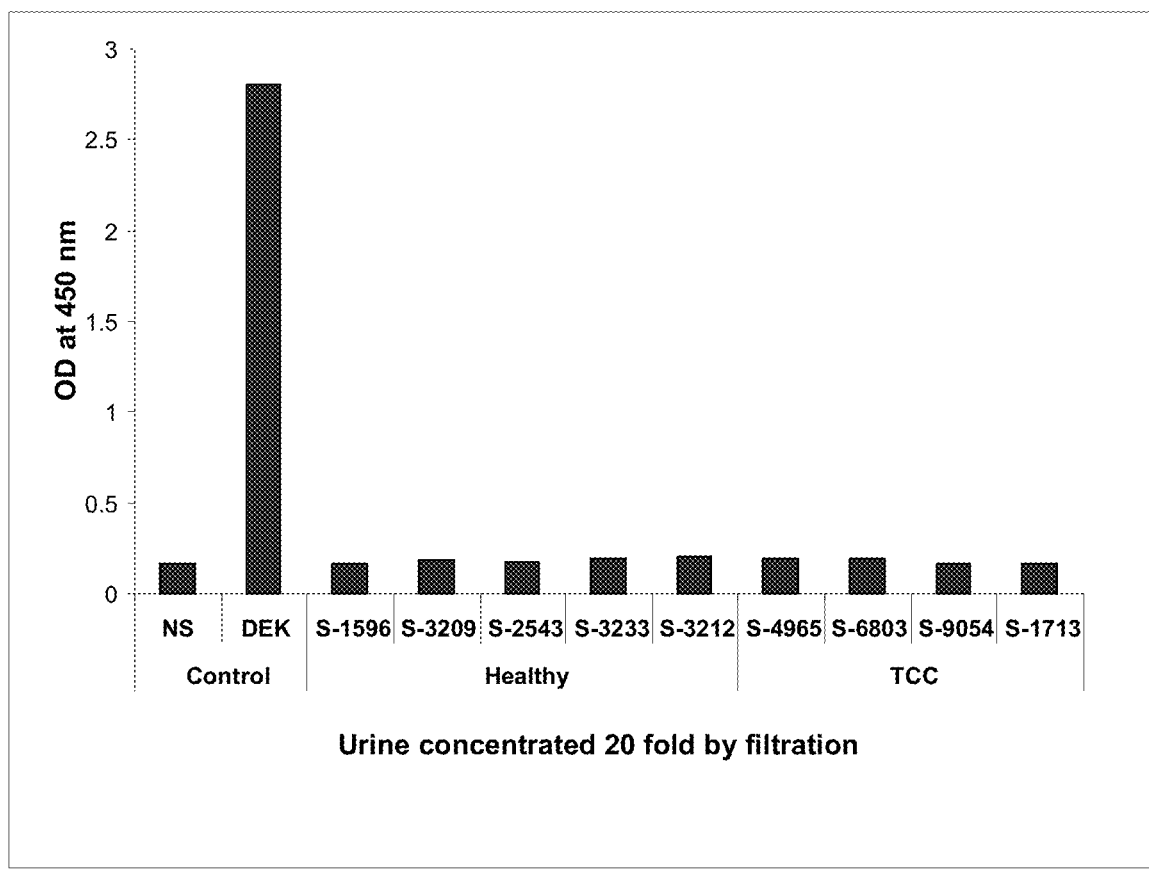
FIG. 24 depicts filtration-concentrated urine samples (by Microcon® 3K filter to 20 fold concentrated), when assayed by capture DEK ELISA, could not detect DEK.

Example 17 Test Clinical Samples Using Capture ELISA by Concentrating Urine Samples (20 Fold) Using a 3K Microcon Column 1 mL of urine (from a bladder cancer patient) was concentrated to 50 µL using a Microcon® 3K filter and tested for DEK presence using our developed capture ELISA. As shown in FIG. 24, we could not detect DEK protein in the urine of bladder cancer patients using the capture ELISA. It is speculated that the concentrated urine has too low amounts of DEK protein that is below the detection limit of the capture DEK ELISA. It is possible that DEK protein in the urine of bladder cancer patients may be a different isoform of DEK protein that may not be detectable by the mouse monoclonal DEK antibody used in the capture ELISA.

Example 18 Urine DEK Protein Contains DEK Isoform 2

DEK proteins are present in two isoforms; namely, DEK isoform 1 and DEK isoform 2. The detection antibody used in the capture ELISA only recognizes DEK isoform 1 and not DEK isoform 2. It is therefore possible that patients with TCC have DEK isoform 2 solely in the urine. Therefore we speculated that an anti-DEK antibody that would detect DEK isoform 2 would detect DEK in the urine of bladder cancer patients.

In this study, we compared the ability of three (3) different anti-DEK antibodies in detecting urine DEK from patients with bladder cancer. In this study, we used (i) a polyclonal anti-DEK antibody (#16448-1-AP, raised against the full length DEK isoform 1); (ii) a monoclonal anti-DEK antibody (#610948, raised against amino acids 19-169 DEK isoform 1); and (iii) a polyclonal anti-DEK antibody (A301-335A, raised against amino acids 325-375).

2 ml of urine sample from patients with bladder cancer and from healthy individual was concentrated to 100 µL (20 fold concentration) using a 3K Microcon® Filter and coated on a microtiter plate. The three (3) different antibodies were compared in its ability to detect DEK in urine of clinical samples. The antigen-antibody complex was detected by anti-mouse or anti-rabbit IgG conjugated with horseradish peroxidase (HRP). The peroxidase activity (representing the level of DEK) was measured by addition of tetramethylbenzidine (TMB) substrate. The color intensity was in direct proportion to the amount of the bound DEK. Color development was stopped by adding 1 M $H_2SO_4$ and the intensity of the color was measured at optical density (OD) 450 nm on a microtiter plate reader.

Results were summarized in Table 4. The two (2) polyclonal anti-DEK antibodies were able to detect urine DEK. In contrast, the monoclonal anti-DEK antibody failed to detect DEK. This data is consistent with our observation that the capture ELISA could not detect DEK in any of the clinical urine samples. Hence, any two (2) anti-DEK antibodies (recognizing different sites on DEK protein) could be used to detect DEK isoform 2 in the capture ELISA format.

TABLE 4

Comparison of Detection of Urine DEK by Indirect ELISA

| | Recognizes DEK Isoform 1 | Recognizes DEK Isoform 2 | Detect DEK in Urine of Bladder Cancer Patients |
|---|---|---|---|
| Monoclonal DEK Ab (#610948) | Yes | No | No |
| Polyclonal DEK Ab (#A301-335A) | Yes | Yes | Yes |
| Polyclonal DEK Ab (#16448-1-AP) | Yes | Yes | Yes |

Table 5 summaries the detection of DEK using a polyclonal DEK antibody (325-375) and a monoclonal DEK antibody (19-169) in detecting DEK protein from various biological samples.

TABLE 5

Ability of DEK Antibody in Detecting DEK Protein in Various Biological Sources

| | DEK protein detection in bladder tumor tissues and cultured bladder cancer cells | DEK protein detection in bladder tumor tissues | DEK protein in urine from bladder cancer patients |
|---|---|---|---|
| Monoclonal DEK Antibody (#610948) | Yes | Yes | No |
| Polyclonal DEK Antibody (#A301-335A) | Yes | Yes | Yes |

Example 19 Development of Indirect DEK ELISA for Detection of DEK Protein in Urine Samples Based on the results in Example 18, we developed an indirect ELISA for detecting DEK protein in urines of bladder cancer patients using an anti-DEK polyclonal antibody (#A301-335A).

Urine samples (2 ml aliquots) from (i) patients suffering bladder cancer (various grades), (ii) patients suspected TCC, (iii) patients with history of TCC and (iv) healthy individuals were concentrated to 100 µl (i.e., 20 fold concentrated) using a 3K Microcon filter. Concentrated urines were directly coated on microtiter plates.

An anti-DEK polyclonal antibody (A301-335A) was used for detection of bound DEK protein on the wells of the microtiter plates. The antigen-antibody complex was detected by anti-rabbit IgG conjugated with horseradish peroxidase (HRP). The peroxidase activity (representing the level of DEK) was measured by addition of tetramethylbenzidine (TMB) substrate. The color intensity was in direct proportion to the amount of the bound DEK.

Figure 25:
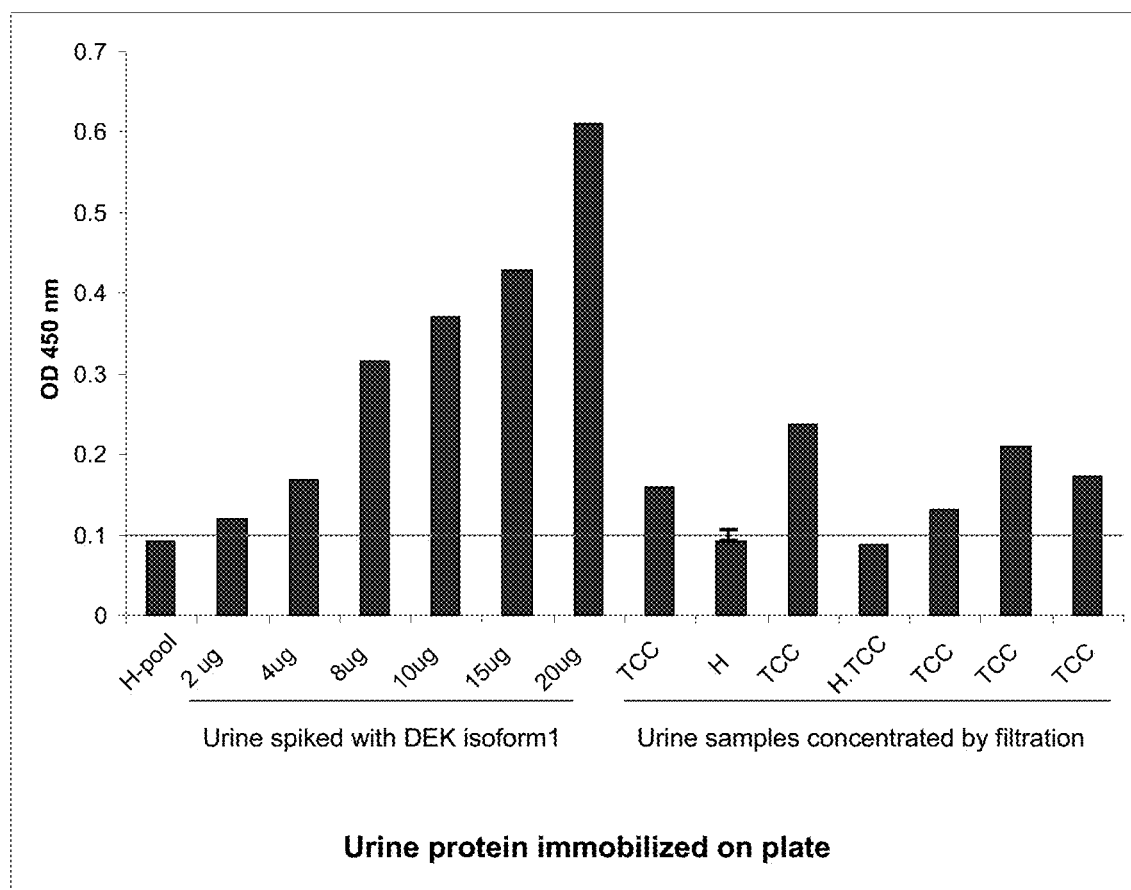
FIG. 25 depicts an indirect ELISA experiment. Filtration-concentrated urine (by Microcon® 3K filter to 20 fold concentrated) was first coated the wells of the microtiter plate. A DEK polyclonal antibody was used for DEK detection. Antigen-antibody complex was detected anti-rabbit IgG HRP. The peroxidase activity (representing the level of DEK) was measured by addition of tetramethylbenzidine (TMB) substrate.

DEK protein was detected in TCC urine samples, but not in the urine of healthy donors and patient with history of TCC (See, FIG. 25). This suggests that using an indirect ELISA method we were able to detect DEK protein specifically in the urine of bladder cancer patients.

Example 20 Limit of Detection for DEK Indirect ELISA

Figure 26:
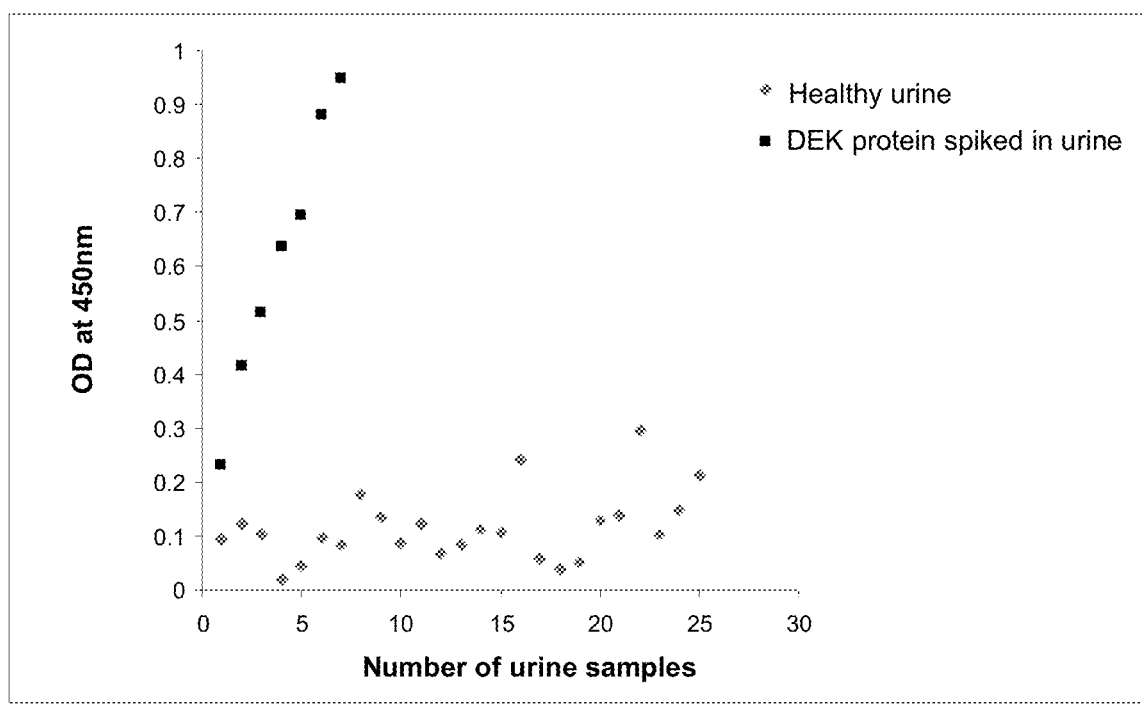
FIG. 26 depicts the analysis of 25 healthy donors to determine the cut-off value for the indirect DEK ELISA. Based on the standard curve of urine spiked with DEK, only two (2) healthy samples out of 25 had concentration above 0 µg but less than 0.98 µg. Thus, 1.5 µg was decided as the cut-off for detection of DEK protein based on standard deviation of all samples tested.

We determined the limit of detection of urine DEK using the indirect ELISA. For standard curve, we spiked 2 mL of urine samples with various concentration of recombinant DEK isoform 1 protein and concentrated the spiked urine samples to 20 fold and coated on the wells of microtiter plates. Next, we processed urine samples obtained from 25 healthy individual and employed the DEK polyclonal antibody (A301-335A), and the indirect ELISA as described in experiment 19. Based on standard curve of DEK, we determined the cut-off value for positive detection of DEK in urine samples at a concentration greater than 1.5 µg of DEK protein in 20-fold concentrated urine samples (See, FIG. 26).

Example 21 Correlation Between Urine DEK and Bladder Cancer

Figure 27:
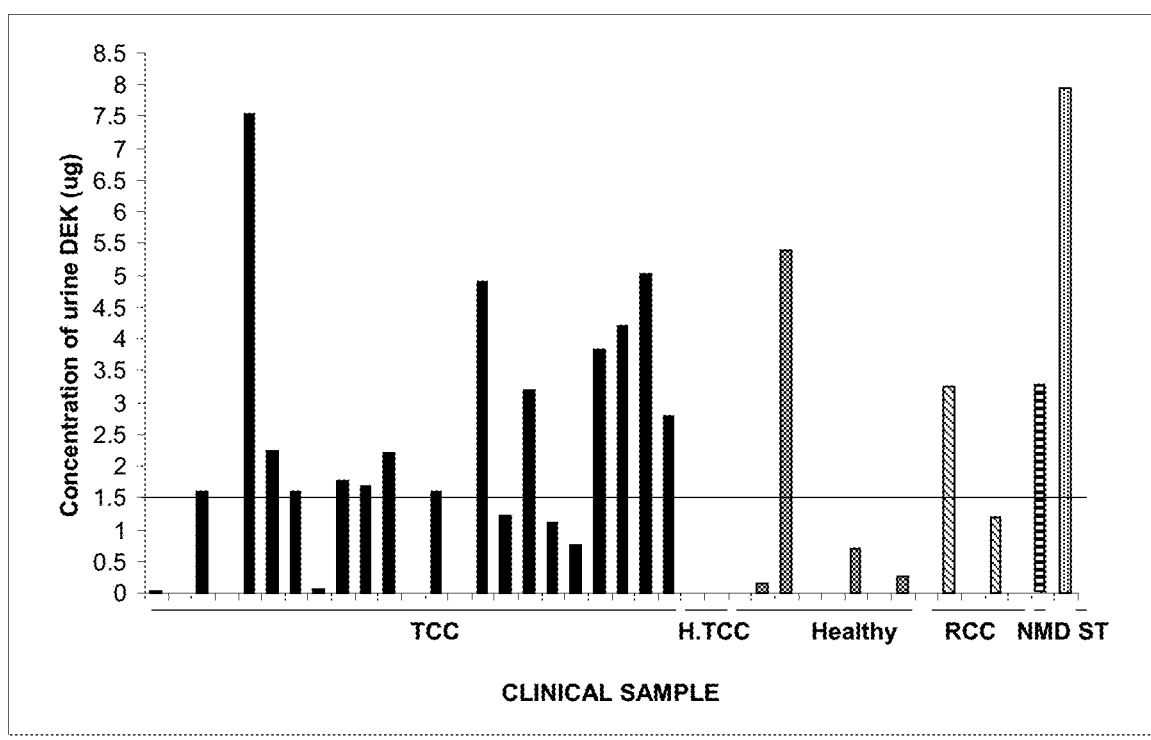
FIG. 27 depicts the detection of DEK in urines of bladder cancer patients using indirect DEK ELISA. 2 ml of urine sample was concentrated to 100 µl using 3K Microcon® filter to achieve and 20 fold concentration and analyzed by indirect DEK ELISA. The assay detects DEK protein in most of the bladder cancer patients with a sensitivity of 65% and specificity of 89%.

Next, we tested urine samples from 41 patients with TCC, healthy donors, renal cell carcinoma, history of TCC, non-malignant disease and individual with suspected bladder cancer. We used an indirect DEK ELISA and successfully detected DEK protein in urines from bladder cancer patients. The indirect DEK ELISA assay has a sensitivity of 67% and specificity of 85% (See, FIG. 27). This suggests that there is a strong correlation between the presence of DEK protein (isoform 2) in urines of patients with bladder cancer. Table 6 summarizes the data presented in FIG. 27.

TABLE 6

DEK Detection in Clinical Samples using Indirect ELISA

| DEK in Urine | TCC | H. TCC | NMD | RCC | Suspected Tumor | Healthy |
|---|---|---|---|---|---|---|
| Positive | 15 | 0 | 1 | 1 | 1 | 1 |
| Negative | 8 | 2 | 0 | 3 | 0 | 9 |

Example 22 Limit of Detection of Polyclonal Anti-DEK Antibody (A301-335A) by Western Blot and ELISA We determined the limit of detection of DEK polyclonal antibody by Western blot and by indirect ELISA. We spiked urine samples obtained from healthy individual and with increasing concentration of recombinant DEK isoform 1.

For Western blot assay, 13 ml of urine was spiked with 2.5, 5, 10, 15, 20, 30, 50, 60, 75 µg/mL concentration of recombinant DEK isoform 1. Spiked urine sample was subjected to acetone precipitation. Pellet was re-suspended in 2 mL of sucrose buffer. 400 µL of re-suspended buffer was concentrated using a 3K Microcon filter. Results indicate that at concentration of 15 µg/ml and higher DEK was detected in urine by Western blot using the DEK polyclonal antibody (A301-335A).

For indirect ELISA, we spiked 2, 4, 6, 8, 10, 16, 20 µg in 2 mL of urine samples. Spiked urine samples were concentrated using a 10K Microcon filter to a final volume of 125 µL. 125 µL was coated on the wells and subjected to indirect ELISA. Results indicate that concentration of ≥2 µg/mL recombinant DEK could be detected by indirect ELISA.

Table 7 summarizes the limit of detection study comparing Western blot analysis and ELISA assay.

TABLE 7

Limit of Detection - Western Blot v. Indirect ELISA

| Methods | Limit of Detection of Recombinant DEK in Spiked Urine Samples |
|---|---|
| Western Blot Assay | 15 µg/mL |
| Indirect ELISA Assay | 2 µg/mL |

Example 23 Production of Monoclonal DEK Antibodies Raised Against Peptide Sequences Corresponding to DEK Isoform 2

Figure 28:
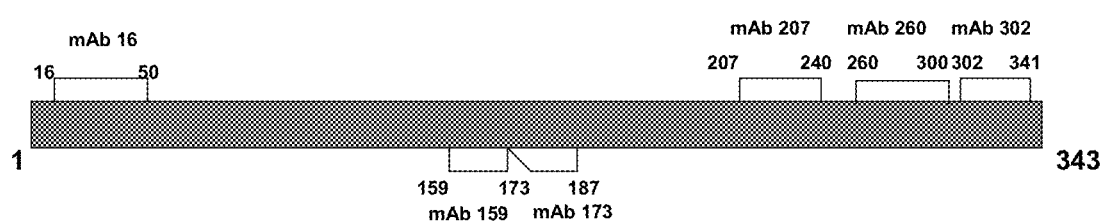
FIG. 28 depicts a schematic representation of the location of the different peptides sequences on the DEK isoform used for the generation of DEK monoclonal antibodies.

In this experiment, we sought to generate several monoclonal antibodies against human DEK protein. Our goal is employ the generated monoclonal antibodies in an ELISA. We used synthetic peptides as immunogens to raise monoclonal antibodies in mice. To ensure a better outcome, we prepared long synthetic peptide sequences (>30 amino acids) and short synthetic peptide sequences (<15 amino acids) that correspond to human DEK isoform 2 protein sequence (NCBI Accession No. for human DEK protein isoform 2 is NP_001128181.1) (SEQ ID NO: 2) and used them as immunogens for the generation of the monoclonal antibodies. FIG. 28 shows the location of corresponding peptide sequence in DEK isoform 2 for the generation of monoclonal antibodies.

Figure 29:
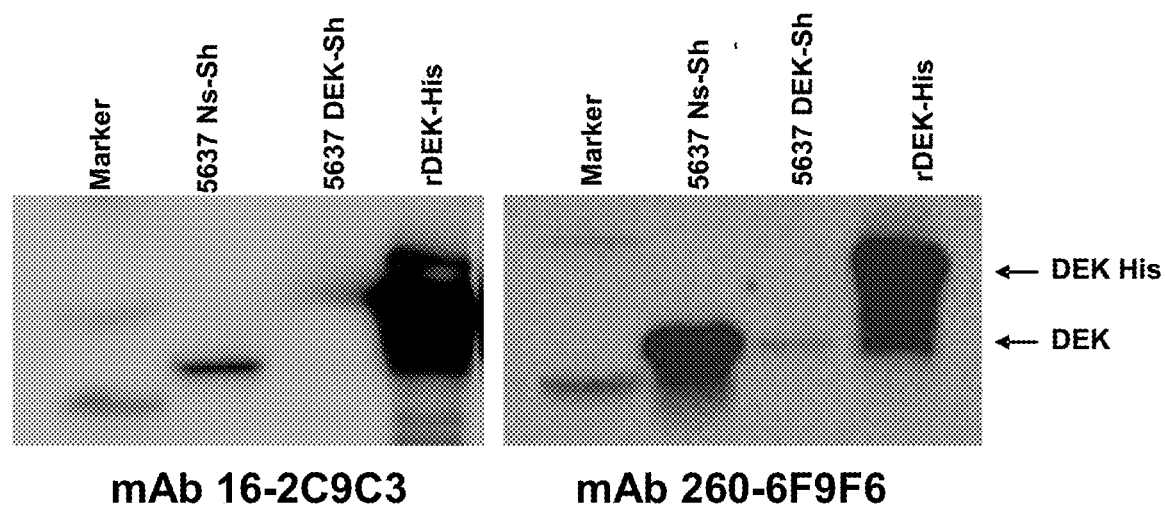
FIG. 29 depicts a Western blot experiment using mAb16-2C9C3 and mAb 260-6F9F6 antibodies on cell lysate and recombinant DEK protein. 30 µg of whole cell lysate from 5637 DEK-Sh cell line, 5637 Ns-Sh and 5 µg of recombinant DEK protein was run on a gel and analyzed by Western blot using mAb16-2C9C3 and mAb 260-6F9F6 antibodies. The assay detects both monoclonal antibodies against DEK in 5637 NsSh, but does not detect any of the antibodies against DEK in 5637 DEK-Sh cell lysate, depicting that mAb16-2C9C3 and mAb 260-6F9F6 are specific for DEK.

In the initial testing, we used Western blot analysis and indirect ELISA to test the bleeds from mice injected with the short or long DEK isoform 2 peptides using recombinant His-tagged DEK protein (rDEK-His). Based on the data obtained from the Western blot and antigen down ELISA, only three (mAb 16, mAb 260 and mAb 302) out of the four test bleeds derived from mice injected with long peptides indicated an immune response against DEK. The test bleeds derived from the mice injected with short peptides did not have an immune response against DEK. The reason for the failure in immune response and mAb production is unclear. Table 8 summarizes the reactivity of the peptide sequences against the DEK protein based on Western blot analysis and antigen down ELISA of test bleeds. In sum, using six (6) peptide sequences as immunogens, we successfully prepared mAb 16, mAb 260 and mAb 302.

rDEK-His. We preformed a Western blot analysis of purified monoclonal DEK antibody on cell lysate and rDEK His protein (FIG. 29). The purified antibodies were only able to detect DEK in the 5637 cell line with nonspecific ShRNA, as such the antibodies are specific for the DEK protein (Table 9).

Example 25 Analysis of Purified Monoclonal DEK Antibodies by Indirect ELISA Using Recombinant DEK Spiked into PBS In this series of experiments, we tested purified (isolated) monoclonal antibodies from the corresponding clones using an antigen down ELISA. We spiked various concentrations of rDEK into PBS. We spiked rDEK at 1 µg/mL and prepared a two-fold dilution series, such that our final concentrations were 1 µg/mL, 0.5 µg/mL. 0.25 µg/mL, 0.125 µg/mL, 0.062 µg/mL, 0.031 µg/mL and 0.015 µg/mL. 300 µL of sample was used in the antigen down ELISA and 300 µL of PBS was used as blank (i.e., control without rDEK). We used the purified antibodies at dilutions ranging from 1:1000 to 1:8000. We show that the purified antibodies tested in the antigen down ELISA were able to detect rDEK in PBS at a concentration of 15 ng/ml or less as shown in Table 9.

TABLE 8

Peptides for Monoclonal Antibody Production and Analysis of Test Bleeds for Immunogenicity

| DEK Monoclonal Antibody ID | Amino Acid Residues of DEK Isoform 2 Used for Generating mAb | WB Analysis and Indirect ELISA of Test Bleeds | Peptide Sequence |
|---|---|---|---|
| LONG PEPTIDES (> 30 amino acids) | | | |
| mAb 16 | aa 16-50 | √ | CQPASEKEPEMPGPREESEEEEDEDDEEEEEEEGK (SEQ ID NO: 4) |
| mAb 260 | aa 260-300 | √ | QNSSKKESESEDSSDDEPLIKKLKKPPTDEELKETIKKLLAC (SEQ ID NO: 5) |
| mAb 207 | aa 207-240 | Produced No Clones | EESSDDEDKESEEEEPPKKTAKREKPKQKATSKSKC (SEQ ID NO: 6) |
| mAb 302 | aa302-341 | √ | CSANLEEVTMKQICKKVYENYPTYDLTERKDFIKTTVKELIS (SEQ ID NO: 7) |
| SHORT PEPTIDES (< 15 amino acids) | | | |
| mAb 159 | aa 159-173 | Produced No Clones | CLPKSKKTCSKGSKK (SEQ ID NO: 8) |
| mAb 173 | aa 173-187 | Produced No Clones | CERNSSGMARKAKRT (SEQ ID NO: 9) |

Example 24 Analysis of Purified Monoclonal DEK Antibodies by Western Blot

We next used the mice that showed an immune response against DEK for making the hybridomas. The mice corresponding to mAb6, mAb260 and mAb302 were used for cell fusion. After cell fusion (hybridomas), we established multiple clones for the three (3) mAbs. Specifically, we prepared three (3) single clones for mAb16 (namely, mAb 16-1D4F8, mAb 16-1D4 F10 and mAb 16-2C9C3), three (3) single clones for mAb260 (namely, mAb 260-6C5G8, mAb 260-6F9F6 and mAb 260-6F9F6) and two (2) single clones for mAb 302 (namely, mAb 302-2B9A8 and mAb 302-3E9E11).

Next, we performed a Western blot analysis on the purified (isolated) monoclonal antibodies from the corresponding hybridomas using the 5637 cell line expressing DEK Sh RNA (DEK knockdown), non-specific ShRNA and against

Example 26 Analysis of Purified Monoclonal DEK Antibodies by Indirect ELISA Using Recombinant DEK Spiked into Urine In this series of studies, we tested whether the purified monoclonal antibodies were able to detect rDEK-His when spiked into neat urine. We spiked various concentrations of rDEK into the neat urine. We spiked rDEK at 1 µg/mL and prepared a two-fold dilution series, such that our final concentrations of rDEK were 1 µg/mL, 0.5 µg/ml, 0.25 µg/mL, 0.125 µg/mL, 0.062 µg/mL, 0.031 µg/mL and 0.015 µg/mL. 300 µL of spiked neat urine was used in the antigen down ELISA and 300 µL of neat urine was used as blank. The purified antibodies were used at dilutions ranging from 1:1000 to 1:8000.

We show that the purified monoclonal antibodies were able to detect rDEK in neat urine (Table 9). However, the sensitivity of detection varied between the different antibodies as well as between the different clones (Table 9).

TABLE 9

Summary of Purified (Isolated) Antibodies Tested by
Western Blot and by Antigen Down ELISA Using PBS or Urine

| Monoclonal Antibody ID | Western Blot Analysis | | Indirect ELISA Specifics | | | |
|---|---|---|---|---|---|---|
| | | | PBS | | Urine | |
| | Cell Lysate | Recombinant DEK protein | Dilution | Limit of Detection | Dilution | Limit of Detection |
| mAb 16-1D4F8 | ✓ | ✓ | 1:1000-1:8000 | 0.015 µg/mL | 1:1000-1:8000 | 0.125-0.062 µg/mL |
| mAb 16-1D4F10 | ✓ | ✓ | 1:1000-1:8000 | 0.015 µg/mL | 1:1000-1:8000 | 0.25-0.125 µg/mL |
| mAb 16-2C9C3 | ✓ | ✓ | 1:1000-1:8000 | 0.015 µg/mL | 1:2000-1:8000 | 0.125-0.062 µg/mL |
| mAb 260-6C5G8 | ✓ | ✓ | 1:1000-1:8000 | 0.015 µg/mL | 1:500-1:8000 | 0.25-0.125 µg/mL |
| mAb 260-6D11F2 | ✓ | ✓ | 1:1000-1:8000 | 0.015 µg/mL | 1:500-1:4000 | 0.015 µg/mL |
| mAb 260-6F9F6 | ✓ | ✓ | 1:1000-1:8000 | 0.015 µg/mL | 1:500-1:2000 | 0.015 µg/mL |
| mAb 302-2B9A8 | ✓ | ✓ | 1:1000-1:8000 | 0.015 µg/mL | 1:500-1:2000 | 0.015-0.007 µg/mL |
| mAb 302-3E9E11 | ✓ | ✓ | 1:1000-1:8000 | 0.015 µg/mL | 1:500-1:2000 | 0.015-0.007 µg/mL |

Example 27 Sandwich ELISA Using New Monoclonal DEK Antibodies and Recombinant DEK Spiked in Urine We tested different combinations of the newly raised monoclonal DEK antibodies in a sandwich ELISA using recombinant DEK spiked in neat urine obtained from a healthy donor. We immobilized a capture antibody on an ELISA plate and added various dilutions (ranging from 250 ng/mL to 2 ng/mL concentrations) of recombinant DEK (rDEK) spiked in urine to determine the limit of detection. 300 µL of neat spiked urine was tested in the sandwich ELISA. The detection monoclonal antibody was biotinylated using $PEG_{12}$ biotin and HRP and the labeled strepavidin antibody was used for detection of the sandwich complex (Table 10).

After multiple experiments, we found that only the pair consisting of mAb16-2C9C3 as the capture antibody and mAb260-6F9F6 and the detection antibody was able to detect DEK at a low concentration of 7-4 ng/mL in neat urine. All other tested pairs of monoclonal antibodies were only able to detect high concentrations (>250 ng/mL to 15 ng/mL) in neat urine. Concentrations of less than 10 ng/mL were considered the limit of detection for a sensitive sandwich ELISA to detect DEK.

TABLE 10

Summary of Limit of Detection of Various Pairs of DEK Monoclonal Antibodies Using Recombinant DEK Spiked in Urine

| Capture Antibody ↓ | Detection Antibody | | | |
|---|---|---|---|---|
| | mAb 260-6F9F6 (biotin) | mAb 16-2C9C3 (biotin) | mAb 302-2B9A8 (biotin) | mAd 302-3E9E11 (biotin) |
| mAb 260-6F9F6 | N/A* (same recognition sites) | 62-31 ng/mL | 62-31 ng/mL | 62-31 ng/mL |
| mAb 16-2C9C3 | 7.8-4 ng/mL | N/A (same recognition sites) | >2 µg/mL (High Background) | 15-7.8 ng/mL |
| mAb 302-2B9A8 | 15-7.8 ng/mL | >250 ng/mL | N/A (same recognition sites) | N/A (same recognition sites) |
| mAb 302-3E9E11 | 15-7.8 ng/mL | >250 ng/mL | N/A (same recognition sites) | N/A (same recognition sites) |

N/A* means not available. ELISA cannot be performed when same antibody is used.

Example 28 Performance of DEK Sandwich ELISA (mAb 16-2C9C3 and mAb 260-6F9F6-Biotin) in DEK Protein Spiked PBS and Urine We analyzed the performance of the DEK sandwich ELISA, consisting of mAb 16-2C9C3 as the capture antibody and mAb 260-6F9F6-biotin as the detection antibody, in detecting DEK protein spiked in either PBS or neat urine. We prepared rDEK standards in both PBS and urine. For urine, we used rDEK with a starting concentration of 125 ng/mL followed by a two-fold dilution series such that the lowest concentration of rDEK was 1.9 ng/mL. For PBS, we used rDEK with a starting concentration of 15.6 ng/ml followed by a twofold dilution series such that the lowest concentration of rDEK is PBS was 0.24 ng/mL, 300 µl of spiked PBS or spiked neat urine.

Figure 30B:
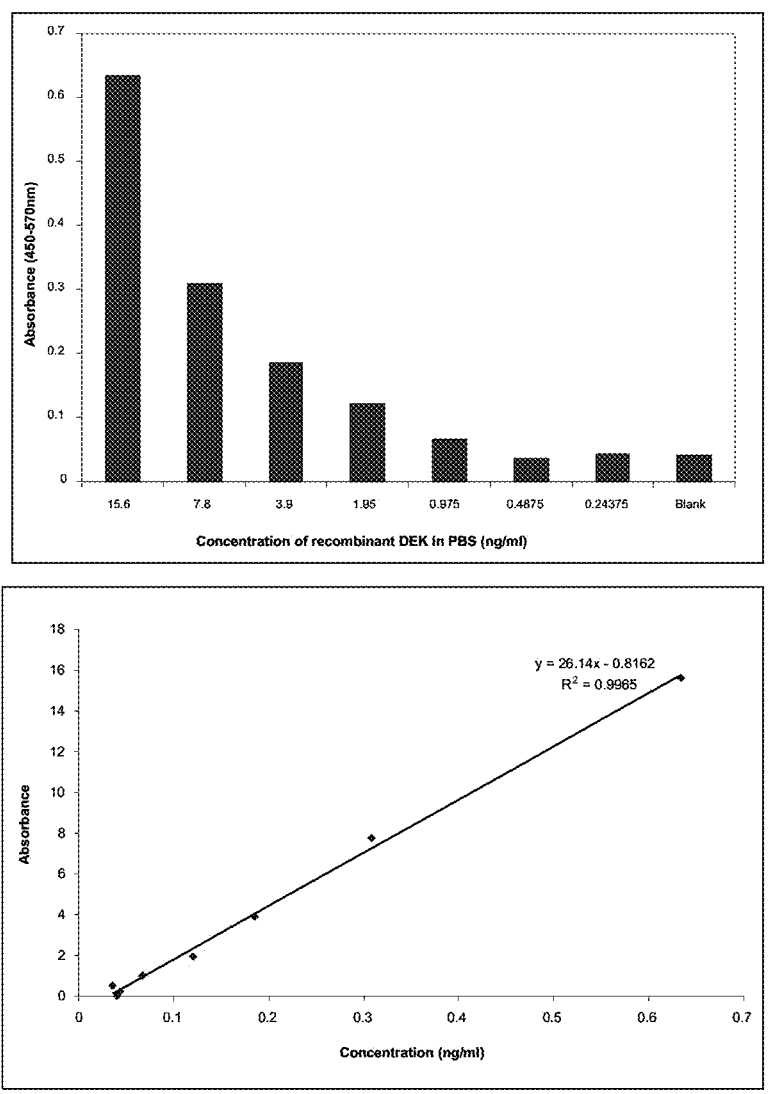
Figure 31:
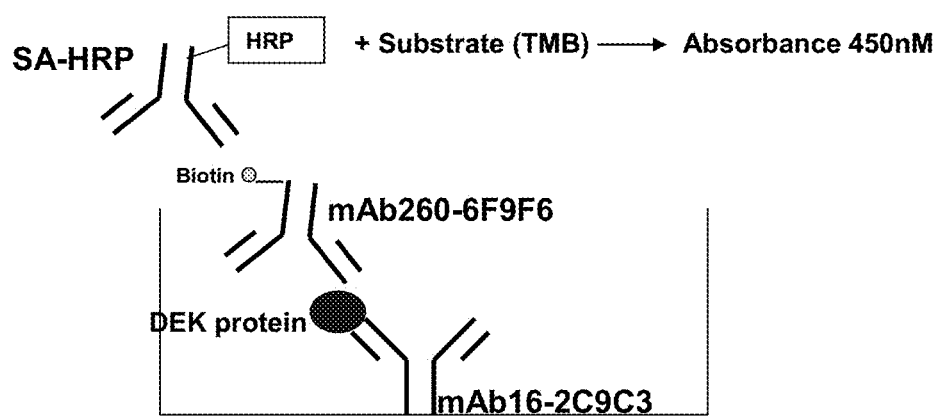
FIG. 31 depicts the diagrammatical representation of the DEK sandwich ELISA. The capture antibody, mAb16-

Our results indicate that the DEK sandwich ELISA detected rDEK at a concentration of ~4 ng/mL (FIG. 30A) whereas in PBS there was only a 2 fold increase in sensitivity to ~2 ng/mL (FIG. 30B) indicating that the antibody pair (mAb 16-2C9C3 and mAb 260-6F9F6) used in the DEK sandwich ELISA has minimum interfering effects of urine with high sensitivity and therefore can be used on neat urine for the detection of DEK (FIG. 29A). We have successfully developed a highly sensitive ELISA for DEK using the monoclonal antibodies (mAb 16-2C9C3 and mAb 260-6F9F6) that permit the detection of DEK at as low as 4 ng/ml in neat urine. To our surprise, the use of this anti-DEK monoclonal antibody pairs requires the ELISA without the use of concentrated urine. In other words, in contrast to the ELISA described in Example 17, neat urine is permitted when using mAb 16-2C9C3 and mAb 260-6F9F6 as the monoclonal antibody pair. Our new much improved DEK sandwich ELISA with high sensitivity is depicted in FIG. 31.

In further studies, we sequenced the clones 2C9C3 (mAb 16-2CC3) and 6F9F6 (mAb 260-6F9F6). FIG. 32 shows the location of the different CDR within the heavy and light chain of these monoclonal antibodies.

Example 29 DEK Sandwich ELISA (mAb 16-2C9C3 and mAb 260-6F9F6-Biotin) for the Detection of DEK The capture antibody (mAb 16-2C9C3) was coated on a 96 well ELISA plate at a concentration of 1-2 µg/mL in bicarbonate-carbonate buffer. Next, the plate was incubated at 4° C. for 1 hour. The plate was washed with wash buffer (1×PBS containing 0.05% Tween 20) and Casein blocking buffer is added to the well and incubated on a 96 well plate shaker at 450 rpm for 1 hour. Next, 300 µL of neat urine (clinical sample) and 300 µL of DEK (various rDEK protein dilutions prepared in synthetic urine) was added to the respective wells followed by incubation for 2 hours at room temperature. Following the washing step, the biotinylated detection DEK antibody mAb 260-6F9F6-biotin was added at a concentration of 1-2 µg/mL in 1×PBS and incubated for 1 hour. Following a wash step, HRP linked Strepavidin antibody was then added at 1:100 dilution and incubated for 1 hour. 150 µL of HRP substrate was then added to the washed wells and color development is allowed to take place for 2-10 min. The plate was then read at 450 and 590 nm.

Example 30 Performance of DEK Sandwich ELISA (mAb 16-2C9C3 and mAb260-6F9F6-Biotin) on Clinical Urine Sample to Detect Bladder Cancer We previously published that the DEK protein is elevated in the urine of bladder cancer patients. We tested our unexpectedly sensitive DEK sandwich ELISA on 35 clinical urine samples from patients suffering from bladder cancer (16 patients) and from patients with non-bladder cancer urogenital diseases (cystitis, stone and renal cell carcinoma) and healthy patients (19 patient samples).

Our DEK sandwich ELISA has a sensitivity of 82.3% and a specificity of 70.58%. The positive predictive value (PPV) of the sandwich ELISA is 75% and the negative predictive value (NPV) is 84.6% (FIG. 33).

Example 31 Performance Characteristics of the Improved DEK Sandwich ELISA Using mAb 16-2C9C3 and mAb 260-6F9F6 (Biotin)

We sought to determine the performance characteristics of our DEK sandwich ELISA comprising of mAb 16-2C9C3 as the capture antibody and mAb 260-6F9F6-biotin as the detection antibody. We prepared synthetic urine as a control to determine the performance characteristics. We made synthetic urine that consisted of 0.9% NaCl and 2% human albumin in water. We used the DEK sandwich ELISA to test rDEK spiked in synthetic urine and spiked healthy urine to confirm the synthetic urine as a control. We determined that assay sensitivity in synthetic urine was same as healthy urine samples (FIG. 34).

The following characteristics of the DEK sandwich ELISA were determined and are tabulated in Table 11:

I. Assay Sensitivity:

i) Assay sensitivity was determined by loading 10 sets of blanks (synthetic urine) as unknown samples and determining the result of the mean, plus 3 standard deviations (SD) of the 10 mean results, on the standard curve. Known concentration rDEK were run in duplicates for the standard curve.

Assay Sensitivity=Mean of blank+3 SD of blank

Based on the above equation the assay sensitivity of DEK sandwich ELISA was determined to be 3.9 ng/ml.

ii) We calculated the limit of blank from the 10 sets of blank which was used for limit of detection calculations.

Limit of Blank (LoB):

LoB=mean blank+1.645(SD blank)

II. Limit of Detection (LoD):

Limit of detection is the lowest concentration of DEK protein that can be measured reliably with the DEK sandwich ELISA. Based on the Clinical Laboratory standard Institute EP17 2004 publication, LoD was determined by utilizing both the measured limit LoB and test replicates of a sample known to contain a low concentration of analyte.

Six (6) replicates of all the different concentration of rDEK used in the standard curve were run in the DEK sandwich ELISA. The mean and standard deviation of the lowest concentration of the standards was calculated according and LoD is determined as indicated below.

LoD=LoB+1.645 (SD low concentration sample)

The SD of the lowest concentration calibrator should be less than 5% of LoB LoD was determined to be 3.9 ng/mL.

III. Limit of Quantification (LoQ)

We ran 10 sets of blanks (healthy urine only) as unknown samples and determined the result of the mean plus 10 times the standard deviations (SD) of the 10 mean results, on the standard curve.

Limit of quantification defined here as reagent blank+10 times standard deviation of reagent blank. We then ran the standards in duplicate for the standard curve.

LoQ=Mean blank+10×SD of blank

IV. Linearity of Dilution:

At least 5 (five) urine samples (clinical urine sample from bladder cancer patients) containing DEK were serially diluted with synthetic urine and assayed in duplicates. Linear regression analysis of the DEK antigen concentration versus dilution was performed.

Linearity of reportable range was performed carrying out serial dilutions of a known positive in synthetic urine then comparing the plotted regression value. The plotted regression value should not exceed 10% variance. Panel of Analytes: (the diluent solution: synthetic urine))

A=the positive control neat
B=1:2 dilution of the positive control
C=1:4 dilution of the positive control D=1:8 dilution of the positive control
E=1:16 dilution of the positive control
F=the negative control neat Each dilution was run in duplicate. The average value is plotted against the dilution factor. The slopes for the samples should range between 0.8-1.05 with a correlation coefficient of greater than 0.9, thus demonstrating that the samples will dilute linearly V. Recovery At least 3 positive samples were used to determine if DEK in urine can be recovered, suggesting that the DEK sandwich ELISA is specific for the DEK antigen. Known concentration of DEK from patient urine was added to negative urine sample at a 1:1 dilution. The samples were measured in duplicate. The mean of 2 assays is reported. Mean recoveries of DEK antigen from positive patient sample range between 84-107%.

VI. Precision

Precision testing is necessary to assess the reproducibility of the assay. For example, DEK positive urine samples must be consistently positive respectively to prove that there is true DEK detection when multiple operators test identical samples. Conversely, DEK negative samples must also consistently test negative when multiple operators repeat the assay. Precision testing was performed by running at least 3 known positive urine samples and 3 known negative urine sample in triplicates by 3 different operators on 3 separate days. The OD values should not deviate more than 15%. Reproducibility analysis of the precision panel was performed upon completion of all challenges. Reproducibility was translated into Inter-Assay Standard Derivation (SD) and Coefficient of Variation (CV %). Coefficient of Variation (CV %) was ranged from 7-30%.

TABLE 11

Performance Characteristics of DEK sandwich ELISA

| | |
|---|---|
| Assay Sensitivity | 3.9 ng/mL |
| Limit of Detection | 3.9 ng/mL |
| Limit of Quantification | 7.8-15 ng/mL |
| Linearity | Correlation Coefficient 0.91-0.97 |
| Precision | % CV 7-30% |
| Recovery | 84-107% |

Experimental Methods and Procedures

1. Cell Lines:

Human bladder cancer cell lines (e.g., T-24 and RT-4) were maintained in McCoy's 5A medium supplemented with 10% fetal bovine serum (FBS). Human bladder cancer cell lines (e.g., 5637 and TCCSUP) were maintained in RPMI supplemented with 10% FBS. SV-40 transformed human bladder urothelium cell line (i.e., UroTSA cell line) was maintained in DMEM medium supplemented with 10% FBS. Human bladder epithelium progenitor cell line (i.e., HBEP) (obtained from CELL N TEC®, Stauffacherstr, Bern, Switzerland) was maintained in CnT-58 medium. Differentiated epithelial cells were maintained in accordance with the manufacturer's protocol. All cell lines were maintained at 37° C. in 5% $CO_2$.

2. Whole Cell Lysates from Cell Lines:

Prior to cell lysis, cultured cells were washed with 10 ml of cold PBS. Cells were lysed using 1 mL of RIPA buffer (150 mM NaCl, 0.01 M sodium pyrophosphate, 10 mM EDTA, 10 mM sodium fluoride, 50 mM Tris ph 8.8, 0.1% SDS, 12.8 mM deoxycholic acid, 10% glycerol, 1% NP-40) supplemented with protease inhibitors (Roche, Indianapolis, Ind.) at a concentration of 1 µg/µL. Lysed cells were scraped and transferred to 1.5 ml centrifuge tube and centrifuged at 14,000 rpm for 10 min. to collect supernatant (i.e., whole cell lysates).

3. Urine and Tissue Sample Collections:

Urine samples were obtained from consented patients with bladder cancer (i.e., TCC), prostate cancer (i.e., CAP), renal cancer (i.e., RCC), non-malignant urogenital diseases and healthy individuals. Urine samples (~20-50 ml aliquots) were collected from patients in Wolfson Medical Center (Israel). Urine samples were stored in the presence of protease inhibitors (Complete Protease Inhibitor Tablets, Roche, Indianapolis, Ind.) at 1 µg/µL. Urine samples were immediately stored at −20° C. and shipped on dry ice. Upon arrival, samples were stored at −80° C.

Frozen, cold cut tissue samples from bladder tumor and adjacent normal tissues were obtained from patients from Wolfson Medical Center (Israel) as well as from ABS Analytical Biological Services Inc. (US).

4. Tissue Extracts from Tissue Samples:

Cold cut tissue samples were collected and immediately frozen upon removal. Samples were shipped on dried ice and stored at −80° C. To obtain tissue extract, cold cut frozen tissue samples were homogenized in RIPA buffer (400 µl) using a mortar and pestle. Homogenized tissue was centrifuged at 14,000 rpm at 4° C. for 20 min and supernatant was saved for downstream analysis. The amount of protein in each sample was quantified using a BCA assay kit (Pierce, Thermo Fisher Scientific, Rockford, Ill.).

5. Protein Extraction from Urine Pellet:

Urine was centrifuged at 3,000 rpm for 5 min. Pellet was washed three times with 10 ml PBS. Washed urine pellet was lysed in 100 µL lysis buffer (150 mM NaCl, 0.2% TritonX-100 and 10 mM Tris pH 7.4). 50 µL of urine pellet lysate was used for Western or Coomassie-blue staining studies.

6. Urine Pellet Lysates:

To obtain lysates from urine pellet, urine was first centrifuged at 3,000 rpm for 5 minutes to obtain a pellet. The pellet was then washed three times with 10 mL PBS and then lysed in 100 µl lysis buffer B (150 mM NaCl, 0.2% TritonX-100 and 10 mM Tris pH 7.4). 50 µL of the urine pellet lysate was used in the Western blot assay or in protein detection gels.

7. Chemical-Induced Precipitation of Protein in Urine:

Fresh urine samples were used in chemical induced protein precipitation. Alternatively, frozen urine samples were thawed at room temperature prior to protein precipitation. Chemicals used in protein precipitation included acetone, ethanol, TCA, and methanol-chloroform. These chemicals were used (preferably maintained at −20° C. when in use) in an amount sufficient to induce formation of precipitates in urine. The precipitates were then re-suspended in a sucrose buffer (10 mM triethanolamine and 250 mM sucrose).

8. Preparation of DEK Knockdown Cell Lines:

293FT cells (cat. no. R700-07, Invitrogen, Carlsbad, Calif.) were used in the preparation of DEK-ShRNA lentivirus particles. A DEK shRNA (TGCTGTTGACAGTGAGCGCGCACATTTGGCTTACAGTAAATAGTGAAGCCACAGATGTATTTACTGTAAGCCAAATGTGCTTGCCTACTGCCTCGGA) (SEQ ID NO: 1) was used to knockdown DEK expression. A lentiviral vector containing the DEK shRNA (pGIPZ-DEK shRNA) (cat. no. RHS4430-99137795) was purchased from Open Biosystems (Thermo-Scientific, Huntsville, Ala.). To prepare DEK-ShRNA lentivirus, $5\times10^5$ 293FT cells were first transfected with 10 µg of pGIPZ-DEK shRNA and 5 μg of the packaging vectors (i.e., pCMVAR8.2 and pHCMV-G) (a gift from Dr. Lairmore, The Ohio State University) (Wei, et al., Journal of Virology, February 2006, p 1242-1249, Vol. 80, No. 3) and grown at 37° C. in 5% $CO_2$. Supernatants of the transfected cells (containing lentivirus particles) were collected at 24 and 48 hours post-transfection. Debris in the supernatants was removed using a 0.45 μm filter.

To obtain DEK knockdown UroTSA cell line, 108 UroTSA cells was transduced with DEK shRNA lentiviral particles, 5 ml of the virus-containing filtrate was spread onto a 10 mm tissue culture dish containing confluent UroTSA cells. Cells were selected for DEK shRNA expression at 48 hours using puromycin (2.5 μg/μL) (Sigma-Aldrich, St. Louis, Mo.).

9. Preparation of DEK Over-Expressing Cell Lines:

DEK gene (NCBI Accession No. NM_003472.3) was cloned into a lentiviral vector (GATEWAY®). To prepare DEK over-expressing cells, $5 \times 10^5$ 293FT cells were first transfected with the DEK-lentiviral vector pLenti6/V5-DEST Gateway® (cat. no. K4960-00, Invitrogen, Carlsbad, Calif.) and a packaging mix (ViraPower™ BSD Packaging Mix, cat. no. K490-00, Invitrogen, Carlsbad, Calif.). Supernatants from the transfected cells were collected at 24 and 48 hours post-transfection and passed through a 0.45 μm filter at 50,000 rpm for 2 hours to remove debris.

5 ml of the virus-containing filtrate was spread onto a 10 mm tissue culture dish containing confluent UroTSA cells. Cells were selected for DEK-V5 expression at 48 hours using blasticidin (10 μg/μL) (Invitrogen, Carlsbad, Calif.).

10. Conductivity Measurements:

Various concentrations (0.1 mM. 0.25 mM, 0.5 mM, 2.5 mM, 5 mM and 10 mM) of potassium chloride were used to calibrate the conductivity meter (Traceable Expanded-Range Conductivity Meter, VWR, model no. 89094-958). Samples (e.g., urine) were prepared by adding 50 of sample to 5 ml of de-ionized water. Conductivity was measured by inserting the conductivity probe into the samples and is expressed as s/cm.

11. Preparation of DEK Knockdown and DEK-V5 Expressing UroTSA and 5637 Cell Lines DEK shRNA in lentiviral vector (pGIPZ) was purchased from Open Biosystems. Co-transfected 293FT cells with DEK shRNA pGIPZ, packaging vectors 8.2 and Env plasmids. 24 hours and 48 hours post-transfection culture supernatants containing the packaged lentiviral particles was collected and passed through a 0.45 μm filter. UroTSA and 5637 cell lines were transduced using the DEK shRNA containing lentivirus. 48 hours post transduction, cells expressing DEK shRNA was selected using puromycin. UroTSA DEK-V5 stable cell line was obtained by cloning DEK in GATEWAY® lentiviral vector and co-transfected with packaging mix from Invitrogen. Virus was harvested and cells transduced as described above and stable cell line expressing DEK-V5 selected using blasticidin.

12. Production of DEK Monoclonal Antibodies

Peptide was conjugated with KLH as immunogen and 5 BALB/c mice were immunized. The mice with satisfied immune response were used for cell fusion and hybridoma production. Briefly, the spleen of mice with satisfied immune response was taken and B cells were isolated from the splenocytes. Next the B cells were fused with Sp2/o murine myeloma cells and selected on HAT (hyoxanthine aminopterine thymidine) media. Surviving hybridomas were serially diluted into multi-well plates to such an extent that each well contained only one cell. The single cell was termed as a clone, since the antibodies in a well were produced by the same B cell, and was directed towards the same epitope. Supernatants of clones for corresponding initial peptide sequence were screened by indirect ELISA and the clone which showed maximum reactivity towards DEK antigen was used for the production of antibody. Five (5) mouse ascites production were done for 1 selected cell line (Clone) and the produced monoclonal antibodies in the ascites were purified by Protein G affinity column. The monoclonal antibodies obtained were determined to be IgG1 isotype.

13. Biotinylation of Monoclonal Antibody

EZ-Link NHS-PEG12 Biotin (#21312) was purchased from Thermo Scientific (Rockford, Ill.) and manufacturer's protocol was followed. We dissolved 1-10 mg protein to be modified in PBS. We removed an appropriate volume of 250 mM Biotin Reagent Stock Solution based on calculations using a 5- to 20-fold molar excess of EZ-Link NHS-PEG12-Biotin for protein solutions >2 mg/mL, dispensed it into the protein solution and mixed well. We then incubated the reaction on ice for two hours, removed excess non-reacted and hydrolyzed biotin reagent using a desalting column.

All publications and patents cited in this specification are herein incorporated by reference in their entirety. Although the invention has been described in connection with specific preferred embodiments and certain working examples, it should be understood that the invention as claimed should not be unduly limited to such specific embodiments. Various modifications and variations of the described composition, method, and systems of the invention will be apparent to those skilled in the art without departing from the scope and spirit of the invention.

What is claimed is:

1. A method of detecting bladder cancer in a human, comprising the steps of:
   (a) obtaining a urine sample from a human suspected of suffering from bladder cancer;
   (b) concentrating said urine sample;
   (c) immobilizing said concentrated urine sample onto a solid surface;
   (d) adding an anti-DEK antibody to said immobilized concentrated urine sample so as to allow a complex formation between DEK isoform 2 protein, and said anti-DEK antibody, said DEK Isoform 2 protein being a protein consisting of SEQ ID NO:2
      wherein said anti-DEK antibody recognizes DEK isoform 2 protein;
   (e) selecting said anti-DEK antibody from the group consisting of a monoclonal antibody 16-2C9C3 or a monoclonal antibody 260-6F9F6; and
   (e) detecting said protein-antibody complex, wherein the presence of said protein-antibody complex is indicative of a bladder cancer in said human.

2. The method of claim 1, wherein the anti-DEK antibody is a monoclonal antibody 16-2C9C3.

3. The method of claim 2, wherein the monoclonal antibody 16-2C9C3 comprises: (i) CDR1 of the heavy chain variable region which has the amino acid sequence of SEQ ID NO:15; (ii) CDR2 of the heavy chain variable region which has the amino acid sequence of SEQ ID NO:16; (iii) CDR3 of the heavy chain variable region which has the amino acid sequence of SEQ ID NO:17; (iv) CDR1 of the light chain variable region which has an amino acid sequence of SEQ ID NO: 23; (v) CDR2 of the light chain variable region which has the amino acid sequence of SEQ ID NO:24; and (vi) CDR3 of the light chain variable region which has the amino acid sequence of SEQ ID NO:25.

4. The method of claim 1, wherein the anti-DEK antibody is a monoclonal antibody 260-6F9F6.

5. The method of claim 4, wherein the monoclonal antibody 260-6F9F6 comprises: (i) CDR1 of the heavy chain variable region which has the amino acid sequence of SEQ ID NO:31; (ii) CDR2 of the heavy chain variable region which has the amino acid sequence of SEQ ID NO:32; (iii) CDR3 of the heavy chain variable region which has the amino acid sequence of SEQ ID NO:33; (iv) CDR1 of the light chain variable region which has an amino acid sequence of SEQ ID NO: 39; (v) CDR2 of the light chain variable region which has the amino acid sequence of SEQ ID NO:40; and (vi) CDR3 of the light chain variable region which has the amino acid sequence of SEQ ID NO:41.

6. A method of detecting bladder cancer in a human, comprising the steps of:
   (a) obtaining a urine sample from a human suspected of suffering from bladder cancer;
   (b) concentrating said urine sample;
   (c) immobilizing a first anti-DEK antibody onto a solid surface; said first anti-DEK antibody is a monoclonal antibody 16-2C9C3;
   (d) adding said concentrated urine sample onto said solid surface having said immobilized first anti-DEK antibody and allowing formation of DEK isoform 2 protein and first anti-DEK antibody complex;
   (e) removing unbound DEK isoform 2 protein; said DEK Isoform 2 is a protein consisting of SEQ ID NO: 2
   (f) adding a second anti-DEK antibody so as to allow formation of a complex between said bound DEK isoform 2 protein with said second anti-DEK antibody said second anti-DEK antibody is a monoclonal antibody 260-6F9F; and
   (g) detecting said bound DEK isoform 2 protein with said second anti-DEK antibody complex, wherein said first anti-DEK antibody and said second anti-DEK antibody recognize a different region of DEK isoform 2 protein, and wherein the presence of said protein-antibody complex is indicative of a bladder cancer in said human.

7. The method of claim 6, wherein the monoclonal antibody 16-2C9C3 comprises: (i) CDR1 of the heavy chain variable region which has the amino acid sequence of SEQ ID NO:15; (ii) CDR2 of the heavy chain variable region which has the amino acid sequence of SEQ ID NO:16; (iii) CDR3 of the heavy chain variable region which has the amino acid sequence of SEQ ID NO:17; (iv) CDR1 of the light chain variable region which has an amino acid sequence of SEQ ID NO: 23; (v) CDR2 of the light chain variable region which has the amino acid sequence of SEQ ID NO:24; and (vi) CDR3 of the light chain variable region which has the amino acid sequence of SEQ ID NO:25.

8. The method of claim 6, wherein the monoclonal antibody 260-6F9F6 comprises: (i) CDR1 of the heavy chain variable region which has the amino acid sequence of SEQ ID NO:31; (ii) CDR2 of the heavy chain variable region which has the amino acid sequence of SEQ ID NO:32; (iii) CDR3 of the heavy chain variable region which has the amino acid sequence of SEQ ID NO:33; (iv) CDR1 of the light chain variable region which has an amino acid sequence of SEQ ID NO: 39; (v) CDR2 of the light chain variable region which has the amino acid sequence of SEQ ID NO:40; and (vi) CDR3 of the light chain variable region which has the amino acid sequence of SEQ ID NO:41.

9. A method of detecting bladder cancer in a human, comprising the steps of:
   (a) obtaining a urine sample from a human suspected of suffering from bladder cancer;
   (b) concentrating said urine sample;
   (c) immobilizing a first anti-DEK antibody onto a solid surface;
   (d) adding said concentrated urine sample onto said solid surface having said immobilized first anti-DEK antibody and allowing formation of DEK isoform 2 protein and first anti-DEK antibody complex;
   (e) removing unbound DEK isoform 2 protein;
   (f) adding a second anti-DEK antibody so as to allow formation of a complex between said bound DEK isoform 2 protein with said second anti-DEK antibody; and
   (g) detecting said bound DEK isoform 2 protein with said second anti-DEK antibody complex, wherein said first anti-DEK antibody and said second anti-DEK antibody recognize a different region of DEK isoform 2 protein, and wherein the presence of said protein-antibody complex is indicative of a bladder cancer in said human;
   wherein the first anti-DEK antibody is a monoclonal antibody 16-2C9C3 and the second anti-DeK antibody is a monoclonal antibody 260-6F9F6.

* * * * *